US 7,242,984 B2

(12) United States Patent  
DiLorenzo

(10) Patent No.: US 7,242,984 B2  
(45) Date of Patent: Jul. 10, 2007

(54) APPARATUS AND METHOD FOR CLOSED-LOOP INTRACRANIAL STIMULATION FOR OPTIMAL CONTROL OF NEUROLOGICAL DISEASE

(75) Inventor: Daniel John DiLorenzo, Ft. Washington, MD (US)

(73) Assignee: NeuroVista Corporation, Seattle, WA (US)

( * ) Notice: Subject to any disclaimer, the term of this patent is extended or adjusted under 35 U.S.C. 154(b) by 366 days.

(21) Appl. No.: 10/753,205

(22) Filed: Jan. 6, 2004

(65) Prior Publication Data

US 2005/0119703 A1    Jun. 2, 2005

Related U.S. Application Data

(63) Continuation-in-part of application No. 10/718,248, filed on Nov. 20, 2003, which is a continuation-in-part of application No. 10/008,576, filed on Nov. 11, 2001, now Pat. No. 6,819,956, which is a continuation-in-part of application No. 09/340,326, filed on Jun. 25, 1999, now Pat. No. 6,366,813.

(60) Provisional application No. 60/438,286, filed on Jan. 6, 2003, provisional application No. 60/436,792, filed on Dec. 26, 2002, provisional application No. 60/427,699, filed on Nov. 20, 2002, provisional application No. 60/095,413, filed on Aug. 5, 1998.

(51) Int. Cl.  
*A61N 1/36* (2006.01)

(52) U.S. Cl. ...................................... 607/45

(58) Field of Classification Search .................. 607/45, 607/46, 58  
See application file for complete search history.

(56) References Cited

U.S. PATENT DOCUMENTS

| 3,218,638 | A | 11/1965 | Honig |
| 3,498,287 | A | 3/1970 | Ertl |
| 3,522,811 | A | 8/1970 | Schwartz et al. |
| 3,575,162 | A | 4/1971 | Gaarder |
| 3,837,331 | A | 9/1974 | Ross |

(Continued)

FOREIGN PATENT DOCUMENTS

CA    2251852    4/1999

(Continued)

OTHER PUBLICATIONS

Adjouadi, et al. A new mathematical approach based on orthogonal operators for the detection of interictal spikes in epileptogenic data. *Biomed. Sci. Instrum.* 2004; 40:175-80.

(Continued)

*Primary Examiner*—Scott M. Getzow  
(74) *Attorney, Agent, or Firm*—Shay Law Group LLP

(57) ABSTRACT

A neurological control system for modulating activity of any component or structure comprising the entirety or portion of the nervous system, or any structure interfaced thereto, generally referred to herein as a "nervous system component." The neurological control system generates neural modulation signals delivered to a nervous system component through one or more intracranial (IC) stimulating electrodes in accordance with treatment parameters. Such treatment parameters may be derived from a neural response to previously delivered neural modulation signals sensed by one or more sensors, each configured to sense a particular characteristic indicative of a neurological or psychiatric condition.

16 Claims, 42 Drawing Sheets

U.S. PATENT DOCUMENTS

| | | |
|---|---|---|
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,702,254 A | 10/1987 | Zabara |
| 4,768,176 A | 8/1988 | Kehr et al. |
| 4,768,177 A | 8/1988 | Kehr et al. |
| 4,793,353 A | 12/1988 | Borkan |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,920,979 A | 5/1990 | Bullara |
| 4,926,865 A | 5/1990 | Oman |
| 4,955,380 A | 9/1990 | Edell |
| 4,978,680 A | 12/1990 | Sofia |
| 4,979,511 A | 12/1990 | Terry |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE034,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varrichio |
| 5,188,104 A | 2/1993 | Wernicke |
| 5,190,029 A | 3/1993 | Byron et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varrichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,292,772 A | 3/1994 | Sofia |
| 5,293,879 A | 3/1994 | Vonk et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,314,458 A | 5/1994 | Najafi et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,150 A | 11/1996 | Wernicke |
| 5,575,813 A | 11/1996 | Edell et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,683,422 A | 11/1997 | Rise |
| 5,690,681 A | 11/1997 | Geddes et al. |
| 5,697,369 A | 12/1997 | Long |
| 5,700,282 A | 12/1997 | Zabara |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,792,186 A | 8/1998 | Rise |
| 5,800,474 A | 9/1998 | Benabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,899,922 A | 5/1999 | Loos |
| 5,916,239 A | 6/1999 | Geddes et al. |
| 5,917,429 A | 6/1999 | Otis, Jr. et al. |
| 5,928,272 A | 7/1999 | Adkins |
| 5,938,689 A | 8/1999 | Fischell et al. |
| 5,941,906 A | 8/1999 | Barreras et al. |
| 5,950,632 A | 9/1999 | Reber et al. |
| 5,971,594 A | 10/1999 | Sahai et al. |
| 5,975,085 A | 11/1999 | Rise |
| 5,978,702 A | 11/1999 | Ward et al. |
| 5,995,868 A | 11/1999 | Dorfmeister et al. |
| 6,006,124 A | 12/1999 | Fischell et al. |

| Patent No. | Date | Inventor |
|---|---|---|
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,104,956 A | 8/2000 | Naritoku |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,427,086 B1 | 7/2002 | Fischell et al. |
| 6,434,419 B1 | 8/2002 | Gevins et al. |
| 6,442,421 B1 | 8/2002 | Quyen et al. |
| 6,443,891 B1 | 9/2002 | Grevious |
| 6,453,198 B1 | 9/2002 | Torgerson |
| 6,459,936 B2 | 10/2002 | Fischell |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,507,754 B2 | 1/2003 | Quyen et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,587,727 B2 | 7/2003 | Osorio et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,594,524 B2 | 7/2003 | Esteller et al. |
| 6,597,953 B2 | 7/2003 | Boling |
| 6,597,954 B1 | 7/2003 | Pless et al. |
| 6,600,956 B2 | 7/2003 | Maschino |
| 6,606,521 B2 | 8/2003 | Paspa et al. |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,647,296 B2 | 11/2003 | Fischell et al. |
| 6,650,779 B2 | 11/2003 | Vachtsevanos et al. |
| 6,658,287 B1 | 12/2003 | Litt et al. |
| 6,662,035 B2 | 12/2003 | Sochor |
| 6,665,562 B2 | 12/2003 | Gluckman et al. |
| 6,668,191 B1 | 12/2003 | Boveja |
| 6,671,555 B2 | 12/2003 | Gielen |
| 6,671,556 B2 | 12/2003 | Osorio |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,721,603 B2 | 4/2004 | Zabara |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,788,975 B1 | 9/2004 | Whitehurst |
| 6,793,670 B2 | 9/2004 | Osorio |
| 6,810,285 B2 | 10/2004 | Pless et al. |
| 6,819,956 B2 | 11/2004 | DiLorenzo |
| 6,824,512 B2 | 11/2004 | Warkentin et al. |
| 6,873,872 B2 | 3/2005 | Gluckman et al. |
| 6,879,859 B1 | 4/2005 | Boveja |
| 6,904,390 B2 | 6/2005 | Nikitin et al. |
| 6,912,419 B2 | 6/2005 | Hill |
| 6,920,357 B2 | 7/2005 | Osorio |
| 6,921,538 B2 | 7/2005 | Donovan |
| 6,921,541 B2 | 7/2005 | Chasin et al. |
| 6,901,292 B2 | 8/2005 | Whitehurst |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriguez |
| 6,961,618 B2 | 11/2005 | Osorio |
| 6,973,342 B1 | 12/2005 | Swanson |
| 2002/0116042 A1 | 8/2001 | Boling |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0111542 A1 | 8/2002 | Warkentin et al. |
| 2002/0169485 A1 | 11/2002 | Pless et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0018367 A1 | 1/2003 | DiLorenzo |
| 2003/0028072 A1 | 2/2003 | Fischell et al. |

| | | |
|---|---|---|
| 2003/0050549 A1 | 3/2003 | Sochor |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0149457 A1 | 8/2003 | Tcheng et al. |
| 2003/0158587 A1 | 8/2003 | Esteller et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0199212 A1 | 10/2004 | Fischell |
| 2004/0267152 A1 | 12/2004 | Pineda et al. |
| 2005/0004621 A1 | 1/2005 | Boveja et al. |
| 2005/0010261 A1 | 1/2005 | Luders et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0049649 A1 | 3/2005 | Luders et al. |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0187789 A1 | 8/2005 | Hatlestad |
| 2005/0197590 A1 | 9/2005 | Osorio et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240242 A1 | 10/2005 | DiLorenzo |
| 2005/0240245 A1 | 10/2005 | Bange et al. |
| 2005/0245970 A1 | 11/2005 | Erickson et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |

FOREIGN PATENT DOCUMENTS

| | | |
|---|---|---|
| CA | 2423840 | 2/2002 |
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |

| | | |
|---|---|---|
| WO | WO 02/49500 A2 | 6/2002 |
| WO | WO 02/058536 A2 | 8/2002 |
| WO | WO 03/001996 A2 | 1/2003 |
| WO | WO 03/030734 A2 | 4/2003 |
| WO | WO 03/035165 A1 | 5/2003 |
| WO | WO 03/084605 A1 | 10/2003 |
| WO | WO 04/008373 A2 | 1/2004 |
| WO | WO 04/032720 A2 | 4/2004 |
| WO | WO 04/034231 A2 | 4/2004 |
| WO | WO 04/034879 A2 | 4/2004 |
| WO | WO 04/034880 A2 | 4/2004 |
| WO | WO 04/034881 A2 | 4/2004 |
| WO | WO 04/034882 A2 | 4/2004 |
| WO | WO 04/034883 A2 | 4/2004 |
| WO | WO 04/034885 A2 | 4/2004 |
| WO | WO 04/034982 A2 | 4/2004 |
| WO | WO 04/034997 A2 | 4/2004 |
| WO | WO 04/034998 A2 | 4/2004 |
| WO | WO 04/035130 A2 | 4/2004 |
| WO | WO 04/036370 A2 | 4/2004 |
| WO | WO 04/036372 A2 | 4/2004 |
| WO | WO 04/036376 A2 | 4/2004 |
| WO | WO 04/036377 A2 | 4/2004 |
| WO | WO 04/037342 A1 | 5/2004 |
| WO | WO 04/043536 A1 | 5/2004 |
| WO | WO 04/091718 A1 | 10/2004 |
| WO | WO 05/007236 A2 | 1/2005 |
| WO | WO 05/028026 A1 | 3/2005 |
| WO | WO 05/028028 A1 | 3/2005 |
| WO | WO 05/031630 A2 | 4/2005 |
| WO | WO 05/051167 A1 | 6/2005 |
| WO | WO 05/051306 A2 | 6/2005 |
| WO | WO 05/117693 A1 | 12/2005 |
| WO | WO 06/0014971 A2 | 2/2006 |
| WO | WO 06/0014972 A2 | 2/2006 |

OTHER PUBLICATIONS

Adjouadi, et al. Detection of interictal spikes and artifactual data through orthogonal transformations. J. Clin. Neurophysiol. 2005; 22(1):53-64.

Adjouadi, et al. Interictal spike detection using the Walsh transform. IEEE Trans. Biomed. Eng. 2004; 51(5): 868-72.

Aksenova, et al. Nonparametric on-line detection of changes in singnal spectral characteristics for early prediction of epilepsy seizure onset. J. Automation and Information Sciences. 2004; 36(8): 35-45.

Aksenova, et al. On-line disharmony detection for early prediction of epilepsy seizure onset. 5th International Workshop Neural Coding 2003. Aulla (Italy) Sep. 20-25, 2003. (Abstract).

Andrzejak, et al. Bivariate surrogate techniques: necessity, strengths, and caveats. Physical Review E. 2003; 68: 066202-1-066202-15.

Andrzejak, et al. Testing the null hypothesis of the nonexistence of a preseizure state. Physical Review E. 2003; 67: 010901-1-010901-4.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. *J Mol. Biol.* 13: 238-252.

Baruchi, et al. Functional holography of complex networks activity—From cultures to the human brain. Complexity. 2005; 10(3): 38-51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modelling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsytem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versus phase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

D'Alexxandro, et al. A multi-feature and multi-channel univariate selection process for seizure prediction. Clin. Neurophysiol. 2005; 116(3): 506-16.

Drury, et al. Seizure prediction using scalp electroencephalogram. Exp. Neurol. 2003; 184 Suppl 1: S9-18.

Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuous energy variation during the seizure cycle: towards an on-line accumulated energy. Clin. Neurophysiol. 2005; 116(3): 517-26.

Esteller, et al. Feature Parameter Optimization for Seizure Detection/prediction. *Proceedings of the 23rd Annual International Conference of the IEEE Engineering in Medicine and Biology Society*, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagus nerve stimulation for epilepsy, A report of the therapeutics and technology assessment subcommittee of the American Academy of Neurology. *Neurology*. 53: 666-669.

Gardner, A. B. A Novelty Detection Approach to Seizure Analysis from Intracranial EEG. Georgia Instititute of Technology. Apr. 2004. A disertation available at http://etd.gatech.edu/theses/available/etd-04122004-132404/unrestricted/gardner_andrew_b_200405_phd.pdf. Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernal Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. *ORNL/TM-2000/333 Oak Ridge National Laboratory*. Nov. 2000. Available at http://computing./ornl.gov/cse_home/staff/hively/NBICradaAnnualRptFY00.pdf. Accessed Feb. 28, 2006.

Hjorth, B. Source derivation simplifies topographical EEG interpretation. Am. J. EEG Technol. 1980; 20: 121-132.

Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.

Huynh, J. A. Evaluation of Gene Selection Using Support Vector Machine Recursive Feature Elimination. Arizona State University. May 26, 2004. (28 pages).

Huynh, J. A. Evaluation of Gene Selection Using Support Vector Machine Recursive Feature Elimination. Presentation slides. (41 pages) (May 26, 2004).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. *The Neuroscientist*. 1996; 2:118-126.

Iasemidis, et al. Comment on "Inability of lyapunov exponents to predict epileptic seaizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focus with Extrafocal Sites in Temporal Lobe Epilepsy (TLE). Ann. Neurol.1997; 42, pp. 429. pp. M146.

Iasemidis, et al. Epileptogenic Focus Localization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-64.

Iasemidis, et al. Long-term prospective on-line real-time seizure prediction. Clin. Neurophysiol. 2005; 116(3):532-44.

Iasemidis, et al. Long-Time-Scale Temporo-spatial Patterns of Entrainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3): 187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Versus Postictal Analysis for Epileptogenic Focus Localization. J. Clin. Neurophysiol. 1997; 14, pp. 144.

Iasemidis, et al. Quadratic binary programming and dynamic system approach to determine the predictability of epileptic seizures. *Journal of Combinatorial Optimization*. 2001; 5:9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

Iasemidis, et al. Spatiotemporal Evolution of Dynamical Measures Precedes Onset of Mesial Temporal Lobe Seizures. Epilepsia. 1994; 358, pp. 133.

Iasemidis, et al. Spatiotemporal Transition to Epileptic Seizures: A Nonlinear Dynamical Analysis of Scalp and Intracranial EEG Recordings. (In SILVA, F.L. Spatiotemporal Models in Biological and Artifical Systems. Ohmsha IOS Press. 1997; 37, pp. 81-88.

Iasemidis, et al. The evolution with time of the spatial distribution of the largest lyapunov exponent on the human epileptic cortex. World Scientific. 1991; pp. 49-82.

Iasemidis, et al. The Use of Dynamical Analysis of EEG Frequency Content in Seizure Prediction. American Electroencephalographic Society Annual Meeting, Oct. 1993.

Iasemidis, et al. Time Dependencies in Partial Epilepsy. 1993; 34, pp. 130-131.

Iasemidis, et al. Time dependencies in the occurrences of epileptic seizures, Epilepsy Res. 1994; 17(1):81-94.

Iasemidis, L. D. Epileptic seizure prediction and control. IEEE Trans. Biomed. Eng. 2003; 50(5):549-58.

Jerger, et al. Early seizure detection. Journal of Clin. Neurophysiol. 2001; 18(3):259-68.

Jerger, et al. Multivariate linear discrimination of seizures. Clin. Neurophysiol. 2005; 116(3):545-51.

Jouny et al. Characterization of epileptic seizure dynamics using Gabor atom density. Clin. Neurophysiol. 2003; 114(3):426-37.

Jouny, et al. Signal complexity and synchrony of epileptic seizures: is there an identifiable preictal period? Clin. Neurophysiol. 2005; 116(3):552-8.

Kapiris, et al. Similarities in precursory features in seismic shocks and epileptic seizures. Europhys. Lett. 2005; 69(4):657-663.

Katz, et al. Does interictal spiking change prior to seizures? Electroencephalogr. Clin. Neurophysiol. 1991; 79(2):153-6.

Kerem, et al. Forecasting epilepsy from the heart rate signal. Med. Biol. Eng. Comput. 2005; 43(2):230-9.

Khalilov, et al. Epileptogenic actions of GABA and fast oscillations in the developing hippocampus. Neuron. 2005; 48(5):787-96.

Korn, et al. Is there chaos in the brain? II. Experimental evidence and related models. C. R. Biol. 2003; 326(9):787-840.

Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006. (106 pages).

Kreuz, et al. Measure profile surrogates: a method to validate the performance of epileptic seizure prediction algorithms. Phys. Rev. E. 2004; 69(6 Pt 1):061915-1-9.

Lachaux, et al. Measuring phase synchrony in brain signals. Hum. Brain Mapp. 1999; 8(4):194-208.

Lai, et al. Controlled test for predictive power of Lyapunov exponents: their inability to predict epileptic seizures. Chaos. 2004; 14(3):630-42.

Lai, et al. Inability of Lyapunov exponents to predict epileptic seizures. Phys. Rev. Lett. 2003; 91(6):068102-1-4.

Latka, et al. Wavelet analysis of epileptic spikes. Phys. Rev. E. 2003; 67(5 Pt 1):052902 (6 pages).

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physica D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal focus localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy-an overview. Int. J. Psychophysiol. 1999; 34(1):45-52.

Lemos, et al. The weighted average reference montage. Electroencephalogr. Clin. Neurophysiol. 1991; 79(5):361-70.

Li, et al. Fractal spectral analysis of pre-epileptic seizures in terms of criticality. J. Neural Eng. 200; 2(2):11-6.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186(1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2):173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4(10):1173-6.

McSharry, et al. Comparison of predictability of epileptic seizures by a linear and a nonlinear method. IEEE Trans. Biomed. Eng. 2003; 50(5):628-33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate afterdischarges. Clin. Neurophysiol. 2002; 113(1):33-42.

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53(3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002;125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects In People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminium Foil Helmets: An Empirical Study. Available at http://people.csail.mit.edu/rahimi/helmet/..Accessed Mar. 2, 2006.

Remington's Pharmaceutical Sciences, latest edition, Mack Publishing Co., Easton P.

Robinson, et al. Steady States and Global Dynamics of Electrical Activity in the Cerebral Cortex. Phys. Rev. E. 1998; (59):3557-3571.

Rudrauf, et al. Frequency flows and the time-frequency dynamics of multivariate phase synchronization in brain signals. NeuroImage. 2005. (19 pages).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampus in Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989: 30(5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

Sackellares, J. C. Epilepsy—when chaos fails. In: chaos in the brain? Eds. K. Lehnertz & C.E. Elger. World Scientific. 2000 (22 pages).

Salant, et al. Prediction of epileptic seizures from two-channel EEG. Med. Biol. Eng. Comput. 1998; 36(5):549-56.

Schelter, et al. Testing for directed influences among neural signals using partial directed coherence. J. Neurosci. Methods. 2006; 152(1-2):210-9.

Schindler, et al. EEG analysis with simulated neuronal cell models helps to detect pre-seizure changes. Clin. Neurophysiol. 2002; 113(4):604-14.

Schwartzkroin, P. Origins of the Epileptic State. Epilepsia. 1997; 38, suppl. 8, pp. 853-858.

Sheridan, T. Humans and Automatiion. NY: John Wiley. 2002.

Shoeb et al. Patient-specific seizure detection. MIT Computer Science and Artificial Intelligence Laboratory. 2004; pp. 193-194.

Staba, et al. Quantitative analysis of high-frequency oscillations (80-500 Hz) recorded in human epileptic hippocampus and entorhinal cortex. J. Neurophysiol. 2002; 88(4):1743-52.

Stefanski, et al. Using chaos synchronization to estimate the largest lyapunov exponent of nonsmooth systems. Discrete Dynamics in Nature and Society. 2000; 4:207-215.

Subasi, et al. Classification of EEG signals using neural network and logistic regression. Computer Methods Programs Biomed. 2005; 78(2):87-99.

Szoka et al. A new procedure for preparation of liposomes with large internal aqueous space and high capture volume by reverse phase evaporation. 1978. *Proc. Natl Acad. Sci. USA*. 75: 4194-4198.

Tass, et al. Detection of n: m Phase Locking from Noisy Data: Application to Magnetoencephalography. Physical Review Letters. 1998; 81(15):3291-3294.

Terry, et al. An improved algorithm for the detection of dynamical interdependence in bivariate time-series. Biol. Cybern. 2003; 88(2):129-36.

Tetzlaff, et al. Cellular neural networks (CNN) with linear weight functions for a prediction of epileptic seizures. Int'l . J. of Neural Systems. 2003; 13(6):489-498.

Theiler, et al. Testing for non-linearity in time series: the method of surrogate data. Physica D. 1992; 58:77-94.

Tsakalis, K. S. Prediction and control of epileptic seizures: Coupled oscillator models. Arizona State University. (Slide: 53 pages) (No date).

Van Drongelen, et al. Seizure anticipation in pediatric epilepsy: use of Kolmogorov entropy. Pediatr. Neurol. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neurol. 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to access and compare seizure prediction methods. Epilepsy Behav. 2003; 4(3):318-25.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T B. Ho, D. Cheung, and H. Liu (Eds.): PAKDD. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518-1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114(10):1963-73.

Daniel John Dilorenzo, U.S. Appl. No. 10/858,899, entitled "Closed-loop feedback-driven neuromodulation," filed Jun. 1, 2004 (WSGR Reference No. 31685-704.505).

Daniel John Dilorenzo, et al., U.S. Appl. No. 11/159,842, entitled "Closed-loop feedback-driven neuromodulation," filed Jun. 22, 2005 (WSGR Reference No. 31685-704.508).

Daniel J. Dilorenzo, U.S. Appl. No. 11/234,873, entitled "Systems and methods for monitoring a patient's neurological disease state," filed Sep. 23, 2005 (WSGR Reference No. 31685-704.509).

Daniel J. Dilorenzo, U.S. Appl. No. 11/239,653, entitled "Systems and methods for monitoring a patien's neurological disease state," filed Sep. 28, 2005 (WSGR Reference No. 31685-704.510).

Daniel John Dilorenzo, U.S. Appl. No. 11/282,317 entitled "Closed-loop vagus nerve stimulation," filed Nov. 17, 2005 (WSGR Reference No. 31685-704.511).

Kent W. Leyde, et al., U.S. Appl. No. 11/321,897, entitled "Methods and systems for recommending an appropriate action to a patient for managing epilepsy and other neurological disorders," filed Dec. 28, 2005 (WSGR Reference No. 31685-713.201).

Daniel J. Dilorenzo, et al., U.S. Appl. No. 11/321,989, entitled "Methods and systems for recommending an appropriate pharmacological treatment to a patient for managing epilepsy and other neurological disorders," filed Dec. 28, 2005 (WSGR Reference No. 31685-713.202).

Mike Bland, et al., U.S. Appl. No. 11/322,150, entitled "Systems and methods for characterizing a patient's propensity for a neurological event and for communicating with a pharmacological agent dispenser," filed Dec. 28, 2005 (WSGR Reference No. 31685-713.203).

APPARATUS AND METHOD FOR CLOSED-LOOP INTRACRANIAL STIMULATION FOR OPTIMAL CONTROL OF NEUROLOGICAL DISEASE

CROSS REFERENCE TO RELATED APPLICATIONS

This application claims the benefit of U.S. Provisional Application Ser. No. 60/438,286, filed Jan. 6, 2003; this application is also a continuation-in-part of U.S. application Ser. No. 10/718,248, filed Nov. 20, 2003, which is a continuation-in-part of U.S. application Ser. No. 10/008,576, filed Nov. 11, 2001 (now issued as U.S. Pat. No. 6,819,956), which is a continuation-in-part of U.S. application Ser. No. 09/340,326, filed Jun. 25, 1999 (now issued as U.S. Pat. No. 6,366,813), which claims the benefit of U.S. Provisional Application Ser. No. 60/095,413, filed Aug. 5, 1998; U.S. patent application Ser. No. 10/718,248 also claims benefit of U.S. Provisional Application Ser. No. 60/427,699, filed Nov. 20, 2002 and claims benefit of U.S. Provisional Application Ser. No. 60/436,792, filed Dec. 27, 2002.

BACKGROUND OF THE INVENTION

1. Field of the Invention

The present invention relates generally to neurological disease and, more particularly, to intracranial stimulation for optimal control of movement disorders and other neurological disease.

2. Related Art

There are a wide variety of treatment modalities for neurological disease including movement disorders such as Parkinson's disease, Huntington's disease, and Restless Leg Syndrome, as well as psychiatric disease including depression, bipolar disorder and borderline personality disorders. These treatment modalities are moderately efficacious; however, they suffer from several severe drawbacks. Each of these traditional treatment modalities and their associated limitations are described below.

One common conventional technique for controlling neurological disease includes the use of dopaminergic agonists or anticholinergic agents. Medical management using these techniques requires considerable iteration in dosing adjustments before an "optimal" balance between efficacy and side effect minimization is achieved. Variation, including both circadian and postprandial variations, causes wide fluctuation in symptomatology. This commonly results in alternation between "on" and "off" periods during which the patient possesses and loses motor functionality, respectively.

Another traditional approach for controlling movement disorders is tissue ablation. Tissue ablation is most commonly accomplished through stereotactic neurosurgical procedures, including pallidotomy, thalamotomy, subthalamotomy, and other lesioning procedures. These procedures have been found to be moderately efficacious. However, in addition to posing risks that are inherent to neurosurgical operations, these procedures suffer from a number of fundamental limitations. One such limitation is that tissue removal or destruction is irreversible. As a result, excessive or inadvertent removal of tissue cannot be remedied.

Furthermore, undesirable side effects, including compromise of vision and motor or sensory functions, are likely to be permanent conditions. In particular, bilateral interventions place the patient at considerable risk for developing permanent neurologic side effects, including incontinence, aphasia, and grave psychic disorders. An additional drawback to this approach is that the "magnitude" of treatment is constant. That is, it is not possible to vary treatment intensity over time, as may be required to match circadian, postprandial, and other fluctuations in symptomatology and consequent therapeutic needs. Thus, decrease in treatment "magnitude" is not possible while an increase in treatment "magnitude" necessitates reoperation. Some adjustment is possible through augmentation with pharmacologic treatment; however, these additional treatments are subject to the above-noted limitations related to drug therapy.

Another traditional approach for controlling movement disorders and other neurological disease includes tissue transplantation, typically from animal or human mesencephalic cells. Although tissue transplantation in humans has been performed for many years, it remains experimental and is limited by ethical concerns when performed using a human source. Furthermore, graft survival, as well as subsequent functional connection with intracranial nuclei, are problematic. The yield, or percentage of surviving cells, is relatively small and is not always predictable, posing difficulties with respect to the control of treatment "magnitude."

Another traditional approach for controlling neurological disease is the continuous electrical stimulation of a predetermined neurological region. Chronic high frequency intracranial electrical stimulation is typically used to inhibit cellular activity in an attempt to functionally replicate the effect of tissue ablation, such as pallidotomy and thalamotomy. Acute electrical stimulation and electrical recording and impedance measuring of neural tissue have been used for several decades in the identification of brain structures for both research purposes as well as for target localization during neurosurgical operations for a variety of neurological diseases. During intraoperative electrical stimulation, reduction in tremor has been achieved using frequencies typically on the order of 75 to 330 Hz. Based on these findings, chronically implanted constant-amplitude electrical stimulators have been implanted in such sites as the thalamus, subthalamic nucleus and globus pallidus.

Chronic constant-amplitude stimulation has been shown to be moderately efficacious. However, it has also been found to be limited by the lack of responsiveness to change in patient system symptomatology and neuromotor function. Following implantation, a protracted phase of parameter adjustment, typically lasting several weeks to months, is endured by the patient while stimulation parameters are interactively adjusted during a series of patient appointments. Once determined, an "acceptable" treatment magnitude is maintained as a constant stimulation level. A drawback to this approach is that the system is not responsive to changes in patient need for treatment. Stimulation is typically augmented with pharmacological treatment to accommodate such changes, causing fluctuation of the net magnitude of treatment with the plasma levels of the pharmacologic agent.

As noted, while the above and other convention treatment modalities offer some benefit to patients with movement disorders, their efficacy is limited. For the above-noted reasons, with such treatment modalities it is difficult and often impossible to arrive at an optimal treatment "magnitude," that is, an optimal dose or intensity of treatment. Furthermore, patients are subjected to periods of overtreatment and undertreatment due to variations in disease state. Such disease state variations include, for example, circadian fluctuations, postprandial (after meal) and nutrition variations, transients accompanying variations in plasma concentrations of pharmacological agents, chronic progression of disease, and others.

Moreover, a particularly significant drawback to the above and other traditional treatment modalities is that they suffer from inconsistencies in treatment magnitude. For example, with respect to drug therapy, a decrease in responsiveness to pharmacologic agents eventually progresses to eventually preclude effective pharmacologic treatment. With respect to tissue ablation, progression of disease often necessitates reoperation to extend pallidotomy and thalamotomy lesion dimensions. Regarding tissue transplantation, imbalances between cell transplant formation rates and cell death rates cause unanticipated fluctuations in treatment magnitude. For continuous electrical stimulation, changes in electrode position, electrode impedance, as well as patient responsiveness to stimulation and augmentative pharmacologic agents, cause a change in response to a constant magnitude of therapy.

Currently, magnets commonly serve as input devices used by patients with implantable stimulators, including deep brain stimulators, pacemakers, and spinal cord stimulators. Current systems require the patient to manually turn the system off at night time to conserve battery power and use such magnets to maintain system power. This presents considerable difficulty to many patients whose tremor significantly impairs arm function, as they are unable to hold a magnet in a stable manner over the implanted electronics module. Consequently, many patients are unable to turn their stimulators on in the morning without assistance.

What is needed, therefore, is an apparatus and method for treatment of patients with neurological disease in general and movement disorders in particular that is capable of determining and providing an optimal dose or intensity of treatment. Furthermore, the apparatus and method should be responsive to unpredictable changes in symptomatology and minimize alternations between states of overtreatment and undertreatment. The system should also be capable of anticipating future changes in symptomatology and neuromotor functionality, and being responsive to such changes when they occur.

SUMMARY OF THE INVENTION

The present invention is a neurological control system for modulating activity of any component or structure comprising the entirety or portion of the nervous system, or any structure interfaced thereto, generally referred to herein as a "nervous system component." The neurological control system generates neural modulation signals delivered to a nervous system component through one or more intracranial (IC) stimulating electrodes in accordance with treatment parameters. Such treatment parameters may be derived from a neural response to previously delivered neural modulation signals sensed by one or more sensors, each configured to sense a particular characteristic indicative of a neurological or psychiatric condition. Neural modulation signals include any control signal that enhances or inhibits cell activity. Significantly the neurological control system considers neural response, in the form of the sensory feedback, as an indication of neurological disease state and/or responsiveness to therapy, in the determination of treatment parameters.

In one aspect of the invention, a neural modulation system for use in treating disease which provides stimulus intensity that may be varied is disclosed. The stimulation may be at least one of activating, inhibitory, and a combination of activating and inhibitory and the disease is at least one of neurologic and psychiatric. For example, the neurologic disease may include Parkinson's disease, Huntington's disease, Parkinsonism, rigidity, hemiballism, choreoathetosis, dystonia, akinesia, bradykinesia, hyperkinesia, other movement disorder, epilepsy, or the seizure disorder. The psychiatric disease may include, for example, depression, bipolar disorder, other affective disorder, anxiety, phobia, schizophrenia, multiple personality disorder. The psychiatric disorder may also include substance abuse, attention deficit hyperactivity disorder, impaired control of aggression, or impaired control of sexual behavior.

In another aspect of the invention, a neurological control system is disclosed. The neurological control system modulates the activity of at least one nervous system component, and includes at least one intracranial stimulating electrode, each constructed and arranged to deliver a neural modulation signal to at least one nervous system component; at least one sensor, each constructed and arranged to sense at least one parameter, including but not limited to physiologic values and neural signals, which is indicative of at least one of disease state, magnitude of symptoms, and response to therapy; and a stimulating and recording unit constructed and arranged to generate said neural modulation signal based upon a neural response sensed by said at least one sensor in response to a previously delivered neural modulation signal.

In another aspect of the invention, an apparatus for modulating the activity of at least one nervous system component is disclosed. The apparatus includes means for delivering neural modulation signal to said nervous system component; and means for sensing neural response to said neural modulation signal. In one embodiment, the delivery means comprises means for generating said neural modulation signal, said generating means includes signal conditioning means for conditioning sensed neural response signals, said conditioning including but not limited to at least one of amplification, lowpass filtering, highpass filtering, bandpass filtering, notch filtering, root-mean square calculation, envelope determination, and rectification; signal processing means for processing said conditioned sensed neural response signals to determine neural system states, including but not limited to a single or plurality of physiologic states and a single or plurality of disease states; and controller means for adjusting neural modulation signal in response to sensed neural response to signal.

Advantageously, aspects of the neurological control system are capable of incorporating quantitative and qualitative measures of patient symptomatology and neuromotor circuitry function in the regulation of treatment magnitude.

Another advantage of certain aspects of the present invention is that it performs automated determination of the optimum magnitude of treatment. By sensing and quantifying the magnitude and frequency of tremor activity in the patient, a quantitative representation of the level or "state" of the disease is determined. The disease state is monitored as treatment parameters are automatically varied, and the local or absolute minimum in disease state is achieved as the optimal set of stimulation parameters is converged upon. The disease state may be represented as a single value or a vector or matrix of values; in the latter two cases, a multi variable optimization algorithm is employed with appropriate weighting factors. Automated optimization of treatment parameters expedites achievement of satisfactory treatment of the patient, reducing the time and number of interactions, typically in physician visits, endured by the patient. This optimization includes selection of electrode polarities, electrode configurations stimulating parameter waveforms, temporal profile of stimulation magnitude, stimulation duty cycles, baseline stimulation magnitude, intermittent stimulation magnitude and timing, and other stimulation parameters.

Another advantage of certain aspects of the present invention is its provision of signal processed sensory feedback signals to clinicians to augment their manual selection of optimum treatment magnitude and pattern. Sensory feedback signals provided to the clinician via a clinician-patient interface include but are not limited to tremor estimates, electromyography (EMG) signals, EEG signals, accelerometer signals, acoustic signals, peripheral nerve signals, cranial nerve signals, cerebral or cerebellar cortical signals, signals from basal ganglia, signals from other brain or spinal cord structures, and other signals.

A further advantage of certain aspects of the present invention is that it provides modulation of treatment magnitude to compensate for predictable fluctuations in symptomatology and cognitive and neuromotor functionality. Such fluctuations include those due to, for example, the circadian cycle, postprandial and nutritional changes in symptomatology, and variations in plasma levels of pharmacologic agents.

A further advantage of certain aspects of the present invention is that it is responsive to patient symptomatology, as tremor typically abates during sleep. This overcomes the above-noted problems of patient inability to hold a magnet in a stable manner over the implanted electronics module and the resulting problem of not being able to turn their stimulators on in the morning without assistance.

A still further advantage of certain aspects of the present invention is that it provides prediction of future symptomatology, cognitive and neuromotor functionality, and treatment magnitude requirements. Such predictions may be based on preset, learned and real-time sensed parameters as well as input from the patient, physician or other person or system.

A still further advantage of certain aspects of the present invention is that it optimizes the efficiency of energy used in the treatment given to the patient. Stimulation intensity may be minimized to provide the level of treatment magnitude necessary to control disease symptoms to a satisfactory level without extending additional energy delivering unnecessary overtreatment.

Further features and advantages of the present invention, as well as the structure and operation of various embodiments of the present invention, are described in detail below with reference to the accompanying drawings.

BRIEF DESCRIPTION OF THE DRAWINGS

The present invention is described with reference to the accompanying drawings. In the drawings, like reference numerals indicate identical or functionally similar elements.

DETAILED DESCRIPTION

Figure 1:
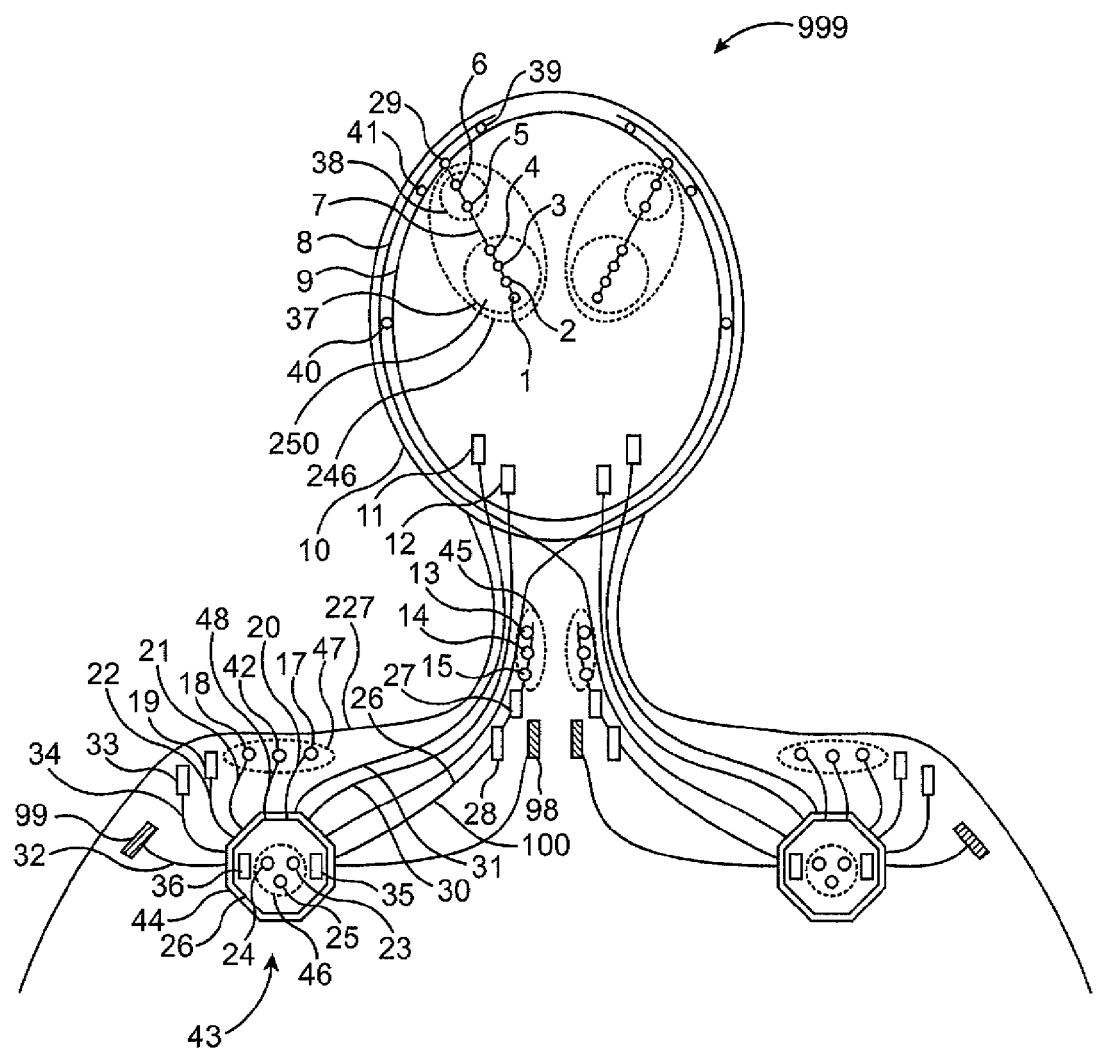
FIG. 1 is a schematic diagram of one embodiment of the present invention implanted bilaterally in a human patient.

FIG. 1 is a schematic diagram of one embodiment of the intracranial stimulator of the present invention implanted bilaterally in a human patient. In the embodiment illustrated in FIG. 1, two neurological control systems 999 are shown implanted bilaterally. Each system 999 includes a stimulating and recording unit 26 and one or more intracranial components described below. As described in this illustrative embodiment, the intracranial components preferably include a stimulating electrode array 37. However, it should become apparent to those of ordinary skill in the relevant art after reading the present disclosure that the stimulating electrodes may also be extracranial; that is, attached to a peripheral nerve in addition to or in place of being located within the cranium. As shown in FIG. 1, stimulating and recording unit 26 of each neurological control system 999 is preferably implanted contralateral to the intracranial components of the device.

As one skilled in the relevant art would find apparent from the following description, the configuration illustrated in FIG. 1 is just one example of the present invention. Many other configurations are contemplated. For example, in alternative embodiments of the present invention, the stimulating and recording unit 26 is implanted ipsilateral or bilateral to the intracranial components. It should also be understood that the stimulating and recording unit 26 can receive ipsilateral, contralateral or bilateral inputs from sensors and deliver ipsilateral, contralateral, or bilateral outputs to a single or a plurality of intracranial stimulating electrode arrays 37. Preferably, these inputs are direct or preamplified signals from at least one of EMG electrode array 50, EEG electrode array 51, Accelerometer Array 52, Acoustic Transducer Array 53, Peripheral Nerve Electrode Array 54, and Intracranial Recording Electrode Array 38. The signals input from these sensors will be referred to herein as "sensory input modalities" 247. The outputs include but are not limited to one or more stimulating current signals or stimulating voltage signals to Intracranial Stimulating Electrode Array 37.

In the embodiment illustrated in FIG. 1, the two unilateral systems 26 are shown to receive sensory inputs from the side contralateral as well as the intracranial stimulating electrode arrays 37. In the illustrative embodiment, systems 26 also receive sensory inputs from intracranial recording electrode arrays 38. As will become apparent from the following description, intracranial recording electrode arrays 38 may provide valuable feedback information.

It should be understood that this depiction is for simplicity only, and that any combination of ipsilateral, contralateral or bilateral combination of each of the multiple sensory input modalities and multiple stimulation output channels may be employed. In addition, stimulating and recording units 26 may be a single device, two communicating devices, or two independent devices. Accordingly, these and other configurations are considered to be within the scope of the present invention. It is anticipated that stimulating and recording units 26, if implemented as distinct units, would likely be implanted in separate procedures (soon after clinical introduction) to minimize the likelihood of drastic neurological complications.

In the exemplary embodiment illustrated in FIG. 1, the intracranial stimulating electrode array 37 includes a plurality of intracranial stimulating electrodes 1, 2, 3 and 4. Array 37 may, of course, have more or fewer electrodes than that depicted in FIG. 1. These intracranial stimulating electrodes 1–4 may be used to provide stimulation to a predetermined nervous system component. The electrical stimulation provided by the intracranial stimulating electrodes 1–4 may be excitatory or inhibitory, and this may vary in a manner which is preprogrammed, varied in real-time, computed in advance using a predictive algorithm, or determined using another technique now or latter developed.

The intracranial recording electrode arrays 38 includes intracranial recording electrodes 5 and 6. In accordance with one embodiment of the present invention, the intracranial recording electrodes 5, 6 are used to record cortical activity as a measure of response to treatment and as a predictor of impeding treatment magnitude requirements. In the illustrative embodiment, intracranial recording electrodes 5 and 6 are depicted in a location superficial to the intracranial stimulating electrodes 1–4. However, this positioning may be reversed or the intracranial stimulating electrodes 1–4 and intracranial recording electrodes 5 and 6 may be interspersed in alternative embodiments. For example, these electrodes may be placed in at least one of motor cortex, premotor cortex, supplementary motor cortex, other motor cortical areas, somatosensory cortex, other sensory cortical areas, Wernicke's area, Broca's area, other cortical region, other intracranial region, and other extracranial region.

In the illustrative embodiment, an intracranial catheter 7 is provided to mechanically support and facilitate electrical connection between intracranial and extracranial structures. In this embodiment, intracranial catheter 7 contains one or more wires connecting extracranial stimulating and recording circuit 26 to the intracranial electrodes, including but not limited to, intracranial stimulating electrodes 1–4 and intracranial recording electrodes 5, 6. The wires contained within intracranial catheter 7 transmit stimulating electrode output signal (SEOS) to intracranial stimulating electrode array 37. Such wires additionally transmit stimulating electrode input signal (SEIS) and recording electrode input signal (REIS), from intracranial stimulating electrode array 37 and intracranial recording electrode array 38 respectively, to stimulating and recording circuit 26.

Stimulating and recording circuit 26 is protected within a circuit enclosure 44. Circuit enclosure 44 and contained components, including stimulating and recording circuit 26 comprise stimulating and recording unit 43. It should be understood that more or fewer of either type of electrode as well as additional electrode types and locations may be incorporated or substituted without departing from the spirit of the present invention. Furthermore, stimulating and recording circuit 26 can be placed extra cranially in a subclavian pocket as shown in FIG. 1, or it may be placed in other extracranial or intracranial locations.

Connecting cable 8 generally provides electrical connection between intracranial or intracranial locations. A set of electrical wires provides the means for communication between the intracranial and extracranial components; however, it should be understood that alternate systems and techniques such as radio frequency links, optical (including infrared) links with transcranial optical windows, magnetic links, and electrical links using the body components as conductors, may be used without departing from the present invention. Specifically, in the illustrative embodiment, connecting cable 8 provides electrical connection between intracranial components 246 and stimulating and recording circuit 26. In embodiments wherein stimulating and recording circuit 26 has an intracranial location, connecting cable 8 would likely be entirely intracranial. Alternatively, connecting in embodiments wherein stimulating and recording circuit 26 is implanted under scalp 10 or within or attached to calvarum 9, connecting cable 8 may be confined entirely to subcutaneous region under the scalp 10.

A catheter anchor 29 provides mechanical connection between intracranial catheter 7 and calvarum 9. Catheter anchor 29 is preferably deep to the overlying scalp 10. Such a subcutaneous connecting cable 8 provides electrical connection between intracranial electrodes 246 and stimulating and recording circuit 26. Cable 8 may also connect any other sensors, including but not limited to any of sensory input modalities 247, or other stimulating electrodes, medication dispensers, or actuators with stimulating and recording circuit 26.

Sensory feedback is provided to recording and stimulating unit 26 from a multiplicity of sensors, collectively referred to as sensory input modalities 247. Intracranial recording electrode array 38, previously described, is intracranial in location. Additional sensors, most of which are located extracranially in the preferred embodiment, comprise the remainder of sensory input modalities 247. Sensory input modalities 247 provide information to stimulating and recording unit 26. As will be described in greater detail below, such information is processed by stimulating and recording unit 26 to deduce the disease state and progression and its response to therapy.

In one embodiment of the invention, a head-mounted acoustic sensor 11 is used to monitor any number of vibratory characteristics such as high frequency head vibration, muscle vibration, and/or speech production. Head-mounted acoustic sensor 11 is connected to stimulating and recording circuit 26 with an acoustic sensor connecting cable 30.

A head-mounted accelerometer 12 is implemented in certain embodiments of the present invention to monitor head movement and position with respect to gravity. Head-mounted accelerometer 12 may be mounted to any structure or structures that enables it to accurately sense a desired movement. Such structures include, for example, the skull base, calvarum, clavicle, mandible, extraocular structures, soft tissues and vertebrae. Head-mounted accelerometer 12 is connected to stimulating and recording circuit 26 with an accelerometer connecting cable 31.

A proximal electromyography (EMG) electrode array 45 is also included in certain preferred embodiments of the invention. Proximal EMG electrode array 45 includes a positive proximal EMG electrode 13, a reference proximal EMG electrode 14, and a negative proximal EMG electrode 15. As one skilled in the relevant art would find apparent, proximal EMG electrode array 45 may include any number of type of electrodes. Proximal EMG electrode array 45 is implanted in or adjacent to muscle tissue. In the embodiment illustrated in FIG. 1, proximal EMG electrode array 45 is shown implanted within the neck of the human patient. However, it should be understood that this location is illustrative only and that proximal EMG electrode array 45 may be implanted in or adjacent to any muscle without departing from the spirit of the present invention.

A proximal acoustic sensor 27 may also be implemented in the present invention. Proximal acoustic sensor 27 senses muscle vibration and may be used to augment, supplement or replace EMG recording. Also, a proximal accelerometer 28 may be used to sense movement, including tremor and voluntary activity, and orientation with respect to gravity. Proximal connecting cable 16 provides electrical connection from the proximal EMG electrodes 14 and 15, proximal acoustic sensor 27, and proximal accelerometer 28 to stimulating and recording circuit 26. In the illustrative embodiment, these sensors are shown connected to a common proximal connecting cable 16. However, in alternative embodiments, this configuration may include the use of multiple connecting cables or implement other types of communication media without departing from the present invention. It should also be understood from the preceding description that the number of each type of sensor may also be increased or decreased, some sensor types may be eliminated, and other sensor types may be included without departing from the spirit of the present invention.

A distal EMG electrode array 47 may also be included in certain embodiments of the present invention. In such embodiments, distal EMG electrode array 47 typically includes a positive distal EMG electrode 17, a reference distal EMG electrode 42, and a negative distal EMG electrode 18. Positive distal EMG electrode 17 is connected to stimulating and recording circuit 26 by positive distal EMG connecting cable 20. Negative distal EMG electrode 18 is connected to stimulating and recording circuit 26 by negative distal EMG connecting cable 21. Reference distal EMG electrode 42 is connected to stimulating and recording circuit 26 by reference distal EMG connecting cable 48.

In other embodiments, a distal acoustic sensor 19 is connected to stimulating and recording circuit 26 by distal acoustic connecting cable 22. Distal accelerometer 33 is connected to stimulating and recording circuit 26 by distal accelerometer connecting cable 34. Distal accelerometer 33 is connected to stimulating and recording circuit 26 by distal accelerometer connecting cable 34.

In the embodiment illustrated in FIG. 1, distal EMG electrode array 47, distal acoustic sensor 19, and distal accelerometer 33 are shown located in the shoulder region. However, the distal EMG electrode array 47 may be located in other locations, including, for example, the masseter, temporalis, sternocleidomastoid, other portion of the head and neck, pectoralis, torso, abdomen, upper extremities, lower extremities, and other locations. The number of each type of sensor may be increased or decreased, some sensor types may be eliminated, and other sensor types may be included without departing from the spirit of the present invention.

An enclosure-mounted EMG electrode array 46 is illustrated in FIG. 1. Enclosure-mounted EMG electrode array 46 includes enclosure-mounted positive EMG electrode 23, enclosure-mounted negative EMG electrode 24 and enclosure-mounted reference EMG electrode 25, all of which are attached to the circuit enclosure 44 that encloses stimulating and recording unit 26. The circuit enclosure 44 is preferably included to provide robustness against potential lead entanglement and fracture. In one particular embodiment, circuit enclosure 44 is constructed of titanium and epoxy, or other single or combination of bio-compatible materials. Enclosure-mounted acoustic sensor 35 and enclosure-mounted accelerometer 36 are mounted to stimulating and recording unit 43. The number of each type of sensor may be increased or decreased, their locations changed, some sensor types eliminated, and other sensor types included without departing from the spirit of the present invention.

In the embodiment illustrated in FIG. 1, EEG electrodes 39, 40, 41 are provided. The EEG electrodes may be mounted directly to connecting cable 8 or may be connected via intermediate cables. Any one of the numerous standard and new electrode configurations, or montages, may be employed in EEG electrodes 39–41 without departing from the present invention.

In one embodiment, a proximal peripheral nerve electrode array 98 is connected to stimulating and recording circuit 26 by proximal peripheral nerve electrode array connecting cable 100. Proximal peripheral nerve electrode array 98 is shown located in the neck region. In this location proximal peripheral nerve electrode array 98 can interface with the vagus nerve, spinal accessory nerve, or nerve arising from cervical roots.

A distal peripheral nerve electrode array 99 is connected to stimulating and recording circuit 26 by distal peripheral nerve electrode array connecting cable 32. Distal peripheral nerve electrode array 99 is shown located by the proximal arm, in position to interface with the brachial plexus or proximal arm nerve. One or more of these peripheral nerve electrode arrays may be implanted in these or other locations, including but not limited to the head, cranial nerves, neck, torso, abdomen, upper extremities, and lower extremities, without departing from the present invention.

In one preferred embodiment, the peripheral nerve electrode arrays are each comprised of three epineural platinum-iridium ring electrodes, each in with an internal diameter approximately 30% larger than that of the epineurium, longitudinally spaced along the nerve. Electrodes of differing dimensions and geometries and constructed from different materials may alternatively be used without departing from the present invention. Alternative electrode configurations include but are not limited to epineural, intrafascicular, or other intraneural electrodes; and materials include but are not limited to platinum, gold, stainless steel, carbon, and other element or alloy.

Figure 2:
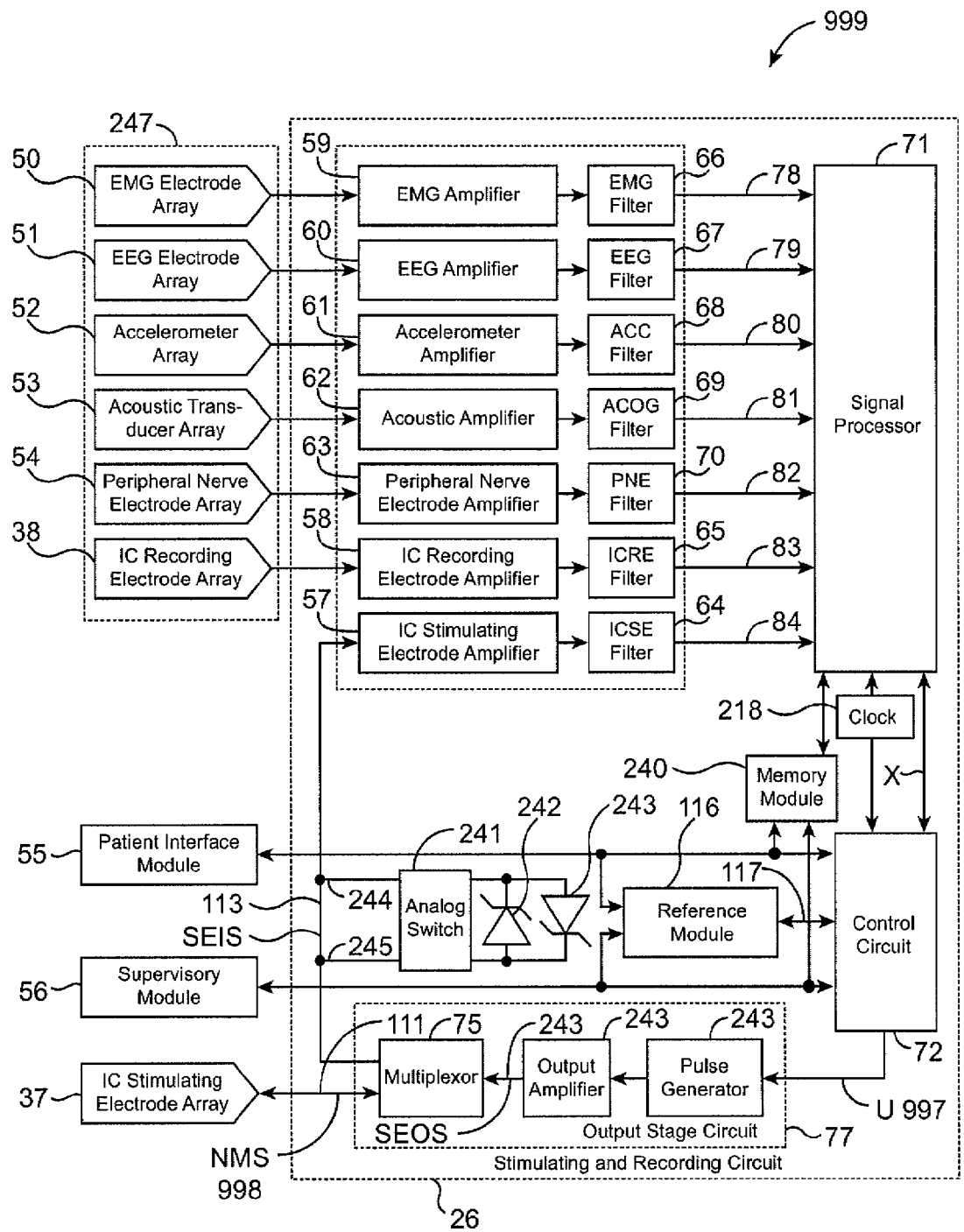
FIG. 2 is an architectural block diagram of one embodiment of the neurological control system of the present invention.

FIG. 2 is an architectural block diagram of one embodiment of the neurological control system 999 of the present invention for modulating the activity of at least one nervous system component in a patient. As used herein, a nervous system component includes any component or structure comprising an entirety or portion of the nervous system, or any structure interfaced thereto. In one preferred embodiment, the nervous system component that is controlled by the present invention includes the globus pallidus internus. In another preferred embodiment, the controlled nervous system component is the subthalamic nucleus.

The neurological control system 999 includes one or more implantable components 249 including a plurality of sensors each configured to sense a particular characteristic indicative of a neurological or psychiatric condition. One or more intracranial (IC) stimulating electrodes in an IC stimulating electrode array 37 delivers a neural modulation signal to the same or other nervous system component as that being monitored by the system 26. One or more sensors 38, 51, 52, 53, and 54 sense the occurrence of neural responses to the neural modulation signals. Stimulating and recording unit 26 generates the neural modulation signal based on the neural response sensed by the sensors.

The neurological control system 999 preferably also includes a patient interface module 55 and a supervisory module 56. A control circuit 72 (described below) is communicably coupled to the patient interface module 55 and receives signal inputs from and provides signal outputs to patient interface module 55 and supervisory module 56. In one preferred embodiment, patient interface module 55 and supervisory module 56 remain external to the body of the patient. However either of these devices may be connected via percutaneous leads or be partially or totally implanted without departing from the present invention.

Patient interface module 55 and supervisory module 56 facilitate adjustment of control parameters, monitoring of disease state, monitoring of response to therapy, monitoring of stimulating and recording circuit 26, monitoring of impedance and other characteristics of intracranial stimulating electrode array 37, monitoring of physiologic parameters, monitoring of vital signs, monitoring of any other characteristic or function of components of the present invention, including but not limited to the stimulating and recording circuit 26, stimulating and recording unit 43, circuit enclosure 44, EMG electrode array 50, EEG electrode array 51, accelerometer array 52, acoustic transducer array 53, peripheral nerve electrode array 54, and intracranial recording electrode array 38. Such monitoring and adjustment is accomplished through the use of any well known bi-directional communication between control circuit 72 and supervisory module 56. In one preferred embodiment, a radio frequency link is employed. In alternative embodiments, other communication technologies, including but not limited to optical, percutaneous, or electromagnetic, may be used.

In one preferred embodiment, patient interface module 55 and supervisory module 56 are placed adjacent to the patients garments overlying the implanted stimulating and recording unit 43. When neurological control system 999 is turned on in this position, a communications handshaking protocol is executed. Communication handshaking routines are known to those or ordinary skill in the art, and they enable establishment of a communication rate and protocol and facilitate mutual identification of devices. Patient interface module 55 automatically downloads parameters from stimulating and recording circuit 26 and stores values of such parameters in a memory. When the transfer of these parameter values is complete, patient interface module 55 emits a audible signal such as a series of beeps, and the patient turns off patient interface module 55 and removes it from its position overlying the implanted stimulating and recording unit 43. Parameter values may then be retrieved by the patient by a routine including but not limited to a menu driven interface, and the values may be transmitted via telephone conversation or other communication method to a health care professional. Supervisory module 56 operates in the same manner with one addition; a step is provided during which the health care professional may upload parameters to stimulating and recording circuit 26 to alter its function including by means of changing parameters including but not limited to control laws gains and thresholds, filter parameters, signal processing parameters, stimulation waveform modes (including at least one of current regulated, voltage regulated, frequency regulated, or pulse width regulated), and stimulation waveform parameters.

Control laws, well known to those of ordinary skill in the field of control theory, are defined by a set of parameters specific to the particular control law. Common parameters include preset gains, threshold levels, saturation amplitudes, sampling rates, and others. Adaptive controllers change in response to the behavior of the system being controlled; as such, in addition to preset parameters, adaptive controllers possess a set of varying parameters. These varying parameters contain information indicative of the behavior of the system being controlled; downloading of these parameters provides one set of measures of the disease state and its response to therapy.

Such monitoring includes observation of time history of disease state, stimulation parameters, response to therapy, and control law parameters, including time-varying adaptive controller parameters. Such adjustments includes modification of actual stimulation parameters and allowable ranges thereof, including but not limited to pulse width, pulse amplitude, interpulse interval, pulse frequency, number of pulses per burst frequency. Adjustments can further include modification of actual control law parameters and allowable ranges thereof, including but not limited to gains, thresholds and sampling rates of said stimulation waveforms. Signal processor 71 contains signal processor modules for each of the sensory input modalities 247. Signal processing algorithms for each of the said sensory input modalities 247 may be independent. Additionally, signal processing algorithms the said sensory input modalities 247 may be coupled, such that the processing of one of the sensory input modalities 247 is dependent on another of the sensory input modalities 247. Adjustments may additionally include modification of actual signal processor parameters and allowable ranges thereof, including but not limited to gains, filter cutoff frequencies, filter time constants, thresholds, and sampling rates. In a preferred embodiment, the stimulation and control law parameters are stored in at least one of random access memory and central processing unit registers (not shown).

It is anticipated that patient interface module 55 is to be used by the patient, a family member or associate, or home health care personnel to monitor the functions and performance of neurological control system 999. In such an embodiment, the use of the patient interface module 55 is restricted to monitoring operations; adjustment of stimulation and control parameters is not enabled. However, adjustment of all or a subset of stimulation and control parameters (described below) may be facilitated by patient interface module 55 without departing from the present invention. Supervisory module 56, on the other hand, is used by a physician or other health care personnel to monitor function and performance of neurological control system 999 and to adjust stimulation and control parameters. Control parameters controlled by patient interface module 55 and supervisory module 56 include allowable stimulation magnitude range, such as maximum combination of stimulation voltage, current, pulse width, pulse frequency, train frequency, pulse train count, pulse train duration. Control parameters may also include variables and constants used to define control laws implemented in control circuit 72. Such control parameters include, but are not limited to, control law gains 197–203, and other parameters for control laws, including but not limited to proportional controller 230, differential controller 204, integral controller 205, nonlinear controller 206, adaptive controller 207, sliding controller 208, model reference controller 209, and other controllers. In addition, amplitudes for other controller parameters, including but not limited to amplitudes for controller weights 210–216 may be set by supervisory module 56. Additionally, the parameters specifying the maximum amplitudes, or saturation values, may be set by supervisory module 56. Control circuit 72 (FIG. 12) will be described in detail below.

The majority of the computation accomplished by stimulating and recording circuit 26 is performed in signal conditioning unit 76, signal processor 71, and control circuit 72; the algorithms and behavior of which are determined by corresponding sets of control parameters, of which some may be set by the supervisory module 56 and a typically more restricted set by patient interface module 55. In one embodiment, control parameters further includes signal conditioning parameters. Signal conditioning parameters may include, for example, amplifier gains, filter gains and bandwidths, threshold values, and other parameters. In certain embodiments, control parameters additionally include signal processing parameters, including envelope determinator gains and time constants, filter passbands, filter gains, threshold values, integrator gains, analyzer parameters, disease state estimator parameters, artifact rejecter thresholds, envelope determinator time constants, rectifier parameters, spectral analyzer parameters and timer parameters.

In the illustrative embodiment described herein, control parameters further include spike detector 188 (FIG. 9) parameters, spike characterizer 189 (FIG. 9) parameters, spike analyzer 190 (FIG. 9) parameters, spectral energy characterizer 192 (FIG. 9) parameters, spectral energy analyzer 193 (FIG. 9) parameters, aggregate disease state estimator 195 (FIG. 10) parameters.

In accordance with the present invention, tremor are quantified and monitored by any sensors over time as indicators of disease state. Such sensors include but are not limited to EMG electrode array 50, EEG electrode array 51, accelerometer array 52, acoustic transducer array 53, peripheral nerve electrode array 54, intracranial recording electrode array 38, and intracranial stimulating electrode array 37. In one particular embodiment, the sensed tremor characteristics include, but are not limited to, magnitude, frequency, duration and frequency of occurrence of tremors. Changes in these and other parameters are compared to current levels of, and changes in, treatment parameters. These changes are then used by aggregate disease state estimator 195 to estimate the response to therapy as functions of various electrical stimulation treatment parameters. Electrical stimulation treatment parameters are adjusted by control circuit 72 in real-time to provide optimal control of disease state.

Modulation parameters are optimized to achieve at least one of minimization of disease state, minimization of symptoms of disease, minimization of stimulation magnitude, minimization of side effects, and any constant or time-varying weighted combination of these. Patient interface module 55 and supervisory module 56 also preferably monitor the function and operation of other components of neurological control system 999, including stimulating and recording unit 26 and implanted components 249.

Stimulating and recording unit 26 receives and processes signals generated by implanted components 249 to provide conditioned signals 78–84 to a signal processor 71. For each type of implanted components 249 coupled to stimulating and recording unit 26, signal conditioning circuit 76 preferably includes an associated amplifier and filter. Each amplifier and associated filter is configured to receive and process the signal generated by the associated one of the set of sensors 38, 51, 52, 53, and 54.

In the illustrative embodiment, implanted components 249 include an electromyography (EMG) electrode array 50 which generate EMG signals. Preferably, EMG electrode array 50 comprises of all EMG electrodes implemented in the particular embodiment of the present invention. These include, in the exemplary embodiment illustrated in FIG. 1, proximal EMG electrode array 45, enclosure-mounted EMG electrode array 46 and distal EMG electrode array 47. Array 50 may also include, for example, EMG electrodes implanted in the head or other location, and surface EMG electrodes.

Implanted components 249 also include an electroencephalography (EEG) electrode array 51 which generate EEG signals and accelerometer array 52 which generates acceleration signals. EEG electrodes 39, 40, 41 illustrated in FIG. 1 are representative of EEG electrode array 51. EEG electrodes 39–41 may be mounted directly to connecting cable 8 or connected via intermediate cables. EEG electrode array 51 may include more or fewer elements than EEG electrodes 39–41 depicted; and any of numerous standard and new electrode configurations, or montages, may be employed without departing from the present invention.

Accelerometer array 52, which produces well-known acceleration signals, preferably includes all accelerometers implemented in the patient associated with the present invention. For example, in the embodiment illustrated in FIG. 1, accelerometer array 52 includes head-mounted accelerometer 12, proximal accelerometer 28, enclosure-mounted accelerometer 36 and distal accelerometer 33. Accelerometer array 52 may include more or fewer accelerometers than these accelerometers, and accelerometers of any types and locations may be employed without departing from the present invention.

Acoustic transducer array 53 includes all acoustic sensors utilized by the present invention. In the exemplary embodiment illustrated in FIG. 1, acoustic transducer array 53, includes head-mounted acoustic sensor 11, proximal acoustic sensor 27, enclosure-mounted acoustic sensor 35 and distal acoustic sensor 19. It should be understood that acoustic transducer array 53 may include more or fewer elements than said acoustic sensors listed above; and any of numerous acoustic sensor types and locations may be employed without departing from the present invention.

Peripheral nerve electrode array 54 generates peripheral neural signals, including but not limited to efferent and afferent axonal signals. Preferably, peripheral nerve electrode array 54 includes all peripheral nerve electrodes implemented in present invention. For example, in the illustrative embodiment illustrated in FIG. 1, peripheral nerve electrode array 54 includes proximal peripheral nerve electrode array 98 and distal peripheral nerve electrode array 99. The single or plurality of individual peripheral nerve electrode arrays which comprise peripheral nerve electrode array 54 may be implanted in the illustrated or other locations, as noted above.

Intracranial (IC) recording electrode array 38 generates central neural signals, including but not limited to cortical, white matter, and deep brain nuclear signals. Neural activity to be sensed includes but is not limited to that found in the primary motor cortex, premotor cortex, supplementary motor cortex, somatosensory cortex, white matter tracts associated with these cortical areas, the globus pallidus internal segment, the globus pallidus external segment, the caudate, the putamen, and other cortical and subcortical areas. As one of ordinary skill in the relevant art will find apparent, the present invention may include additional or different types of sensors that sense neural responses for the type and particular patient. Such sensors generate sensed signals that may be conditioned to generate conditioned signals, as described below. One example of the placement of these electrodes is described above with reference to the embodiment illustrated in FIG. 1. Many others are contemplated by the present invention.

As noted, for each of the different types of sensors included in implanted components 249, signal conditioning circuit 76 includes an associated amplifier and filter in the illustrative embodiment. Accordingly, signal conditioning circuit 76 includes an EMG amplifier 59 and filter 66, each constructed and arranged to amplify and filter, respectively, the EMG signals received from EMG electrode array 50. Similarly, signal conditioning circuit 76 also includes an EEG amplifier 60 and filter 67, accelerometer (ACC) amplifier 61 and filter 68, acoustic (ACO) amplifier 62 and filter 69, peripheral nerve electrode (PNE) amplifier 63 and filter 70 and intracranial (IC) recording electrode (ICRE) amplifier 58 and filter 65.

Simplifiers 57–63 may be single or multi-channel amplifiers depending upon the number of electrodes with which it interfaces. In one preferred embodiment, amplifiers 57–63 are physically located in the same enclosure as filters 64–70; that is, in a single signal conditioning circuit 76. Preferably, signal conditioning circuit 76 is physically contained within stimulating and recording unit 102. However, amplifiers 57–63 may be located separately from stimulating recording unit 102. For example, amplifiers 57–63 may be affixed to or situated proximate to their associated electrode arrays 38, 50–54. This arrangement facilitates the preamplification of the associated signals generated by the associated electrode arrays 38, 50–54, increasing the signal-to-noise ratio of the signals. Amplifiers 57–63 may be any known voltage amplifier now or later developed suitable for amplifying the particular signals generated by their associated electrodes.

As noted, the amplified signals are passed to their associated filters 64–70 as shown in FIG. 2. As with amplifiers 57–59, filters 64–70 may be physically separate from or incorporated into signal conditioning circuit 76 and stimulating and recording unit 26. In one preferred embodiment, filters 64–70 are low pass filters having a cut-off frequency of, for example, 3,000 Hz. In alternative embodiments, filters 64–70 may include a notch filter to remove, for example, 60 Hz noise, or other types of filters appropriate for the type of signals generated by the associated sensors 38, 51, 52, 53, and 54. Selection of the appropriate frequencies for the cut-off and notch filter frequencies is considered to be well known in the relevant art and within the scope of the present invention. Filters 66–70, 65 and 64 generate conditioned sensed signals 84, 83 and 78–82, respectively.

Signal processor 71 processes the conditioned sensed neural response signals 78–84 generated by signal conditioning circuit 76 in accordance with the present invention to determine neural system states. Signal processor 71 generally performs well known filtering operations in the time and frequency domains. In one preferred embodiment, the neural system states include one or more physiologic or disease states. Signal processor 71, which can be implemented in a fast microprocessor, a DSP (digital signal processor) chip, or as analog circuitry, for example, is described in detail below.

Control circuit 72, responsive to the signal processor 71, patient interface module 55 and supervisory module 56, adjusts the magnitude of a neural modulation signal in response to the sensed neural response. Signal processor 71 extracts relevant information from the sensed condition signals, and control circuit 72 uses this extracted information in the calculation of an output neuromodulation signal (NMS) 998. Neuromodulation signal 998 subsequently travels along stimulator output path 111 to IC stimulating electrode array 37. In one embodiment, control circuit 72 is a state machine, utilizing current and past system behavior in the calculation of a control signal. In an alternative embodiment, control circuit 72 includes an embedded microprocessor to process nonlinear control laws. Alternative embodiments of the control circuit 72 appropriate for the particular application may be also be used.

Control circuit 72 receives control law selection information, control law parameter information, stimulation waveform parameter range information, stimulation modulation mode, output stage regulation mode, and medication dose and timing information from patient interface module 55 and supervisory module 56. The waveform parameter or parameters which are modulated by control law output signal U 997 are determined by the stimulation modulation mode; these parameters include but are not limited to pulse amplitude, pulse width, pulse frequency, pulses per burst, and burst frequency. Selection between regulation of pulse voltage or pulse current as the regulated pulse amplitude is determined by the output stage regulation mode.

Control circuit 72 provides stimulation waveform parameter history information, disease state history information, control law state variable history information, control law error history information, control law input variable history information, control law output variable history information, stimulating electrode impedance history information, sensory input history information, battery voltage history information, and power consumption history information to patient interface module 55 and supervisory module 56.

Provision of stimulating electrode impedance history information allows monitoring of stimulating electrode performance and functionality. If an electrode is determined to be fractured, shorted, or encapsulated by fibrotic tissue, any of various control law parameters, output stage parameters, and waveform range parameters may be adjusted to allow compensation for these changes. Additionally, the Neuromodulation Signal (NMS) 998 may be delivered to different sets of electrodes to insure that it reaches neural tissue 250. Sensory input history information allows evaluation of validity of any given sensory input. This is useful in determining the functionality of a given sensor and serves as an indicator for sensor replacement or adjustment of the signal processing parameters or algorithm or the control law parameters or algorithm to continue to generate reliable disease state estimate signals X and control law outputs U despite the loss of any particular individual or set of sensory signals.

Signal processor 71 receives amplifier gain setting information, filter parameter information, weighting information, and disease state estimator parameter and algorithm information from patient interface module 55 and supervisory module 56. The function and operation of patient interface module 55 and supervisory module 56 are described above. As noted, patient interface module 55 may be used by the patient or home health care personnel to monitor disease state, stimulation parameters, and response to therapy. Limited adjustment of stimulation parameters and ranges is facilitated. Patient interface module 55 may be used by the patient or home health care personnel to provide information to the physician, avoiding the need for an office visit for the obtainment of said information.

Patient information module 55 queries signal processor 71 for present and time histories of monitored values. Time histories of selected variables in signal processor 71 and control circuit 72 are stored in memory module 240 for subsequent retrieval by patient interface module 55 and supervisory module 56. Selected variables include but are not limited to disease state, tremor frequency, tremor magnitude, EMG magnitude, EMG frequency spectra (EMG magnitude within frequency ranges), and acceleration of limb, head, mandible, or torso. Selected variables may also include disease state, frequency spectra of limb, torso, and head movements, as determined by EMG and accelerometer signals.

Stimulating and recording unit 26 also includes an output stage circuit 77. Output stage circuit 77 takes for an input the control law output signal U, which may be comprised of a single or multiplicity of channels or signals, from control circuit 72. This control law output signal U 997 modulates the magnitude of the sequence of waveforms comprising the desired output neuromodulation signal (NMS$_D$) which is produced by output stage circuit 77 and delivered via intracranial stimulating electrode array 37 to neural tissue 250.

Output stage circuit 77 generates a neuromodulation signal (NMS$_D$) 998 with a magnitude specified by control law output signal U 997 received from control circuit 72. In one preferred embodiment, the waveform parameter of the desired output neuromodulation signal (NMS$_D$) which is modulated by control law output signal U is the stimulation current magnitude. The capability to specifically modulate the stimulation current confers efficacy resistance to perturbations or changes in electrode impedance. Presently implanted systems suffer from a decline in efficacy which results from an increase in electrode impedance which accompanies the normal tissue response to a foreign body, that is fibrotic encapsulation of the electrode. In this design taught in the present invention, a the magnitude of the current delivered to the neural tissue 250 will not vary as the electrode becomes encapsulated with fibrotic tissue or its impedance otherwise changes over time. A further advantage conferred by current modulation is the ability to monitor electrode impedance. If a current-modulated waveform, preferably a sinusoid, is delivered to the electrodes, and the resultant voltage potential waveform is concurrently monitored, the relative magnitudes and phase shifts of these waveforms may be computed. From these magnitudes and phases, the complex impedance and hence the resistive and capacitive components of the electrode impedance may be calculated.

In an alternative embodiment, the waveform parameter of the desired output neuromodulation signal (NMS$_D$) which is modulated by control law output signal U 997 is the stimulation voltage magnitude. This design would not enjoy the independence of the stimulation current and efficacy from impedance variation enjoyed by the embodiment described above. If fibrosis was uneven around the surface of the electrode, this embodiment would avoid potentially undesirably large current densities along narrow tracts of remaining low resistance unfibrosed regions of neural tissue 250.

Alternatively, regulation of stimulus pulse width may be desired. In certain circuit implementations, the available resolution or bits for specifying the magnitude of pulse width may be greater than that for specifying the pulse voltage or current. In such a case, if finer control of the magnitude of Neuromodulation signal (NMS) 998 is desired than is provided by the control of pulse current or pulse voltage, then it may be desirable to modulate the pulse width. Furthermore, the spatial neuron recruitment characteristics of a pulse width modulated neuromodulation signal (NMS) 998 may provide a more linear, predictable, or controllable response than that obtained with current or voltage modulation. Selection between regulation of pulse voltage, pulse current, or pulse width as the regulated pulse amplitude parameter is determined by the output stage regulation mode, which may be set using supervisory module 56. In alternative embodiments, the modulation of pulse frequency and the modulation of the number of pulses per burst are regulated. As one of ordinary skill in the relevant art would find apparent. Other such characteristics may be regulated in addition to or instead of the ones noted above.

Output stage circuit 77 includes a pulse generator 73, an output amplifier 74 and a multiplexor 75. Pulse generator 73 generates one or more stimulus waveforms, each of which is characterized by several parameters, including but not limited to pulse amplitude, pulse width, pulse frequency, number of pulses per burst, and burst frequency. As noted above, pulse amplitude may comprise pulse voltage or pulse current. Preferably, each of these parameters may be independently varied, as specified by control law output signal U 997 generated by control circuit 72. As noted, the stimulus waveforms comprising the neuromodulation signal (NMS) generated by output stage circuit 77 are applied to patient through intracranial (IC) stimulating electrode array 37. Pulse generator 73 generates a single waveform when single channel stimulation is to be used, and a plurality of waveforms when multiple channel stimulation is to be used. It may generate monophasic or biphasic waveforms.

In one preferred embodiment, charge balanced biphasic waveforms are produced. Those skilled in the art are aware that the net charge contained in a given pulse is given by the time integral of the stimulus current over the duration of the pulse. In a biphasic configuration, a pair of pulses of opposite polarity is generated, and the pulse current amplitude and pulse width are chosen such that the charge amplitude is equal in magnitude and opposite in polarity. In some cases, it is desirable for the pulses comprising the biphasic pulse pair to have different amplitudes; in this case, the pulse widths are chosen to insure equal and opposite charges so the pulse par introduces zero net charge to the neural tissue 250. The capability to deliver pulse pairs with balanced charges is yet a further advantage conferred by the current regulation mode described above.

Even though the waveform parameters of the pulse pairs are calculated to deliver a zero net charge, in practice, noise and precision limitations in computation and resolution limitations and nonlinearities in the digital to analog conversion and amplification stages may result in slight imbalances in the pulse pair charges. Over time, this can result in the delivery of a substantial accumulated net charge to the neural tissue. To eliminate this potential for net charge delivery to neural tissue, a direct current (DC) blocking capacitor is employed. This is a technique that is well known to those or ordinary skill in the art. In one preferred embodiment, a DC blocking capacitor is included within multiplexor 75 in series with stimulator output path 111.

Typically, multi-channel stimulation is used in the case of bilateral stimulation. Since the disease progression is typically asymmetrical, and the normal motor control systems governing movement on the left and right side of the body are also highly independent of each other, the delivery of treatment to the left and right sides of the body should be controlled separately. This represents one need for a multiple channel neuromodulation signal (NMS) 998. Multichannel stimulation is also expected to be beneficial in treating patients with variable involvement of different limbs. For example, the magnitude neuromodulation of a portion of the globus pallidus required to achieve optimal controls of arm tremor may be different from the optimal level of neuromodulation of separate portion of the globus pallidus to achieve optimal control of leg tremor. In this case, separate electrodes or electrode pairs are required to deliver optimal levels of neuromodulation to control tremor in these two regions of the body. Correspondingly, these separate electrodes or electrode pairs will be driven by separate neuromodulation signal (NMS) channels, necessitating a multichannel system.

A further need for multichannel neuromodulation signal (NMS) is the control of multiple symptoms of the movement disorder and the side effects arising from pharmacologic treatment. Optimal control of tremor, dyskinesias, and rigidity are not achieved by modulation of the same site at the same intensity. For this reason, multiple and separately controlled channels of neuromodulation are required to simultaneously achieve optimal control of these multiple symptoms and side effects. Each of these symptoms and side effects may be considered to comprise one or more element in a multivariable disease state. A multivariable control system will be required to optimally drive each of these disease state elements to its desired value, ideally toward a target minimum level and thus achieve optimal control of this multiplicity of disease states. This multivariable control system may be implemented as multiple independent control laws each with separate though potentially overlapping sensory inputs or as a multivariable control law matrix.

Stimulation via each of the multiple channels comprising the neuromodulation signal (NMS) 998 is characterized by separate though possibly overlapping sets of one or more of the following parameters: stimulation voltage, stimulation current stimulation frequency of pulses within the same burst, frequency of bursts, pulse width, pulses per burst, duration of burst, and interpulse interval. The stimulus waveforms are amplified by output amplifier 74 to generate an amplified stimulus waveform. Specifically, pulse generator 73 transfers information to output amplifier 74 which includes information that uniquely specifies the desired stimulation waveform. In a preferred embodiment, the information is in the form of an analog signal which represents a scaled version of the voltage or current waveform to be delivered to the tissue. It should be understood that other forms of the signal generated by pulse generator 73 may be used, including combinations of at least one of analog and digital representations. Output amplifier 74 performs amplification and regulation of the received stimulus waveform generated by the pulse generator 73. This may be regulation of electrical current to achieve desired voltage or regulation of electrical voltage to achieve desired current, depending on whether a voltage or current waveform is to be delivered to the nervous system component.

As one skilled in the relevant art would find apparent, voltage regulation is simpler to implement, and is a technique which is commonly used by many conventional stimulators. Current regulation, on the other hand, is more complex but allows for more precise control of the applied stimulation. Current regulation insures that a specified amount of current is delivered, regardless of the impedance of the electrode. Current regulation is advantageous in that it allows for precise control of stimulation level despite changes in electrode impedance which invariably occur over time. Since electrode impedances often change, typically increasing as they become encapsulated by fibrosis, current regulation is preferred to avoid the decrease in current which would occur if voltage regulation were to be used in such circumstances.

The amplified stimulus waveform generated by output amplifier 74 is conducted along stimulator amplifier output path 112 to multiplexor 75. Multiplexor 75 allows for delivery of a stimulating electrode output signal (SEOS) to the intracranial stimulating electrode array 37, multiplexed with sensing of a stimulating electrode input signal (SEIS). Specifically, multiplexor 75 serves to alternately connect intracranial stimulating electrode (ICSE) array 37 to output amplifier 74 and intracranial stimulating electrode amplifier 57. Connection of intracranial stimulating electrode (ICSE) array 37 to output amplifier 74 facilitates delivery of neural modulation signal to neural tissue, while connection of intracranial stimulating electrode (ICSE) array 37 to intracranial stimulating electrode amplifier 57 facilitates monitoring of neural activity in the region being stimulated.

Multiplexor 75 allows delivery of neural modulation signals to neural tissue concurrent with monitoring of activity of same neural tissue; this facilitates real-time monitoring of disease state and response to treatment. Stimulating electrode output signal (SEOS) from output amplifier 74 is conducted along stimulator amplifier output path 112 to multiplexor 75. Multiplexor 75 conducts output from output amplifier 74 to stimulator output path 111 which conducts the stimulating electrode output signal to intracranial stimulating electrode array 37. To facilitate periodic sampling of neural activity in tissue being stimulated, multiplexor 75 alternatively conducts signal arising from stimulated tissue via intracranial stimulating electrode array (ICSE) 37 and stimulator output path 111 to multiplexed stimulator recording input path 113 and intracranial stimulating electrode amplifier 57.

Multiplexor 75 selectively conducts the signal on multiplexed stimulator recording input path 113 to amplifier 57. Multiplexor 75 may alternate conduction between path 111 and path 112 or path 113 using temporal multiplexing, frequency multiplexing or other techniques to allow concurrent access to the intracranial stimulating electrode (ICSE) array 37 for modulation of tissue activity and monitoring of tissue activity. Temporal multiplexing is a well known technique and frequency multiplexing of stimulation and recording signals in known to those skilled in the art. In this embodiment, temporal multiplexing is accomplished by alternately connecting stimulator output path 111 to stimulator amplifier output path 112 and multiplexed stimulator recording input path 113. In one embodiment, frequency multiplexing is accomplished by passing a band-limited portion of stimulating electrode output signal SEOS via the stimulator output path 111 to intracranial stimulating electrode array 37 while simultaneously monitoring activity on intracranial stimulating electrode array 37 within a separate frequency band, thereby generating a stimulating electrode input signal SEIS. Thus, stimulating electrode input signal SEIS is conducted from the intracranial stimulating electrode array 37 to stimulator output path 111 to multiplexor 75 and via multiplexed stimulator recording input path 113 to intracranial stimulating electrode array amplifier 57.

Multiplexor 75 facilitates conduction between stimulator amplifier output path 112 and multiplexed stimulator recording input path 113 to allow automated calibration. In this mode, a calibration signal of known amplitude is generated by pulse generator 73 and amplified by output amplifier 74 which, for calibration purposes, delivers a voltage regulated signal via stimulator amplifier output path 112 to multiplexor 75. Multiplexor 75 conducts amplified calibration signal to multiplexed stimulator recording input path 113 which conducts signal to intracranial stimulating electrode amplifier 57.

Although not included in the illustrative embodiment, multiplexed or intermittent connection of stimulator amplifier output path 12 to the inputs of at least on of the other amplifiers, including EMG amplifier 59, EEG amplifier 60, accelerometer amplifier 61, acoustic amplifier 62, peripheral nerve electrode amplifier 63, and intracranial recording electrode amplifier 58, may be implemented without departing from the present invention. The same multiplexed connections may be used to calibrate the pulse generator 73 and output amplifier 74.

Figure 15:
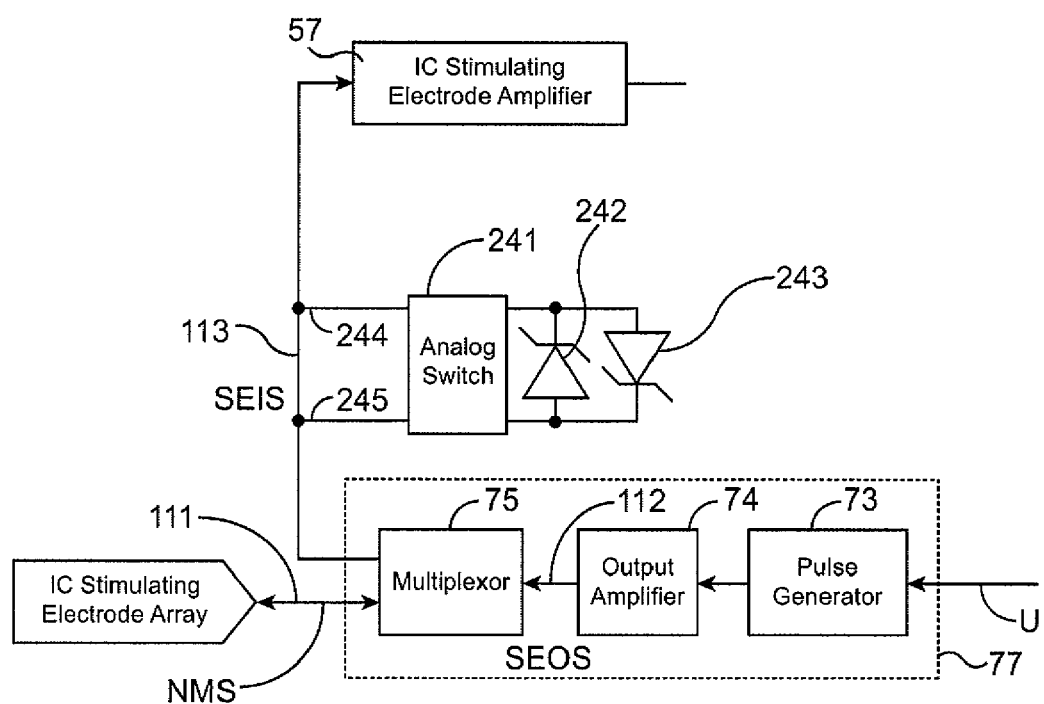
FIG. 15 is a schematic block diagram of an analog switch used to connect one or an opposing polarity pair of Zener diodes across the noninverting and inverting inputs of an intracranial recording electrode amplifier.

Referring to FIG. 15, an analog switch may be used to connect one or an opposing polarity pair of Zener diodes across the noninverting and inverting inputs of intracranial recording electrode amplifier 58. In this configuration, the Zener diodes would limit the maximal amplitude of the calibration signal in one or both polarities to known values, allowing for accurate calibration of intracranial recording electrode amplifier 58. The analog switch may then be deactivated, removing the cathode of the single or pair of Zener diodes from the input of intracranial recording electrode amplifier 58 to allow measurement of stimulating electrode output signal (SEOS) for calibration of pulse generator 73 and output amplifier 74. This is described in greater detail below.

Multiplexor 75 also facilitates conduction between stimulator amplifier output path 112, multiplexed stimulator recording input path 113, and stimulator output path 111 to allow measurement of impedances of components of intracranial stimulating electrode array 37. In this electrode impedance measurement mode, a three way connection between stimulator amplifier output path 112, multiplexed stimulator recording input path 113, and stimulator output path 111 is created. When output amplifier 74 is operated in current regulated mode, it delivers an SEOS of known current via stimulator output path 111 to intracranial stimulating electrode array 37. The voltages generated across the elements of intracranial stimulating electrode array 37 generally are the products of the electrode impedances and the known stimulating currents. These voltages are sensed as the stimulating electrode input signal SEIS by the intracranial stimulating electrical amplifier 57.

Reference module 116 contains memory registers in which control law reference values are stored. Such reference values include but are not limited to target disease state levels, target symptom levels, including target tremor level, and threshold levels. Threshold levels include but are not limited to disease and symptom levels, including tremor threshold levels. Neural modulation amplitude may be increased when at least one of disease state and symptom level exceed the corresponding threshold. Similarly neural modulation amplitude may be decreased or reduced to zero when either the disease state or symptom level falls below the corresponding threshold.

Reference module 116 is connected to patient interface module 55, facilitating both monitoring and adjustment of reference values by patient. Reference module 116 is also connected to supervisory module 56, facilitating both monitoring and adjustment of reference values by physician or other health care provider. Supervisory module 56 may be used by the neurologist, neurosurgeon, or other health care professional, to adjust disease state reference R values for the one or more control laws implemented in control circuit 72. The disease state reference R values specify the target level at which the corresponding disease states are to be maintained, as quantified by the disease state estimate X values, providing reference values for control laws implemented in control law circuit block 231 (FIG. 11; discussed below) and contained within control circuit 72. Reference module 116 may also receive input from control circuit 72, facilitating the dynamic adjustment of reference disease state "r" (discussed below). Reference module 116 may additionally receive input from disease state estimator module array (DSEMA) 229 (FIG. 11; discussed below) and aggregate disease state estimator 195 (FIG. 11; discussed below) and components of signal processor 71, for use in dynamically determining reference disease state "r".

Figure 10:
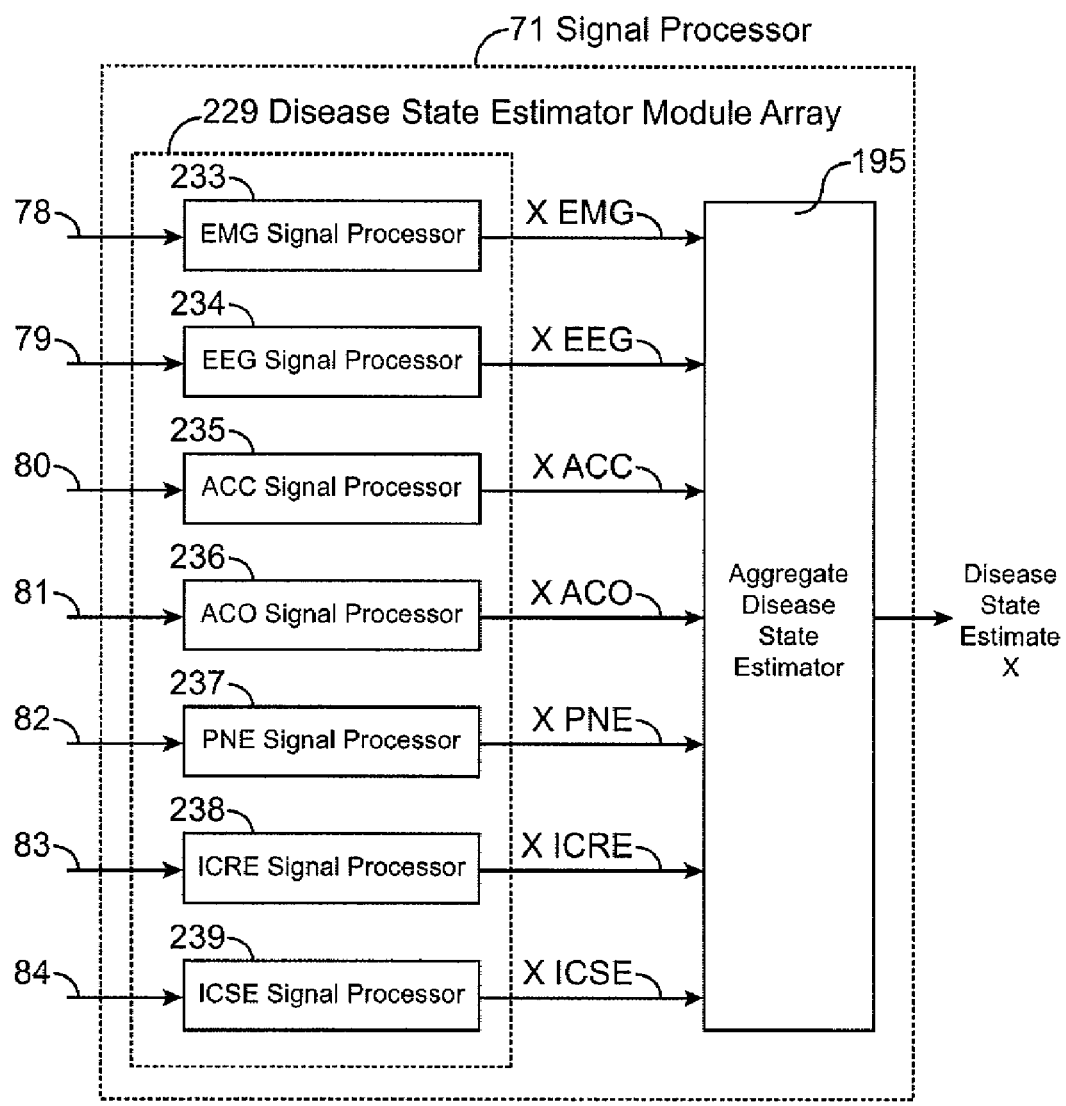
FIG. 10 is a schematic diagram of one embodiment of the signal processor illustrated in FIG. 2.

FIG. 10 is a schematic diagram of signal processor 71. In this illustrative embodiment, signal processor 71 includes a disease state estimator module array 229 that includes one or more signal processor modules that generate a quantitative estimate of at least one disease state or parameter thereof based upon its respective input. For example, magnitude of tremor in the 3 to 5 Hz range represents one possible representation of a disease state. This could be an absolute or normalized quantification of limb acceleration in meters per second squared. This component of the disease state would be calculated almost exclusively from sensory feedback from accelerometer array 52. Another possible disease state is the frequency of occurrence of episodes of tremor activity per hour. This element of the disease state may be estimated from any of several of the sensory feedback signals. In this case, the most accurate representation of this disease state element is obtained by applying a filter such as a Kalman filter to calculate this parameter based upon a weighted combination of the sensory feedback signals. Such weighting coefficients are calculated from quantified measures of the accuracy of and noise present upon each sensory feedback channel.

In the illustrative embodiment, disease state estimator module array 229 includes an EMG signal processor 233, EEG signal processor 234, accelerometer signal processor 235, acoustic signal processor 236, peripheral nerve electrode (PNE) signal processor 237, intracranial recording electrode (ICRE) signal processor 238, and intracranial stimulating electrode (ICSE) signal processor 239. It should be understood that other signal processors may also be included in the array 229. Inputs to these modules include conditioned EMG signal path 78, conditioned EEG signal path 79, conditioned accelerometer signal path 80, conditioned acoustic signal path 81, conditioned peripheral nerve electrode (PNE) signal path 82, conditioned intracranial recording electrode (ICRE) signal path 83, and conditioned intracranial stimulating electrode (ICSE) signal path 84, respectively. Communication between these modules is facilitated. The output(s) of each of the modules is connected to an aggregate disease state estimator 195. Aggregate disease state estimator 195 generates a single or plurality of disease state estimates "X" indicative of state of disease and response to treatment.

In the preferred embodiment, the acceleration of at least one of the affected limb and the head, each of which is sensed as a sensory feedback channel by an element of the accelerometer array 52, serves as respective elements in the disease state estimate X. These elements of disease state estimate X are inputs to respective control laws implemented in control circuit 72. of input to the control law. A control law governing the function of a proportional controller using acceleration as its single sensory feedback channel is given by equation (1):

$$u_1 = 0.3166(V \cdot s^2/m) \cdot ACC \tag{1}$$

and if $$u_2 = 0.6333(V \cdot s^2/m) \cdot ACC \tag{2}$$

where $u_1$ and $u_1$ are the stimulation voltage given in volts; and ACC is the limb, mandible, or head acceleration given in meters per second squared ($m/s^2$).

In equation (1), the stimulation site is the ventroposterolateral pallidum, the output stage mode is voltage regulated, the waveform is a continuous train of square waves, the amplitude us is given in volts (typically approximately 1 volt), and the remaining stimulation parameters include a pulse width of 210 microseconds, and a stimulation frequency of 130 Hz. In equation (2), the stimulation site is the ventral intermediate thalamic nucleus (Vim), the output stage mode is voltage regulated, the waveform is an intermittent train of square waves with an on time of 5 minutes and an off time of 45 seconds, the amplitude $u_2$ is given in volts (typically approximately 3 volts), and the remaining stimulation parameters include a pulse width of 60 microseconds, and a stimulation frequency of 130 Hz.

In one preferred embodiment, the ACC signal represents the average acceleration over a finite time window, typically 15 to 60 seconds. This effective lowpass filtering provides a stable sensory feedback signal for which a proportional control law is appropriate. If stability and performance requirements dictate, as is familiar to those practiced in the art of feedback control, other components, including an integrator and a differentiator may be added to the control law to produce a proportional-integral-differential (PID) controller, as needed.

One preferred embodiment also includes electromyographic (EMG) signals as sensory feedback in the calculation of at least one element of the disease state estimate X which is an input to the control law. As discussed in the section describing EMG signal processor 233, the EMG signals are rectified by full wave rectifier 123, passed through envelope determiner 124, passed through several bandpass filters 125, 127, 129, 131, 133 and associated threshold discriminators 126, 128, 130, 132, 134 and then passed in parallel to each of integrator 135 and counter 136. Integrator 135 generates an output which is a weighted function of it inputs and represents the average magnitude of tremor activity over a given time window $-w/2$ to $+w/2$. A simplified representation of this is given by equation (3):

$$u_3 = \int_{-w/2}^{+w/2} X_{EMG} - dt \tag{3}$$

over a given time window $-w/2$ to $+w/2$. A simplified representation of this is given by the equation:

As is familiar to those skilled in the art of control theory, an integral controller is marginally stable. To confer stability to this control law, the equivalent of a finite leak of the output magnitude $u_4$ to zero is added to maintain stability. A more general form of this equation is given by equation (4):

$$-C_1 \partial u_4/dt + C_2 \cdot u_4 = B_1 \cdot \partial X_{EMG}/dt + B_2 \cdot X_{EMG} \tag{4}$$

Shown as a system function, the control law output U is given as the product of a transfer function H(s) and the disease estimate X, the input to the control law:

$$u(s)(C_1 \cdot s + C_2) = X_{EMG}(s)(B_1 \cdot s + B_2) \tag{5}$$

$$u(s)/X_{EMG}(s) = (B_1 \cdot s + B_2)/(C_1 \cdot s + C_2) \tag{6}$$

$$H(s) = u(s)/X_{EMG}(s) = (B_1 \cdot s + B_2)/(C_1 \cdot s + C_2) \tag{7}$$

One such control law with an appropriate time response is given by:

$$H(s)=u(s)/X_{EMG}(s)=G_{VIEMG}(0.1 \cdot s+1)/(2 \cdot s+1) \tag{8}$$

where $G_{VIEMG}$ is the gain in neuromodulation signal (NMS) (volts per volt of EMG signal).

For intramuscular EMG electrodes, signal amplitudes are on the order of 100 microvolts. For neuromodulation signal (NMS) parameters of 2 volts amplitude, 60 microseconds pulse width, 130 Hz stimulation frequency, the appropriate overall gain $G'_{VIEMG}$ is 20,000 $volts_{NMS}/volts_{EMG}$. Since the preamplifier stage performs amplification, 1000, in the preferred embodiment, the actual value for $G_{VIEMG}$ as implemented in the control law is 20 $volts_{NMS}/volts_{PREAMPL\ EMG}$.

Disease state estimator 195 determines estimates of disease state including but not limited to long-term, or baseline, components, circadian components, postprandial components, medication induced alleviation of components, medication induced components, and future predicted behavior of said components. Output of disease state estimator 195 includes output of observer 228, depicted in FIG. 11, which makes use of an adaptive model of disease behavior to estimate disease states which are not directly detectable from sensors. Such sensors provide input to the adaptive model to correct state estimates and model parameters. Each of the signal processor modules in disease state estimator module array 229 are described below.

Figure 3:
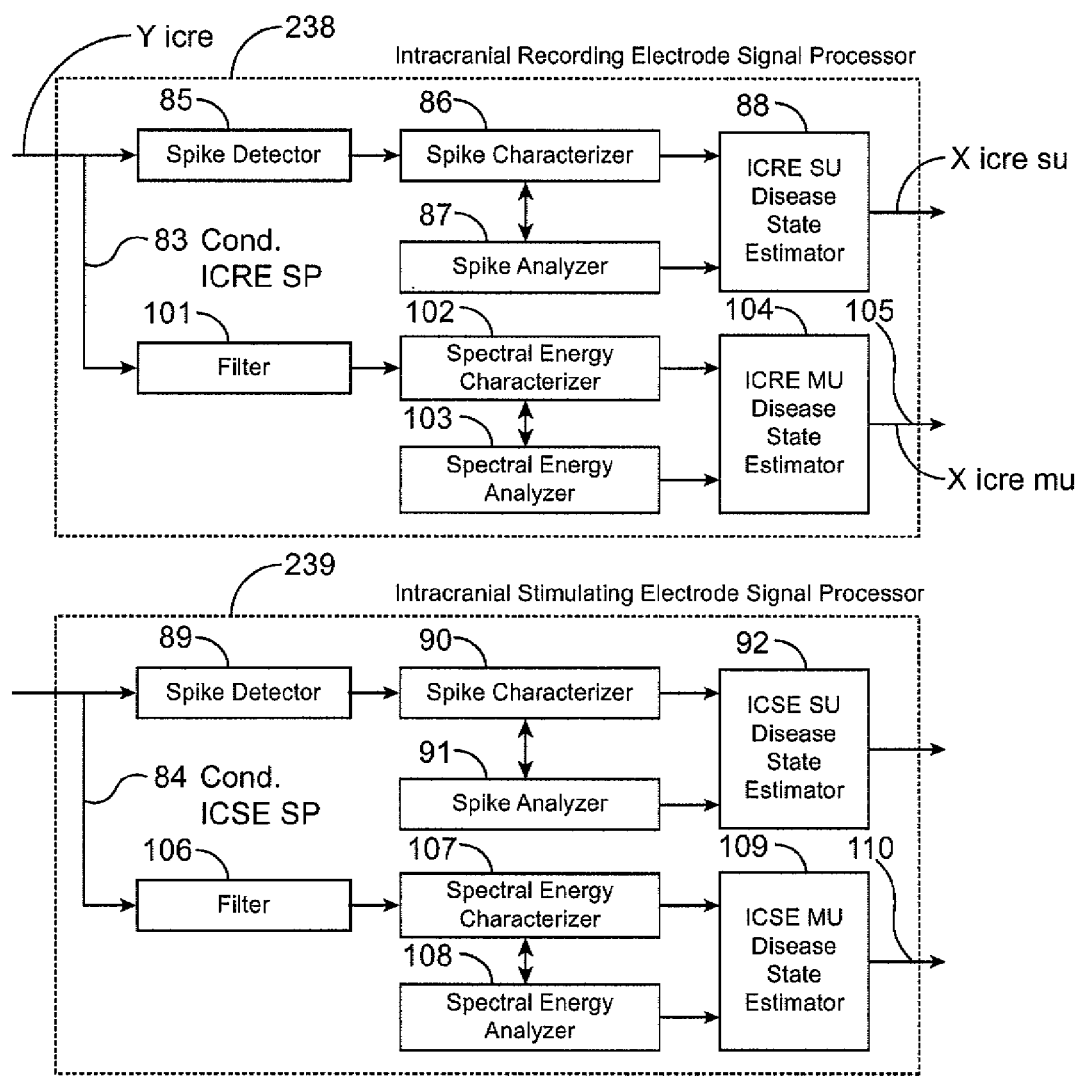
FIG. 3 is a block diagram of one embodiment of an intracranial recording electrode (ICRE) signal processor and an intracranial stimulating electrode (ICSE) signal processor each of which are included within the signal processor illustrated in FIG. 2.

FIG. 3 is a block diagram of intracranial recording electrode (ICRE) signal processor 238 and intracranial stimulating electrode (ICSE) signal processor 239, each of which are included within signal processor 71 in the illustrative embodiment illustrated in FIGS. 2 and 10. ICRE signal processor module 238 and ICSE signal processor module 239 process signals from one or more intracranial electrodes, including but not limited to those comprising intracranial recording electrode array 38 and intracranial stimulating electrode array 37. As noted, intracranial stimulating electrode array 37 is comprised of one or more intracranial stimulating electrodes while intracranial recording electrode array 38 is comprised of one or more intracranial recording electrodes.

Figure 14:
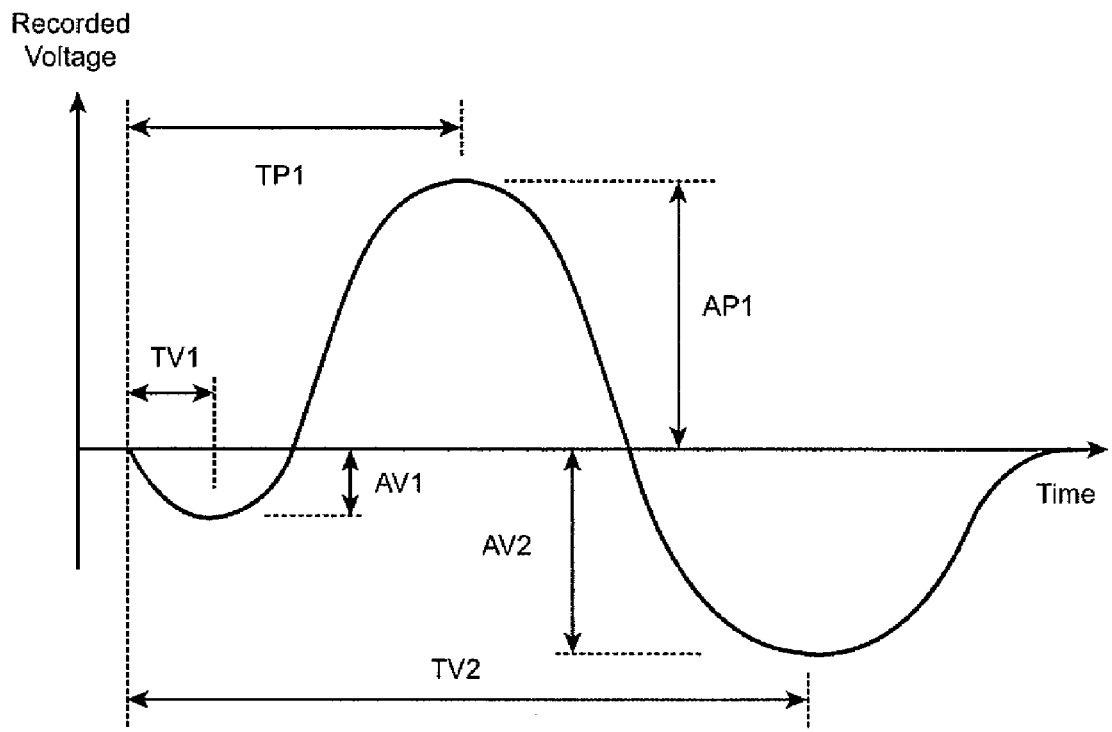
FIG. 14 is a schematic diagram of one example of the recorded waveforms.

Input to ICRE signal processor 238 is conditioned intracranial recording electrode (ICRE) signal path 83 noted above. This input is connected to a spike detector 85 which identifies action potentials. Spike detection techniques are well known to those skilled in the art and generally employ low and high amplitude thresholds. Waveforms having amplitudes greater than the low threshold and lower than the high threshold are determined to be action potentials. These thresholds may be predetermined or adjusted manually using supervisory module 56 or may be adapted in real-time by an algorithm which sweeps the threshold through a range of values to search for values at which action potential spikes are consistently recorded. The low amplitude threshold is set above the amplitude of background noise and that of nearby cells not of interest, and the high amplitude threshold is set above the amplitude of the desired action potentials to allow their passage while eliminating higher amplitude noise spikes, such as artifacts arising from electrical stimulation currents. Bandpass, notch, and other filtering techniques may also be used to improve signal to noise ratio and the sensitivity and specificity of spike detectors. Individual neuron action potentials are usually recorded using fine point high-impedance electrodes, with impedances typically ranging from 1 to 5 megohms. Alternatively, larger lower-impedance electrodes may be used for recording, in which case the signals obtained typically represent aggregate activity of populations of neurons rather than action potentials from individual neurons. Spike detector 85 passes the waveform(s) to a spike characterizer 86. Spike characterizer 86 determines firing patterns of individual neurons. The patterns include, for example, tonic activity, episodic activity, and burst firing. Spike characterizer 86 calculates parameters that characterize the behavior of the individual and groups of neurons, the activity of which is sensed by intracranial recording electrode array 38. In one embodiment, the characterization includes parameterization of recorded action potentials, also referred to as spikes, bursts of spikes, and overall neural activity patterns. This parameterization includes, but is not limited to, calculation of frequencies of spikes, frequencies of bursts of spikes, interspike intervals, spike amplitudes, peak-to-valley times, valley-to-peak times, spectral composition, positive phase amplitudes, negative phase amplitudes, and positive-negative phase differential amplitudes. These parameters are depicted in FIG. 14 and are discussed below. Based on these parameterization, spike characterizer 86 discriminates individual spikes and bursts originating from different neurons. This discrimination facilitates serial monitoring of activity of individual and groups of neurons and the assessment and quantification of activity change, reflective of change in disease state and of response to therapy.

A spike analyzer 87 receives as input the parameters from spike characterizer 86. Spike analyzer 87 extracts higher level information, including but not limited to average spike frequencies, average interspike intervals, average amplitudes, standard deviations thereof, trends, and temporal patterning. By comparing current spike frequency rates to historical spike frequency data, spike analyzer 87 additionally calculates the rates of change of spike parameters. Prior trends and current rates of change may then be used to predict future behaviors. Rates of change of the parameters include but are not limited to autocorrelation and digital filtering.

Spike analyzer 87 may receive additional input from accelerometers, including but not limited to at least one of head mounted accelerometer 12, proximal accelerometer 28, enclosure mounted accelerometer 36, and distal accelerometer 33. Spike analyzer 87 may receive indirect input from accelerometers, such as from conditioned or processed signals arising therefrom. This may include, for example, the signal transmitted by conditioned accelerometer signal path 80.

Spike analyzer 87 may also receive additional input from EMG arrays 50, such as a proximal EMG electrode array 45, enclosure-mounted EMG electrode array 46, or distal EMG electrode array 47. Spike analyzer 87 may receive indirect input from such EMG electrode arrays 50, such as from conditioned or processed signals arising therefrom, including but not limited to the signal transmitted by conditioned EMG signal path 78.

These additional inputs from accelerometers and EMG arrays facilitates the characterization of neuronal firing patterns relative to activity of muscle groups and movement of joints, including but not limited to characterization of neuronal spike amplitudes and tuning of firing to movement, including but not limited to movement velocity and direction. The characterization may be used to assess functioning of the sensorimotor system, including but not limited to motor response time, and to measure the disease state and response to therapy.

Intracranial recording electrode (ICRE) single unit-based (SU) disease state estimator 88 receives input from spike characterizer 86 and/or spike analyzer 87. Spike analyzer 87 provides higher level information, including but not limited to average spike frequencies, average interspike intervals, average amplitudes, standard deviations thereof, trends, and temporal patterning to disease state estimator 88. These inputs are representative of the current neuronal activity in the tissue from which the intracranial recording electrodes (ICRE) are recording. ICRE SU disease state estimator 88 may also receive input representative of one or more signals, including desired neuronal activity, from control circuit 72. The ICRE SU disease state estimate $X_{ICRE\_SU}$ calculated by ICRE SU disease state estimator 88, may be comprised of a single or a plurality of signals, consistent with a representation of the disease state by a single or a multitude of state variables, respectively. The ICRE MU disease state estimate $X_{ICRE\_MU}$ calculated by ICRE MU disease state estimator 88, may be comprised of a single or a plurality of signals, each representative of multiunit neurophysiological signals, i.e. reflective of concurrent activity of numerous neurons. Both ICRE SU disease state estimate $X_{ICRE\_SU}$ and ICRE MU disease state estimate $X_{ICRE\_MU}$ are output to aggregate disease state estimator 195.

Referring to FIG. 3, conditioned intracranial recording electrode (ICRE) signal path 83 additionally connects to filter 101. Filter 101 is preferably of the bandpass type filter. In one embodiment, the bandpass filter 101 has a passband of 0.1 to 100 Hz, although other ranges may be used. Output of filter 101 connects to spectral energy characterizer 102, which may be implemented in any of several hardware or software forms. For example, in one embodiment, the spectral energy characterizer 102 is implemented using real-time fast Fourier transform (FFT) techniques. Alternatively, other digital or analog techniques may also be used.

It should be understood that inputs and outputs from spike detector 85, spike characterizer 86, spike analyzer 87, disease state estimator 88, filter 101, spectral energy characterizer 102, spectral energy analyzer 103, and disease state estimator 104 may be comprised of individual signals or a plurality of signals. Further, spike detector 85, spike characterizer 86, spike analyzer 87, disease state estimator 88, filter 101, spectral energy characterizer 102, spectral energy analyzer 103, and disease state estimator 104 may each have different parameters and signal processing characteristics for each of the multiple signals processed. Because baseline neuronal firing rates differ among various anatomical and functional regions of the brain, and their involvement in disease states and susceptibility to change in firing patterns varies, the respective signal processing circuitry and logic will vary correspondingly. For example, baseline firing rates among neurons in the globus pallidus externus are approximately 43 Hz and those in the globus pallidus internus are 59 Hz.

The input to intracranial stimulating electrode ICSE signal processor 239, referred to above as conditioned intracranial stimulating electrode (ICSE) signal path 84, connects to spike detector 89. Spike detector 89 identifies action potentials in a manner similar to that described above with reference to spike detector 85. Intracranial stimulating electrode ICSE signal processor 239 performs a similar set of functions as intracranial recording electrode ICRE signal processor 238 on a different set of sensory feedback signals. As noted above, spike detection techniques are well known to those skilled in the art.

Spike detector 89 passes waveforms to spike characterizer 90, which uses well known techniques to calculate parameters than characterize the behavior of the individual and groups of neurons, the activity of which is sensed by intracranial stimulating electrode array 37. As noted above with respect to spike characterizer 86, this characterization may include parameterization of spikes, bursts of spikes, and overall neural activity patterns. Similarly, the parameterization may include calculation of spike frequencies, burst frequencies, inter-spike intervals, amplitudes, peak-to-valley times, valley-to-peak times, spectral composition, positive phase amplitudes, negative phase amplitudes, and positive-negative phase differential amplitudes. Such characterization of neural spikes is known to those skilled in the art of neurophysiology. Based on this parameterization, spike characterizer 90 discriminates individual spikes and bursts originating from different neurons. As noted, such discrimination facilitates serial monitoring of activity of individual and groups of neurons and the assessment and quantification of activity change, reflective of change in disease state and of response to therapy.

Spike analyzer 91 receives the parameters from spike characterizer 90, and extracts higher level information, including average spike frequencies, average interspike intervals, average amplitudes, standard deviations thereof, trends, and temporal patterning. The function and operation of spike analyzer 91 is similar to that described herein with reference to spike analyzer 87. Similarly, spike analyzer 91 may receive additional input directly or indirectly from accelerometers and/or EMG arrays to facilitate the characterization of neuronal firing patterns relative to activity of muscle groups and movement of joints. This may include, for example, characterization of neuronal spike amplitudes and tuning of firing to movement, including but not limited to movement velocity and direction. Such characterization may be used to asses functioning of the sensorimotor system, including but not limited to motor response time, and to measure the disease state and response to therapy.

Intracranial stimulating electrode (ICSE) single unit-based (SU) disease state estimator 92 receives input from either or both spike characterizer 90 and spike analyzer 91. ICSE SU disease state estimator 92 receives input representative of the current neuronal activity from spike characterizer 90. ICSE SU disease state estimator 92 may receive input representative of at least one of several signals, including desired neuronal activity, actual neuronal activity, and the difference between these quantities. The ICSE SU disease state estimate, calculated by ICSE SU disease state estimator 92, may be comprised of a single or a plurality of signals, consistent with a representation of the disease state by a single or a multitude of state variables, respectively.

As with intracranial recording electrode signal processor 238, inputs and outputs from spike detector 89, spike characterizer 90, spike analyzer 91, disease state estimator 92, filter 106, spectral energy characterizer 107, spectral energy analyzer 108, and disease state estimator 109 may include individual or a plurality of signals, and each may have different parameters and signal processing characteristics for each of the multiple signals processed. Because baseline neuronal firing rates differ among various anatomical and functional regions of the brain, and their involvement in disease states and susceptibility to change in firing patters varies, the respective signal processing circuitry and logic varies correspondingly.

Figure 4:
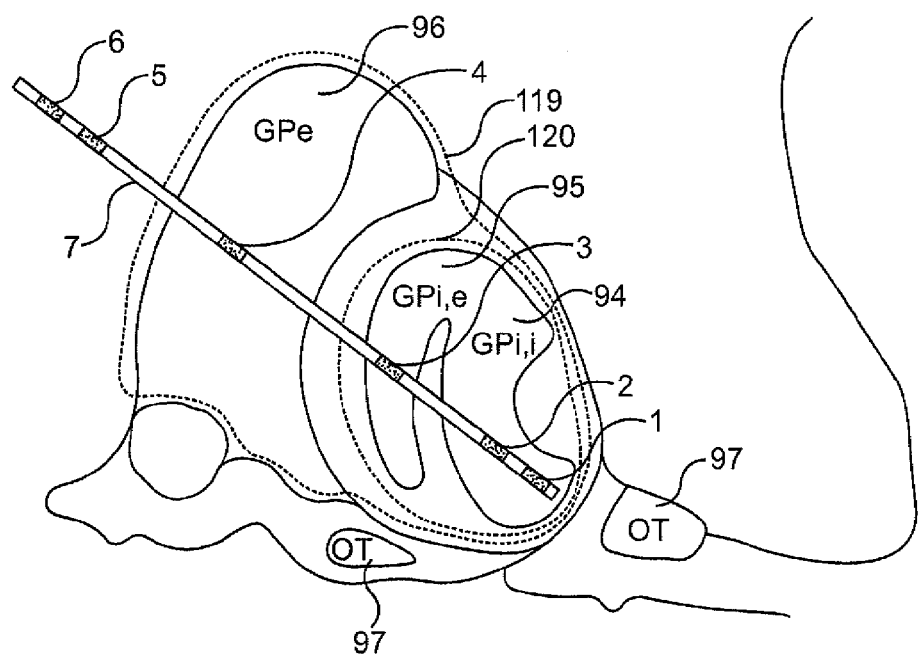
FIG. 4 is a schematic diagram of a globus pallidus implanted with stimulating and recording electrodes in accordance with one embodiment of the present invention.

FIG. 4 is a schematic diagram of a globus pallidus 119 implanted with stimulating and recording electrodes. Intracranial catheter 7 is shown in place with electrode of the intracranial stimulating electrode array 37 located within the globus pallidus internus (Gpi) 120, including globus pallidus internus internal segment (GPi,i) 94 and globus pallidus internus external segment (GPi,e) 95, and globus pallidus externus (GPe) 96.

Intracranial stimulating electrodes 1 and 2 are shown implanted in the globus pallidus internus internal segment (GPi,i) 94; and intracranial stimulating electrodes 3 and 4 are shown implanted in the globus pallidus internus external segment (GPi,e) 95 and globus pallidus externus (GPe) 96, respectively. It should be understood that this arrangement is illustrative of one preferred embodiment, and other stimulating and recording electrode configurations may be employed without departing from the present invention.

The optic tract 97 is shown in its close anatomical relationship to the globus pallidus internus (Gpi) 120. The risk inherent in treatment modalities involving irreversible tissue ablation should be apparent; stereotactic errors of only one to several millimeters during lesioning of the globus pallidus internus (Gpi) 120 may result in irreversible damage or complete destruction of the optic tract 97. Furthermore, the advantage of a system which dynamically adjusts the amplitude of inhibitory electrical stimulus to the globus pallidus 119 to minimize said amplitude offers the potential advantage of minimization of side effects including interference with visual signals of the optic tract 97 and prevention of overtreatment.

Intracranial stimulating electrodes 1, 2, 3, 4 are shown implanted in the GPi,i 94, GPi,e 95, GPe 96, respectively. This is one preferred embodiment. Numerous permutations of electrode stimulation site configuration may be employed, including more or fewer electrodes in each of these said regions, without departing from the present invention. Electrodes may be implanted within or adjacent to other regions in addition to or instead of those listed above without departing from the present invention, said other reasons including but not limited to the ventral medial Vim thalamic nucleus, other portion of the thalamus, subthalamic nucleus (STN), caudate, putamen, other basal ganglia components, cingulate gyrus, other subcortical nuclei, nucleus locus ceruleus, pedunculopontine nuclei of the reticular formation, red nucleus, substantia nigra, other brainstem structure, cerebellum, internal capsule, external capsule, corticospinal tract, pyramidal tract, ansa lenticularis, white matter tracts, motor cortex, premotor cortex, supplementary motor cortex, other motor cortical regions, somatosensory cortex, other sensory cortical regions, Broca's area, Wernickie's area, other cortical regions, other central nervous system structure, other peripheral nervous system structure, other neural structure, sensory organs, muscle tissue, or other non-neural structure.

Referring to FIGS. 3 and 4, a small percentage of cells in the globus pallidus internus internal segment 94 and globus pallidus internus external segment 95 exhibit tremor-synchronous discharges. As noted, at least one of single unit recordings from individual cells and multiple unit recordings from a plurality of cells are processed by signal processor 71. The single and multiple unit recordings may be derived from signals arising from intracranial stimulating electrode array 37, intracranial recording electrode array 38, or other sources. The output from signal processor 71 is connected to control circuit 72 and the output may represent at least one of disease state, magnitude of symptomatology, response to therapy, other parameter, and combination thereof.

Individual electrodes comprising intracranial stimulating electrode array 37 and intracranial recording electrode array 38 may each be of the microelectrode type for single unit recordings, macroelectrode type for multiple unit recordings, other electrode type, or a combination thereof, without departing from the spirit of the present invention. In one preferred embodiment, intracranial stimulating electrode array 37 consists of macroelectrodes. The macroelectrodes facilitate delivery of stimulation current at a lower charge density (coulombs per unit of electrode surface area) than microelectrodes of the same chemistry and surface treatment. The dimensions of intracranial stimulating electrodes 1–4 are selected such that the current density, or electrical current divided by electrode surface area, is below the threshold of reversible charge injection for the given electrode material.

Standard single cell recording technique, using an electrode with an impedance of typically 1–2 Megohms, involves bandpass filtering with −6 decibel (dB) points at 300 and 10,000 Hertz. This filtering, or a modification thereof, may be accomplished by ICRE filter 65 and ICSE filter 64; alternatively, it may be performed in spike detector 85 and spike detector 89, respectively, or other portion of stimulating and recording circuit 26.

Figure 5:
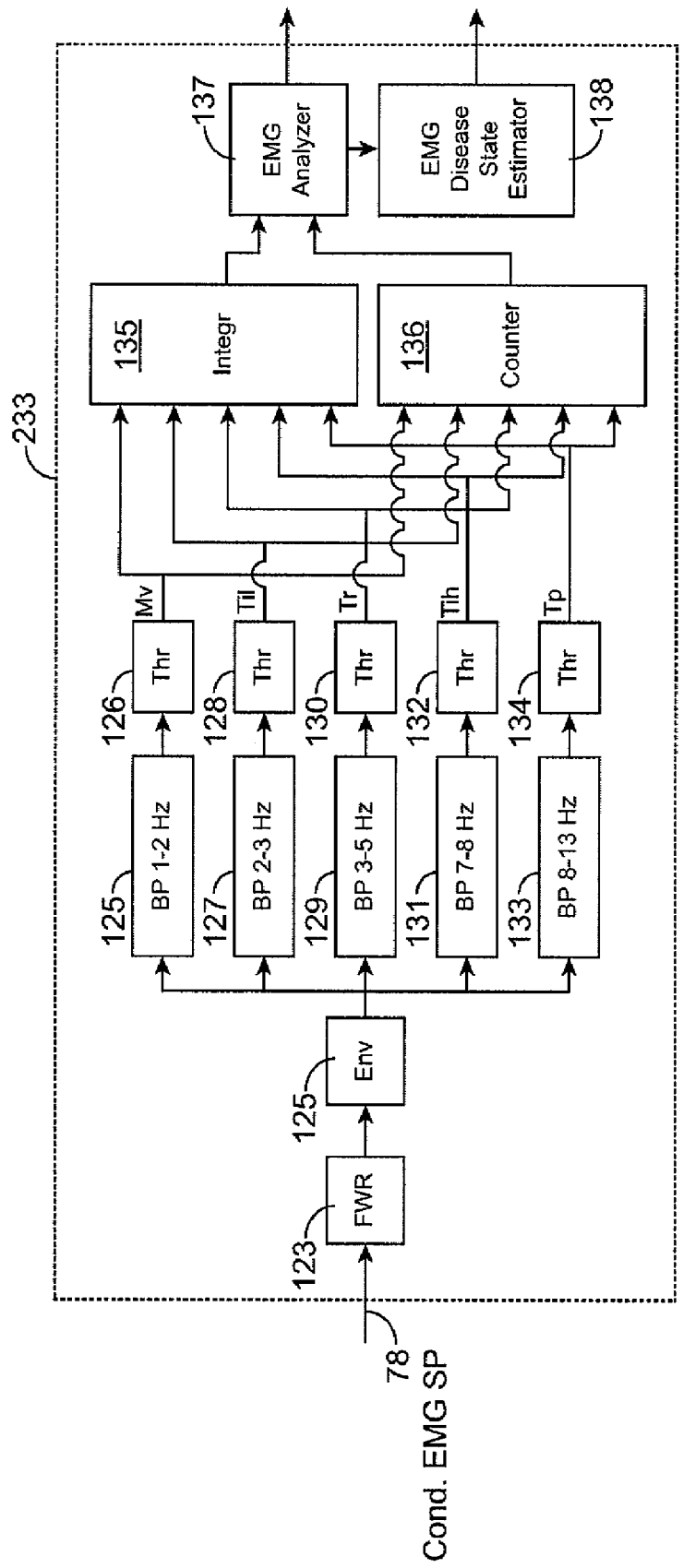
FIG. 5 is a block diagram of one embodiment of an EMG signal processor that is included in one embodiment of the signal processor illustrated in FIG. 2.

FIG. 5 is a block diagram of one embodiment of an EMG signal processor 233 which is included in a preferred embodiment of signal processor 71. EMG signal processor 233 processes signals from EMG electrode array 50, performing functions including but not limited to full wave rectification, envelope determination, bandpass filtering, threshold discrimination, and others described in more detail below, to produce signals indicative of the overall magnitude of tremor as well as the frequency at which tremor episodes occur. As noted, EMG electrode array 50 includes, but is not limited to, proximal EMG electrode array 45, enclosure-mounted EMG electrode array 46, and distal EMG electrode array 47. EMG electrodes may be located in any implanted or external location without departing from the present invention. For example, electrodes may be located within or in proximity to the hand, forearm, arm foot, calf, leg, abdomen, torso, neck, head, haw, lip, eyelid, larynx, vocal cords, and tongue.

Conditioned EMG signal path 78 is also connected to a well-known full wave rectifier 123 now or later developed. Output from the full wave rectifier 123 is coupled to an input of an envelope determiner 124. Determination of the envelope of a modulated signal is well known to those skilled in the art of electronics; this may be readily implemented in analog or digital hardware or in software. Output of envelope determiner 124 is connected to inputs of filters 125, 127, 129, 131 and 133. In one embodiment, filters 125, 127, 129, 131, 133 implement passbands of approximately 0.1–2 Hz, 2–3 Hz, 3–5 Hz, 7–8 Hz, and 8–13 Hz, respectively. Outputs of filters 125, 127, 129, 131 and 133 are connected to threshold discriminators 126, 128, 130, 132, 134, respectively.

Threshold discriminators 126, 128, 130, 132, and 134 generate outputs representing episodes of normal voluntary movement (Mv), low frequency intention tremor (Til) resting tremor (Tr), high frequency intention tremor (Tih), and physiologic tremor (Tp), respectively. These outputs are each connected to both of integrator 135 and counter 136. Integrator 135 generates outputs representative of the total activity of each of the above types of movement over at least one period of time. One such time period may be, for example, time since implantation, time since last visit to physician or health care provider, month internal, week interval, day interval, interval since last medication dose, interval since last change in stimulation parameters, weighted average of multiple time windows, and convolution of said activity with arbitrary time window function.

Counter 136 generates outputs representative of the number of episodes of each of the above types of movement over at least one period of time. Such period of time may be, for example, time since implantation, time since last visit to physician or health care provider, month interval, week internal, day interval, interval since last medication dose, interval since last change in stimulation parameters, and weighted average of said number of episodes over multiple time windows. Outputs from integrator 135 and counter 136 are connect to EMG analyzer 137. EMG analyzer 137 performs a number of functions including, for example, calculation of proportions of tremor activity which are of the rest and the intention type, ratios of different types of tremor activity, the level of suppression of resting tremor activity with voluntary movement, assessment of temporal patterns of EMG activity. EMG disease state estimator 138 receives inputs from EMG analyzer 137 and generates output representative of disease state based upon said input. In one preferred embodiment, two disease states are calculated, including a signal representative of the overall magnitude of tremor activity and a signal representative of the frequency of occurrence of tremor events. It should be understood that all signals paths may transmit one or more signals without departing from the present invention.

EMG signals may be sensed from any individual or group of muscles and processed in a manner including but not limited to the determination of severity and frequency of occurrence of various tremor types. Normal or physiologic tremor includes movement in the 8–13 Hz range and may be used as a normalization for the other types of sensed tremor. The predominant pathological form of tremor exhibited in Parkinson's disease patients is the classical "resting" tremor which includes movements in the 3–5 Hz range which are present at rest and suppressed in the presence of voluntary movement. In the present invention, quantification of this tremor type serves as a heavily weighted sensory input in the assessment of disease state and response to therapy. Parkinson's disease patients may also exhibit intention tremor, of which there are two types. The first type of intention tremor is referred to as "low frequency intention tremor" (Til in the present invention) and consists of movements in the 2–3 Hz range. A second type of intention tremor is referred to as "high frequency intention tremor" Tih in the present invention and consists of irregular movements in the 7–8 Hz range which persist throughout voluntary movement. Other types of tremor having associated movement in other ranges may be sensed and represented by the EMG signals.

EMG signals from at least one of orbicularis oculi (effecting eye closure), levator palpebrae (effecting eye opening), and other muscles contributing to eyelid movement, may be sensed and processed to determine frequency of eye blinking. Patients with Parkinson's disease exhibit a reduction in eyeblinking frequency from the normal of 20 per minute to 5 to 10 per minute, and this parameter is sensed as a measure of disease severity and response to treatment. Additionally, said EMG signals may be sensed and processed for detection and quantification of blepharoclonus, or rhythmic fluttering of the eyelids, and used as a measure of disease state and response to therapy. EMG signals, including baseline levels thereof, may be used to quantify rigidity and hypertonus as measures of disease state and response to therapy. Discharge patterns of individual motor units, including but not limited to synchronization of multiple units and distribution of intervals preceding and following discharge, may be used as measures of disease state and response to therapy.

Figure 6:
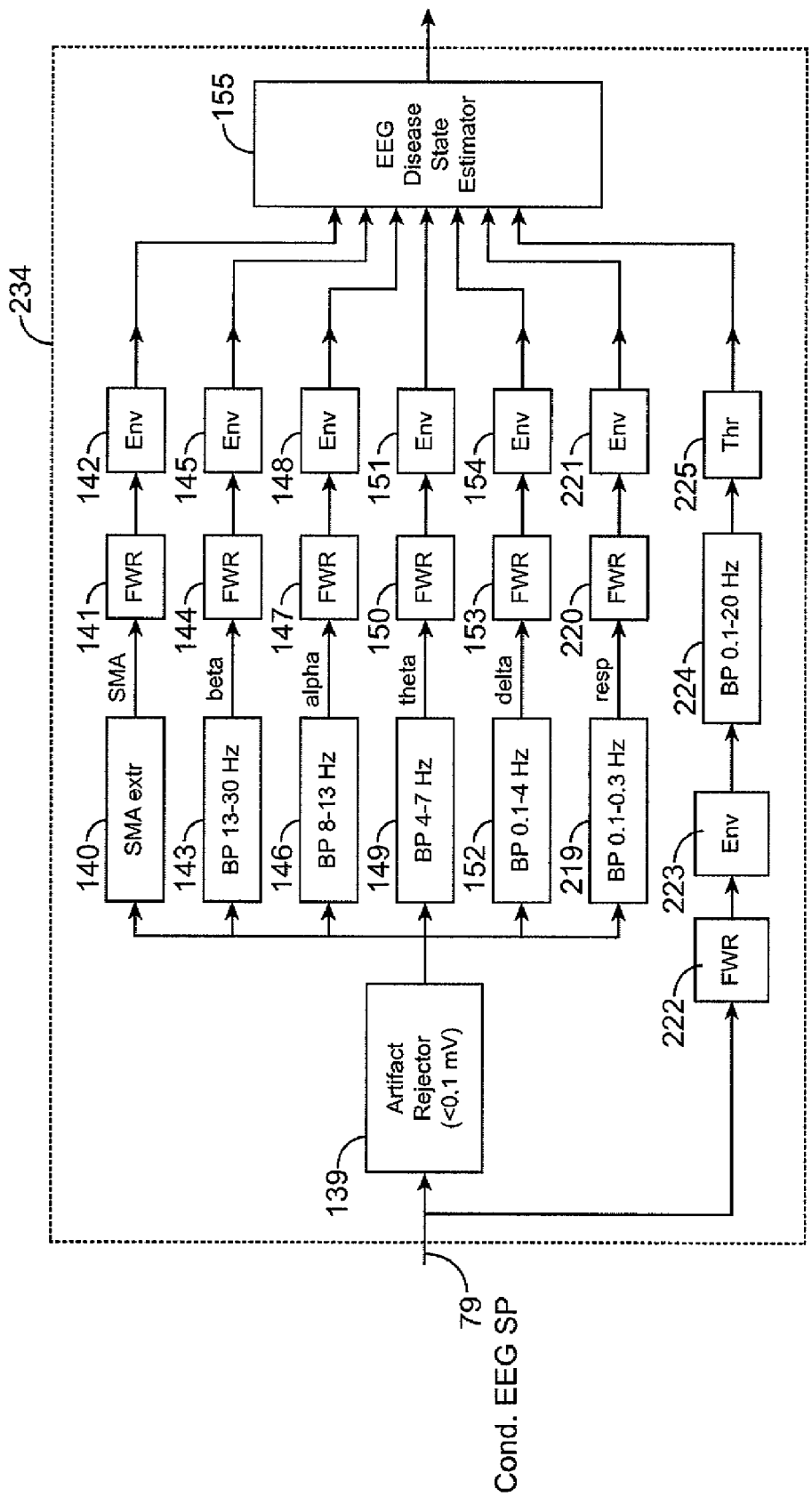
FIG. 6 is a block diagram of one embodiment of an EEG signal processor module that is included in one embodiment of the signal processor illustrated in FIG. 2.

FIG. 6 is a block diagram of one embodiment of an EEG signal processor module 234 which is included in embodiments of signal processor 71. The EEG signal processor module 234 processes signals from EEG electrode array 51. Conditioned EEG signal path 79 connects to an input of artifact rejecter 139 which rejects signals with amplitudes above a threshold. In one embodiment, this threshold is 0.1 mV. An output from artifact rejecter 139 connects to an input of each of supplementary motor area signal extractor 140 and filters 143, 146, 149, 152, 219. Filters 143, 146, 149, 152, and 219 are preferably of the bandpass type with passbands of 13–30 Hz, 8–13 Hz, 4–7 Hz, 0.1–4 Hz, and 0.1–0.3 Hz, respectively. Each filter output is connected to an input of an associated full wave rectifier 141, 144, 147, 150, 153, 220. Each full wave rectifier 141, 144, 147, 150, 153, 220 is connected to an input of an associated envelope determiner 142, 145, 148, 151, 154, and 221, respectively.

The envelope determiners generate a signal representative of the envelope of the input signal, typically performed by lowpass filtering with a time constant of 5 seconds. Finally, outputs of envelope determiners 142, 145, 148, 151, 154, and 221 are connected to EEG disease state estimator 155.

Signal SMA generated by supplementary motor area signal extractor 140 represents activity in the supplementary motor area ipsilateral to the intracranial stimulating electrode array (ISEA) 37. Supplementary motor area signal extractor 140 amplifies signals which are unique to elements of the EEG electrode array 51 which overlie the supplementary motor area. The supplementary motor area receives neural signals via neural projections from the basal ganglia and exhibits decreased activity in patients with Parkinson disease. The SMA is essential for sequential movements, which are often impaired in Parkinson's disease patients. The SMA signal provides a quantitative measure of disease state and response to therapy. The SMA signal is extracted from the anterior EEG leads, predominantly from those in the vicinity of the frontal cortex, and provides a quantitative measure of disease state and response to therapy. Signals beta, alpha, theta, and delta consist of 13–30 Hz, 8–13 Hz, 4–7 Hz, and 0.1–4 Hz activity, respectively.

Signal "resp" consists of 0.1–0.3 Hz activity and reflects respiration. Parkinson's disease patients exhibit irregular respiratory patterns characterized by pauses and by abnormally deep breathing while at rest and preceding speech. Assessment of respiratory irregularity as well as other parameters derived from such resp signal serve as quantitative measures of disease state and response to therapy.

Anterior EEG electrodes are also used to sense EMG signals, and the EMG signals are processed to determine activity of muscles including but not limited to those related to eye blinking activity. Processing of the EMG signals is included in the FIG. 6 circuit block diagram which contains the EEC signal processing component of signal processor 71. However, the processing could be incorporated into EMG signal processing component of signal processor 71 without departing from scope of the present invention. Conditioned EEG signal path 79 is additionally connected to input of full wave rectifier 222, the output of which is connected to the input of an envelope determiner 223. Envelope determiner 223 includes an output connected to input of filter 224. Filter 224 is preferably of the bandpass type with a passband range of 0.1 to 20 Hz. Filter 224 has an output connected to input of threshold discriminator 225, the output of which is connected to EEG disease state estimator 155.

Preferably, EMG signals arising from activity of at least one of orbicularis oculi (effecting eye closure), levator palpebrae (effecting eye opening), and other muscles the activity of which is associated with eyelid movement are sensed by anterior EEG electrodes. These EMG signals are processed to determine eye blink events, and the rates and regularity of eye blinking activity are calculated. Frequency and irregularity of eyeblinking as well as blepharoclonus, or rhythmic fluttering of the eyelids, are quantified as measures of disease state and response to therapy.

Figure 7:
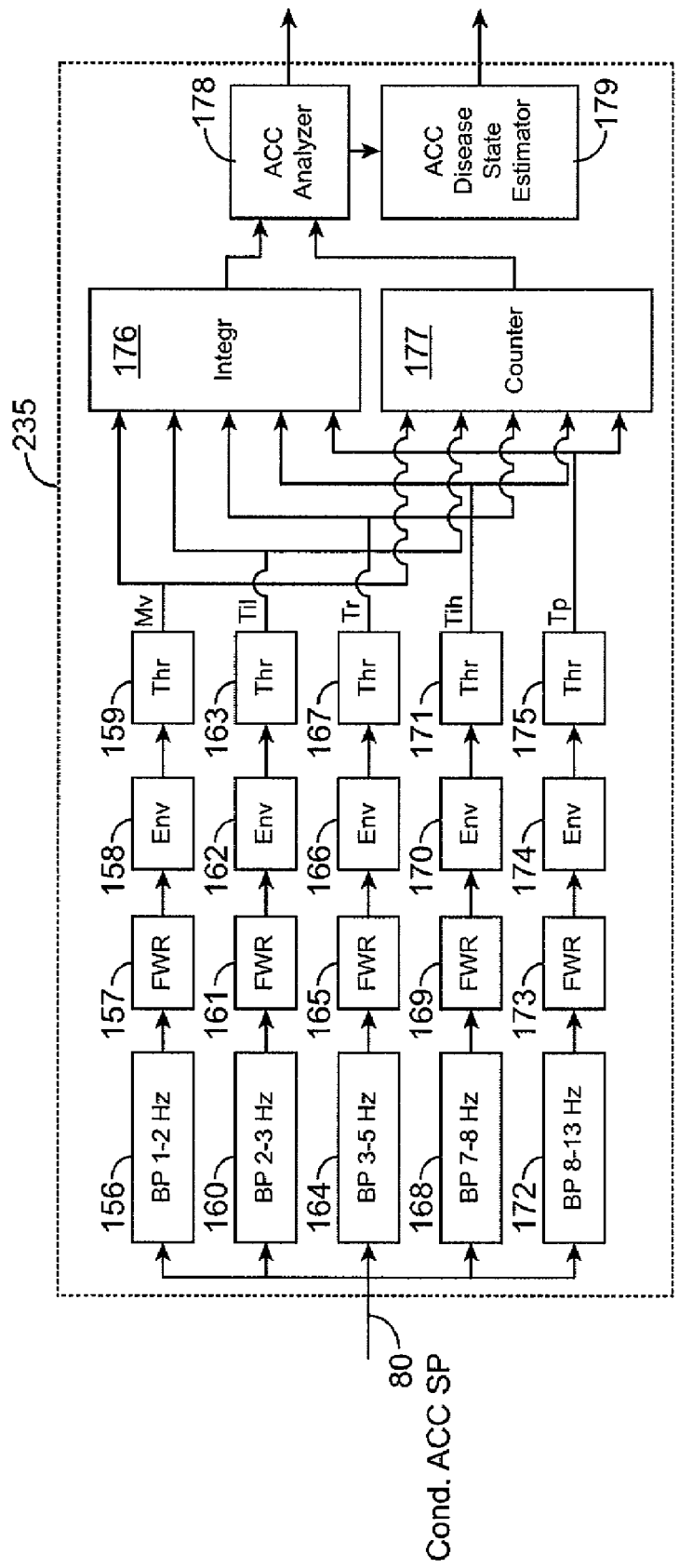
FIG. 7 is a block diagram of one embodiment of an accelerometer signal processor that is incorporated into certain embodiments of the signal processor illustrated in FIG. 2.

FIG. 7 is a block diagram of one embodiment of an accelerometer signal processor 235 which is incorporated into certain embodiments of signal processor 71. The accelerometer signal processor 235 processes signals from accelerometer array 52. Conditioned accelerometer signal path 80 is connected to an input of each of a plurality of filters 156, 160, 164, 168, 172. The filters are preferably of the bandpass type with passbands of 0.1–2 Hz, 2–3 Hz, 3–5 Hz, 7–8 Hz, and 8–13 Hz, respectively. Other passband frequency ranges may also be used. The output of each filter 156, 160, 164, 168, 172 is connected to an associated full wave rectifiers 157, 161, 165, 169, and 173, respectively. The output of each rectifier 157, 161, 165, 169, and 173 is connected to an associated envelope determiners 158, 162, 166, 170, and 174, respectively. Outputs of envelope determiners 158, 162, 166, 170, and 174 are connected to inputs of an associated threshold discriminators 159, 163, 167, 171, and 175, respectively.

Outputs of threshold discriminators 159, 163, 167, 171, 175 represent episodes of normal voluntary movement (Mv), low frequency intention tremor (Til), resting tremor (Tr), high frequency intention tremor (Tih), and physiologic tremor (Tp), respectively. These outputs are each connected to an integrator 176 and a counter 177. Integrator 176 generates outputs representative of the total activity of each of the above types of movement over at least one period of time. As noted, such a time period may be, for example, time since implementation, time since last visit to physician or health care provider, or some other time interval, weighted average of multiple time windows, or convolution of selected activities with an arbitrary time window function.

Counter 177 generates outputs representative of the number of episodes of each of the above types of movements over at least one such period of time. Outputs from integrator 176 and counter 177 are connect to an acceleration analyzer 178. Acceleration analyzer 178 calculates proportions of tremor types, such as the rest and intention types, ratios of different types of tremor activity, the level of suppression of resting tremor activity with voluntary movement, and assessment of temporal patterns of movement and acceleration. Acceleration analyzer 178 may perform some or all of these calculations, as well as other calculations, on alternative embodiments of the present invention. Acceleration-based disease state estimator 179 receives input from acceleration analyzer 178 and generates output representative of disease state based upon such input.

It should be understood that accelerometer signals may be sensed from any individual or group of body components. For example, such signals may be sensed from joints, bones, and muscles. Furthermore, such signals may be processed in any well known manner, including the determination of severity and frequency of occurrence of various tremor types. The types of tremor have been described above with respect to FIG. 5.

Figure 8:
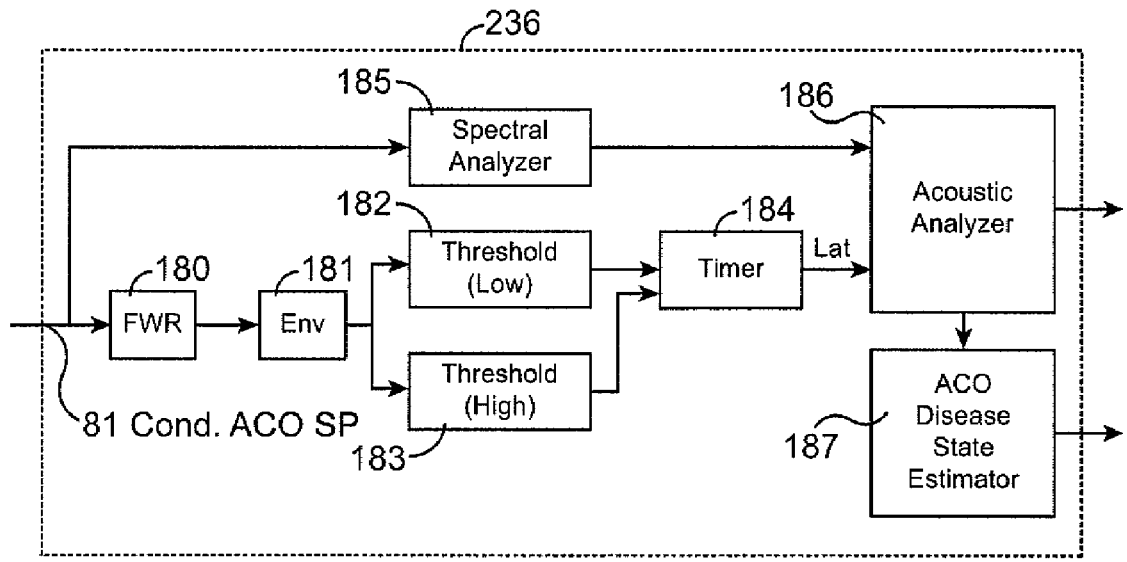
FIG. 8 is a block diagram of one embodiment of an acoustic signal processor that is included in certain embodiments of the signal processor illustrated in FIG. 2.

FIG. 8 is a block diagram of one embodiment of an acoustic signal processor 236 which is included in certain embodiments of signal processor 71. Acoustic signal processor 236 processes signals from acoustic transducer array 53. Conditioned acoustic signal path 81 is connected to a full wave rectifier 180 and a spectral analyzer 185. The output of full wave rectifier 180 is connected to an input of an envelope determiner 181, an output of which is connected to an input of a low threshold discriminator 182 and a high threshold discriminator 183. Low threshold discriminator 182 and high threshold discriminator 183 each have an output connected to an input of timer 184. Timer 184 generates an output signal representing latency (Lat) and is connected to acoustic analyzer 186. An output of acoustic analyzer 186 is connected to an input of acoustic-based disease state estimator 187. Latency (Lat) represents the latency between initiation of vocal utterance and the subsequent achievement of a threshold level of vocal amplitude. Such a vocal amplitude level is set by high threshold discriminator 183 and may represent steady state vocal amplitude or a preset or dynamically varying threshold. Latency from voice onset to achievement of steady state volume may be delayed in patients with Parkinson's disease and is calculated as a measure of disease state and response to therapy.

Acoustic analyzer 186 receives input from spectral analyzer 185. The respiratory pattern is determined from rhythmic modulation of voice and breathing sounds, sensed by elements of the acoustic transducer array 53. Irregularity and pauses in respiration as well as abnormally deep breathing patterns at rest and preceding speech are exhibited in Parkinson's disease patients. Such parameters are quantified and used as estimates of disease state and response to therapy. Respiration durations are quantified; abnormally deep respiration both during rest and preceding speech are identified and used as indicators of disease state and response to therapy. Pauses in speech and decline in speech amplitude, or fading, are additionally monitored as indicators of disease state and response to therapy. Spectral composition of speech is monitored and the change in spectral composition, reflective of changes of pharyngeal and laryngeal geometry, are quantified. Additionally, the fundamental vocal frequency; that is, the frequency at which the epiglottis vibrates, is extracted an that standard deviation of the fundamental vocal frequency is calculated over various time intervals as a quantified measure of the monotonic quality of speech characteristic of Parkinson's disease. This serves as yet another indicator of disease state and response to therapy.

Figure 9:
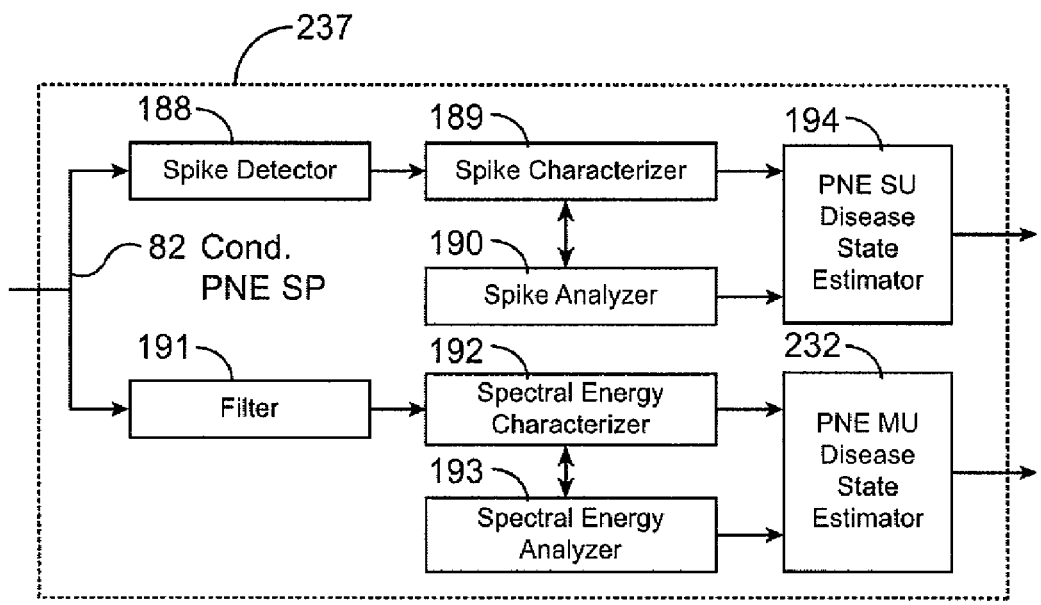
FIG. 9 is block diagram of one embodiment of a peripheral nerve electrode (PNE) signal processor 237 that is implemented in certain embodiments of signal processor 71. PNE signal

FIG. 9 is block diagram of one embodiment of a peripheral nerve electrode (PNE) signal processor 237 which is implemented in certain embodiments of signal processor 71. PNE signal processor 237 processes signals from peripheral nerve electrode array 54. These signals provided by peripheral nerve electrode array 54 are provided to PNE signal processor 237 via conditioned PNE signal path 82. Conditioned PNE signal path 82 is connected to an input of a spike detector 188 and a filter 191.

Spike detector 188 identifies action potentials. As noted, spike detection techniques are well known to those skilled in the art, and generally employ low and high amplitude thresholds. Waveforms with amplitudes greater than the low threshold and lower than the high threshold are determined to be action potentials. These thresholds may be adjusted in real-time, and the low amplitude threshold is set above the amplitude of background noise and that of nearby cells not of interest, and the high amplitude threshold is set above the amplitude of the desired action potentials to allow their passage while eliminating higher amplitude noise spikes, such as artifacts arising from electrical stimulation currents. It should be understood that bandpass, notch, and other filtering techniques may also used to improve signal to noise ratio and the sensitivity and specific of spike detectors. Individual neuron action potentials are usually recorded using fine point high-impedance electrodes, with impedances typically ranging from 1 to 5 megohms. Alternatively, larger lower-impedance electrodes may be used for recording, in which case the signals obtained typically represent aggregate activity of populations of neurons rather than action potentials from individual neurons. As noted above, peripheral nerve electrode array 54 may include such electrodes as single unit recording microelectrodes, multiple unit recording microelectrodes, intrafascicular electrodes, other intraneural electrodes, epineural electrodes, and any combination thereof.

A spike characterizer 189 determines firing patterns of individual neurons, including, for example, tonic activity, episodic activity and burst firing. Spike characterizer 189 receives the signals passed by spike detector 188 and calculates parameters that characterize the behavior of the individual and groups of neurons, the activity of which is sensed by peripheral nerve electrode array 54. Such characterization includes but is not limited to parameterization of spikes, bursts of spikes, and overall neural activity patterns. Parameterization includes but is not limited to calculation of frequencies of spikes, frequencies of bursts of spikes, interspike intervals, spike amplitudes, peak-to-valley times, valley-to-peak times, spectral composition, positive phase amplitudes, negative phase amplitudes, and positive-negative phase differential amplitudes. These parameters are described in further detail below with reference to FIG. 14. Based on this parameterization, spike characterizer 189 discriminates individual spikes and bursts originating from different neurons. The discrimination facilitates aerial monitoring of activity of individual and groups of neurons and the assessment and quantification of activity change, reflective of change in disease state and of response to therapy.

A spike analyzer 190 receives as input the parameters from spike characterizer 189, and extracts higher level information, including but not limited to average spike frequencies, average frequencies o bursts of spikes, average interspike intervals, average spike amplitudes, standard deviations thereof, trends, and temporal patterning.

Preferably, spike analyzer 190 additionally calculates the rates of change of spike parameters. From prior and current rates of change, future behaviors may be predicted. Rates of change of the parameters include but are not limited to first, second, and third time derivatives. In alternative embodiments, spike analyzer 190 additionally calculates weighted combinations of spike characteristics and performs convolutions of spike waveforms with other spike waveforms, and other preset and varying waveforms. Such operations may be performed, for example, for purposes including but not limited to autocorrelation and digital filtering.

Spike analyzer 190 may receive additional input from accelerometers, such as those described above, including head mounted accelerometer 12, proximal accelerometer 28, enclosure mounted accelerometer 36, and distal accelerometer 33. Spike analyzer 190 may receive indirect input from these or other accelerometers, as well as from conditioned or processed signals arising therefrom. Such conditioned or processed signals include, for example, the signal transmitted by conditioned accelerometer signal path 80 (FIG. 7).

Spike analyzer 190 may receive additional input from EMG arrays. As noted, such EMG arrays may include, for example, proximal EMG electrode array 45, enclosure-mounted EMG electrode array 46, and distal EMG electrode array 47. Spike analyzer 190 may also receive indirect input from these or other EMG electrode arrays, as well as from conditioned or processed signals arising therefrom. Such conditioned or processed signals include but are not limited to the signal transmitted by conditioned EMG signal path 78 (FIG. 5). These additional inputs from accelerometers and EMG arrays facilitates the characterization of neuronal firing patterns relative to activity of muscle groups and movement of joints. Such characterization may include, for example, characterization of neuronal spike amplitudes and tuning of neuronal spike frequencies to movement, including but not limited to the signal transmitted by conditioned EMG signal path 78.

The additional input from accelerometers and EMG arrays also facilitates the characterization of neuronal firing patterns relative to activity of muscle groups and movement of joints, including but not limited to characterization of neuronal spike amplitudes and tuning of neuronal spike frequencies to movement, including but not limited to movement velocity and direction. These characterizations may be used to assess functioning of the sensorimotor system, including but not limited to motor response time, and to measure the disease state and response to therapy.

Peripheral nerve electrode (PNE)-based single unit (SU) disease state estimator 194 receives an input representative of the current neuronal activity from spike characterizer 189. PNE-based single unit disease state estimator 194 may receive input representative of at least one of several signals, including desired neuronal activity, actual neuronal activity, and the difference between these quantities. The output from estimator 194 may carry a single or a plurality of signals, consistent with a representation of the disease state by a single or a multitude of state variables, respectively.

Filter 191 has an output connected to an input of spectral energy characterizer 192. Spectral energy characterizer 192 calculates the spectral composition of the signals sensed by the peripheral nerve electrode array 54. Spectral energy characterizer 192 provides outputs to each of spectral energy analyzer 193 and peripheral nerve electrode (PNE)-based multiple unit disease state estimator 232. Output of spectral energy analyzer 193 is connected to an input of PNE-based multiple unit (MU) disease state estimator 232. PNE SU disease state estimator 194 both receives input from and provides output to PNE MU disease state estimator 232.

PNE MU disease state estimator 232 receives as an input signals representative of the current neuronal activity from spectral energy characterizer 192. PNE MU disease state estimator 232 may receive input representative of at least one of several signals, including desired neuronal activity, actual neuronal activity, and the difference between these quantities. The output from PNE MU disease state estimator 232 may carry a single or a plurality of signals, consistent with a representation of the disease state by a single or a multitude of state variables, respectively.

It should be understood that inputs and outputs from each spike detector 188, spike characterizer 189, spike analyzer 190, filter 191, spectral energy characterizer 192, spectral energy analyzer 193, and PNE-based single unit disease state estimator 194, and PNE-based multiple unit disease state estimator 232 may each be comprised of individual signals or a plurality of signals. It should also be understood that each of these the units, spike detector 188, spike characterizer 189, spike analyzer 190, filter 191, spectral energy characterizer 192, spectral energy analyzer 193, and PNE-based single unit disease state estimator 194, and PNE MU disease state estimator 232 may each have different parameters and signal processing characteristics for each of the multiple signals processed. Modifications of this processing circuitry may be made to accommodate various combinations of intraneural electrodes, used for single and multiple unit recordings, and epineural electrodes, used for compound action potential recordings, without departing from the present invention.

Figure 11:
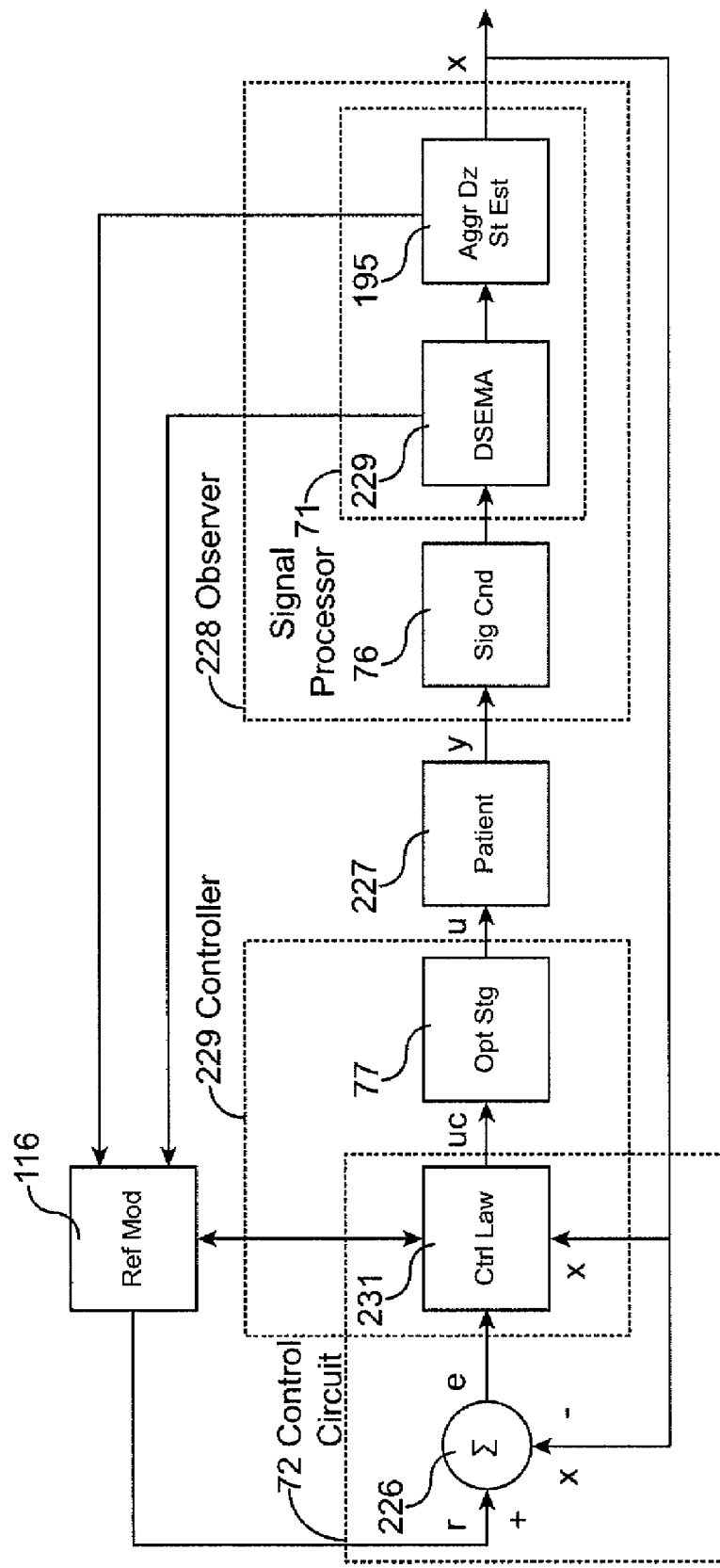
FIG. 11 is a schematic diagram of the patient-neural modulator system illustrated in FIG. 2 illustrated to show its controller and observer components.

FIG. 11 is a schematic diagram of one embodiment of a patient-neural modulator system 999 illustrated in FIG. 2 with feedback control. Patient-neural modulator system 999 primarily includes an observer 228 and a controller 229. An observer is a component of a control system that is known to those or ordinary skill in the art of control systems. An observer is a functional block in which variables, typically represented in software as parameter values or in hardware as electrical signal amplitudes, represent states of the controlled system. Such a component is used in controlling systems in which one or more of the state variables are not directly observable from the sensed signals. An observer essentially includes a simulated version of the controlled system. Its input are the same control law output signals delivered to the controlled system, and its outputs are desired to match those sensed outputs of the controlled system. The difference between the outputs of the observer and the measured outputs of the controlled system, that is, the outputs of a motor control portion of the patient's nervous system in this case, are used to calculate an observer error signal which may then be used to correct the observer error. Since the observer is implemented in software or hardware, all of its signals, including all state variables, are accessible. In a system such as the complex neural circuitry of the patient, one or more of the state variables may not be "observable", that is directly measurable or calculatable based on measured values. In such a case, the state variables present in the observer may be used as "estimates" of the actual state variables and included in the control law. The general use of "observers" for estimation of "unobservable" state variables is known to those skilled in the art of control theory. The use of observers for the estimation of neural state variables, disease states, and responses to therapy is one of the teachings of the present invention.

Observer 228 includes signal conditioning circuit 76 (FIG. 2) and signal processor 71 (FIGS. 2, 10). Signal processor 71, as noted, includes disease state estimator module array (DSEMA) 229 and aggregate disease state estimator 195. Observer 228 receives patient output "y" from patient 227. Patient output "y" is comprised of one or more signals arising from patient 227. In one preferred embodiment patient output "y" includes one or more signals from EMG electrode array 50, EEG electrode array 51, accelerometer array 52, acoustic transducer array 53, peripheral nerve electrode array 54, intracranial recording electrode array 38, and intracranial stimulating electrode array 37. It should be understood that additional signals f the same or different type may also be included.

Control circuit 72 (FIG. 2) includes summator 226 which receives an input from reference module 116, and a control law circuit block 231. Controller 229 includes the control law circuit lock 231 and output stage circuit 77. Controller 229 generates a neural modulation waveforms "u", described in detail below with reference to FIG. 13. The function and operation of each of these modules is described in detail below.

Reference disease state "r", generated by reference module 116, is a non-inverting input to summator 226, providing disease state and target reference values for the single or plurality of control laws implemented in control law circuit block 231 introduced above with reference to FIG. 2. Reference module 116 may also receive input from control circuit 72, facilitating the dynamic adjustment of reference values. Reference disease state "r" may comprise a single or plurality of signals, each of which may be zero, constant, or time-varying independent of the other. Disease state error "e" is output from summator 226 and input to controller 229. Disease state error "e", which may comprise a single or plurality of signals, represents a difference between a desired disease state (represented by reference disease state "r") and an actual disease state (represented by disease state estimate "x").

Other methods of calculating disease state estimate "x", including but not limited to linear or nonlinear combinations of reference disease state "r" and disease state estimate "x", may be employed without departing from the present invention. Controller 229 is comprised of control law circuit block 231 and output stage circuit 77.

Disease state error "e" is input to control law circuit block 231 which generates a control circuit output "uc." Control law circuit block 231 is connected to an input of output stage circuit 77. The output of the controller 229, which is generated by the output stage circuit 77, "u", is delivered to patient 227 in the form of neural modulation waveforms, described in detail below with reference to FIG. 13.

Patient output "y" is input to signal conditioning circuit 76, the output of which is connected to the input of DSEMA 229. The output of DSEMA 229 is provided to an aggregate disease state estimator 195, the output of which is the disease state estimate x. Disease state estimate x, which may be comprised of a single or plurality of signals, is an inverting input to summator 226.

Control law circuit block 231 receives disease state estimate x as an additional input, for use in nonlinear, adaptive and other control laws. Reference module 116 receives input from DSEMA 229 and aggregate disease state estimator 195 for use in dynamically determining reference disease state r. Other modifications, including substitutions, additions, and deletions, may be made to the control loop without departing from the present invention.

Control law circuit block 231 has an autocalibration mode in which multivariable sweeps through stimulation parameters and stimulating electrode configurations are performed to automate and expedite parameter and configuration optimization. This autocalibration feature enables rapid optimization of treatment, eliminating months of iterations of trial and error in optimizing stimulation parameters and electrode configuration necessitated by the prior technique of constant parameter stimulation. Additionally, this autocalibration feature permits real-time adjustment and optimization of stimulation parameters and electrode configuration. This is particularly useful to overcome increases in electrode impedance which result from the body's normal response to implanted foreign bodies in which a fibrotic capsule is commonly formed around the electrodes. Effects of shifts in electrode position relative to a target structures may be minimized by said autocalibration feature. Detection of changes in electrode impedance and position are facilitated by autocalibration feature. The autocalibration feature facilitates detection of changes in electrode impedance and position. Notification of patient and health care provider allows proactive action, including automated or manual adjustment of treatment parameters and advance knowledge of impending electrode replacement needs.

Figure 12:
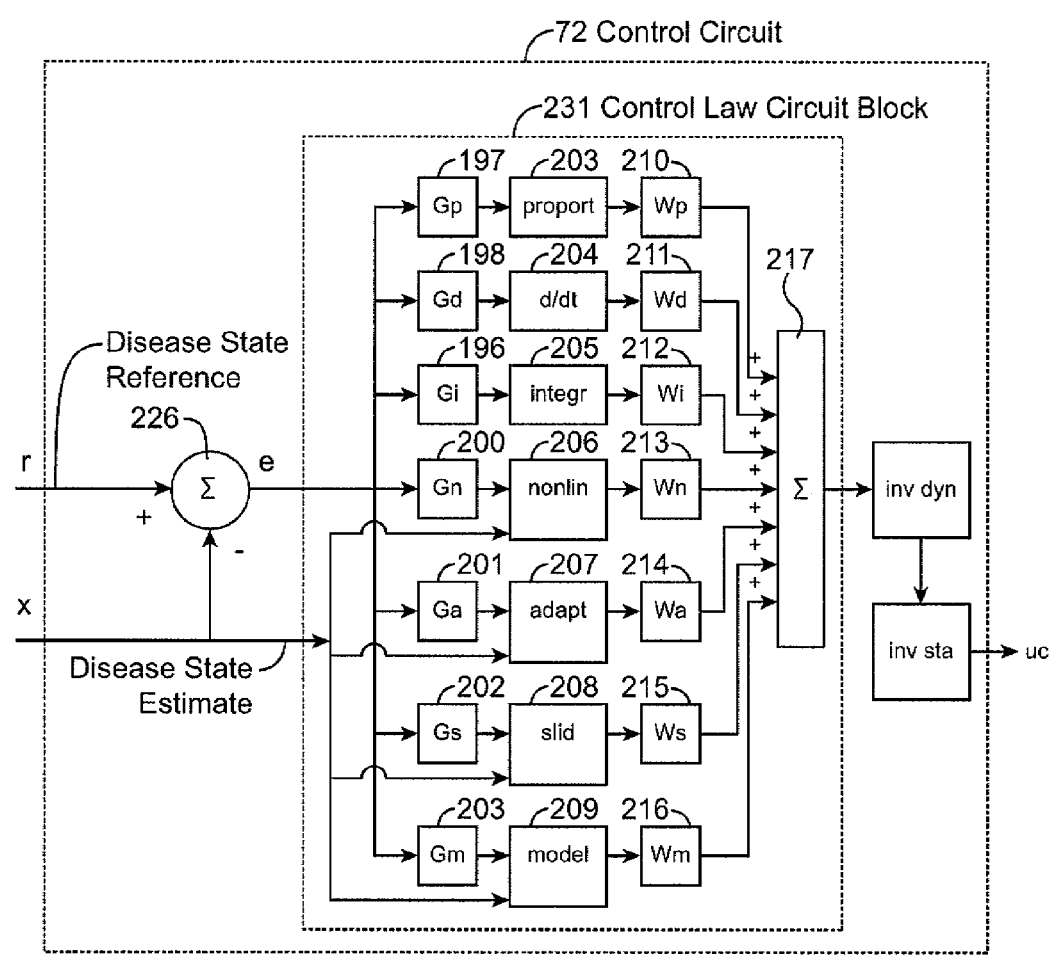
FIG. 12 is a schematic diagram of one embodiment of the control circuit illustrated in FIG. 2.

FIG. 12 is a schematic diagram of control circuit 72. As noted, control circuit 72 comprises control laws circuit block 231 and summator 226. Disease state error "e" is input to gain stages of control laws, including but not limited to at least one of proportional gain 197, differential gain 198, integral gain 199, nonlinear gain 200, adaptive gain 201, sliding gain 202, and model reference gain 203.

An output of each of these gain stages is connected to what is referred to herein as control law stages. In the illustrative embodiment, control law stages includes proportional controller 230, differential controller 204, integral controller 205, nonlinear controller 206, adaptive controller 207, sliding controller 208, and model reference controller 209, respectively.

Outputs of these control law stages are connected to weight stages, including proportional controller weight 210, differential controller weight 211, integral controller weight 212, nonlinear controller weight 213, adaptive controller weight 214, sliding controller weight 215, and model reference controller weight 216. Outputs of the weight stages are noninverting inputs to summator 217, the output of which is control circuit output "uc". The weight stages may be any combination of at least one of constant, time varying, and nonlinear without departing from the present invention.

Disease state estimate x is input to nonlinear controller 206, adaptive controller 207, sliding controller 208, and model reference controller 209. The control laws depicted are representative of one possible implementation; numerous variations, including substitutions, additions, and deletions, may be made without departing from the present invention.

The present invention optimizes the efficiency of energy used in the treatment given to the patient by minimizing to a satisfactory level the stimulation intensity to provide the level of treatment magnitude necessary to control disease symptoms without extending additional energy delivering unnecessary overtreatment. In the definition of the control law, a command input or reference input (denoted as r in FIGS. 11 and 12) specifies the target disease state. In the preferred embodiment, r specifies the target amplitude of tremor. The control law generates an electrical stimulation magnitude just sufficient to reduce the patient's tremor to the target value. With this apparatus and method, the precise amount of electrical energy required is delivered, and overstimulation is avoided. In present stimulation systems, a constant level of stimulation is delivered, resulting in either of two undesirable scenarios when disease state and symptoms fluctuate: (1) undertreatment, i.e. tremor amplitude exceeds desirable level or (2) overtreatment or excess stimulation, in which more electrical energy is delivered than is actually needed. In the overtreatment case, battery life is unnecessarily reduced. The energy delivered to the tissue in the form of a stimulation signal represents a substantial portion of the energy consumed by the implanted device; minimization of this energy substantially extends battery life, with a consequent extension of time in between reoperations to replace expended batteries.

Figure 13:
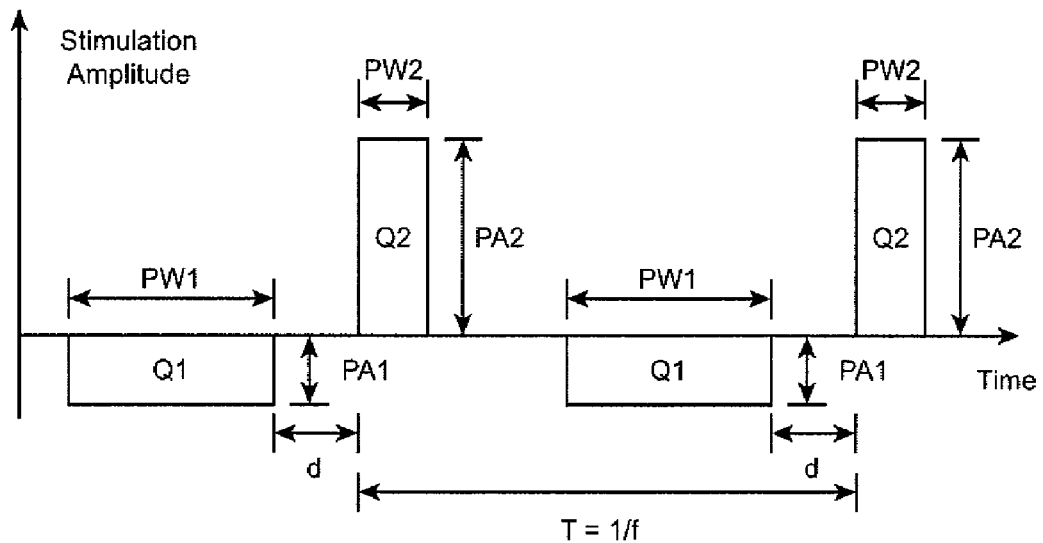
FIG. 13 is a schematic diagram of electrical stimulation waveforms for neural modulation.

FIG. 13 is a schematic diagram of electrical stimulation waveforms for neural modulation. The illustrated ideal stimulus waveform is a charge balanced biphasic current controlled electrical pulse train. Two cycles of this waveform are depicted, each of which is made of a smaller cathodic phase followed, after a short delay, by a larger anodic phase. In one preferred embodiment, a current controlled stimulus is delivered; and the "Stimulus Amplitude" represents stimulation current. A voltage controlled or other stimulus may be used without departing from the present invention. Similarly, other waveforms, including an anodic phase preceding a cathodic phase, a monophasic pulse, a triphasic pulse, or the waveform may be used without departing from the present invention.

The amplitude of the first phase, depicted here as cathodic, is given by pulse amplitude 1 PA1; the amplitude of the second phase, depicted here as anodic, is given by pulse amplitude 2 PA2. The durations of the first and second phases are pulse width 1 PW1 and pulse width 1 PW2, respectively. Phase 1 and phase 2 are separated by a brief delay d. Waveforms repeat with a stimulation period T, defining the stimulation frequency as f=1/T.

The area under the curve for each phase represents the charge Q transferred, and in the preferred embodiment, these quantities are equal and opposite for the cathodic (Q1) and anodic (Q2) pulses, i.e. Q=Q1=Q2. For rectangular pulses, the charge transferred per pulse is given by Q1=PA1*PW1 and Q2=PA2*PW2. The charge balancing constraint given by−Q1=Q2 imposes the relation PA1*PW1=−PA2*PW2. Departure from the charge balancing constraint, as is desired for optimal function of certain electrode materials, in included in the present invention.

The stimulus amplitudes PA1 and PA2, durations PW1 and PW2, frequency f, or a combination thereof may be varied to modulate the intensity of the said stimulus. A series of stimulus waveforms may be delivered as a burst, in which case the number of stimuli per burst, the frequency of waveforms within the said burst, the frequency at which the bursts are repeated, or a combination thereof may additionally be varied to modulate the stimulus intensity.

Typical values for stimulation parameters include f=100–300 Hz, PA1 and PA2 range from 10 microamps to 10 milliamps, PW1 and PW2 range from 50 microseconds to 100 milliseconds. These values are representative, and departure from these ranges is included in the apparatus and method of the present invention.

FIG. 14 is a schematic diagram of one example of the recorded waveforms. This represents an individual action potential from a single cell recording, typically recorded from intracranial microelectrodes. Aggregates of multiple such waveforms are recorded from larger intracranial electrodes. The action potentials may be characterized according t a set of parameters including but not limited to time to valley 1 TV1, time to peak 1 TP1, time to valley 2 TV2, amplitude of valley 1 AV1, amplitude of peak 1 AP1, amplitude of valley 2 AV2, and algebraic combinations and polarity reversals thereof.

When recording activity from more than one cell, said characterization facilitates discrimination of waveforms by individual recorded cell. The discrimination allows activity of a plurality of cells to be individually followed over time. The parameterization may be performed separately on signals recorded from different electrodes. Alternatively, said parameterization may be performed on signals pooled from multiple electrodes.

Following is a description of a general form for representing disease state.

Disease State DS is a vector of individual disease states, including intrinsic disease states DSI and extrinsic disease states DSE:

$$DS=[DS_I DS_E]$$

Intrinsic disease states and extrinsic disease states are, themselves vectors of individual disease states:

$$DS_I=[DS_{I1} DS_{I2} DS_{I3} \ldots DS_{IN}]$$

$$DS_E=[DS_{E1} DS_{E2} DS_{E3} \ldots DS_{EM}]$$

Intrinsic Disease States include those disease states which characterize the state of disease at a given point in time. Extrinsic Disease States include variations of intrinsic disease states, including but not limited to cyclical variations in Intrinsic Disease States, variations in Intrinsic Disease States which occur in response to external events, and variations in Intrinsic Disease States which occur in response to levels of and changes in levels of electrical stimulation. Said external events include but are not limited to pharmacologic dosing, consumption of meals, awakening, falling asleep, transitioning from Parkinsonian "on" state to Parkinsonian "off" state, transitioning from Parkinsonian "off" state to Parkinsonian "on" state.

Each of Intrinsic Disease States and Extrinsic Disease States include but are not limited to those defined herein; additional disease states and definitions thereof may be added without departing from the present invention.

The first intrinsic disease state $DS_{I1}$ represents the level of resting tremor $$DS_{I1} = RT_N$$

Where Normalized Resting Tremor Magnitude $RT_N$ is given by:

$$RT_N = T_{A,3-5}*W_{TA,3-5} + T_{E,3-5}*W_{TE,3-5} + T_{P,3-5}*W_{PE,3-5} + T_{C,3-5}+W_{TC,3-5}+T_{N,3-5}*W_{TN,3-5}+T_{S,3-5}*W_{TS,3-5}+T_{E,3-5}*W_{TE,3-5}$$

Where the factors from which the Resting Tremor Magnitude $RT_N$ is determined, representing estimates of the magnitude of 3–5 Hertz movement of selected body segments, including but not limited to limbs, torso, and head are:

$T_{A,3-5}$=Tremor level determined by acceleration monitoring
$W_{TA,3-5}$=Weighting factor for tremor $T_{A,3-5}$
$T_{E,3-5}$=Tremor level determined by electromyographic (EMG) monitoring
$W_{TE,3-5}$=Weighting factor for tremor $T_{E,3-5}$
$T_{P,3-5}$=Tremor level determined by peripheral nerve electrode monitoring
$W_{TP,3-5}$=Weighting factor for tremor $T_{P,3-5}$
$T_{C,3-5}$=Tremor level determined by cortical electrode monitoring
$W_{TC,3-5}$=Weighting factor for tremor $T_{C,3-5}$
$T_{N,3-5}$=Tremor level determined by neural monitoring, including subcortical nuclei, white matter tracts, and spinal cord neurons
$W_{TN,3-5}$=Weighting factor for tremor $T_{N,3-5}$
$T_{S,3-5}$=Tremor level determined by acoustic sensor monitoring
$W_{TS,3-5}$=Weighting factor for tremor $T_{S,3-5}$ Weighting factors are adjusted after implantation to achieve normalization of $RT_N$ and to allow for selective weighting of tremor levels as determined from signals arising from various sensors, including but not limited to those listed.

These calculations may be implemented in analog hardware, digital hardware, software, or other form. In the preferred embodiment, values are implemented as 16-bit variables; ranges for said weighting factors and tremor levels are 0 to 65535. These ranges may be changed or implemented in analog form without departing from the present invention.

The second intrinsic disease state $DS_{I2}$ represents the level of dyskinesia:

$$DS_{I2} = D_N$$

Where Normalized Dyskinesia Magnitude $D_N$ is given by:

$$D_N = D_A*W_{DA} + T_E*W_{TE} + T_P*W_{PE} + T_C + W_{TC} + T_N*W_{TN} + T_S*W_{TS} + T_E*W_{TE}$$

Where
$D_{A,3-5}$=Dyskinesia level determined by acceleration monitoring
$W_{DA,3-5}$=Weighting factor for Dyskinesia $D_{A,3-5}$
$D_{E,3-5}$=Dyskinesia level determined by electromyographic (EMG) monitoring
$W_{DE,3-5}$=Weighting factor for Dyskinesia $D_{E,3-5}$
$D_{P,3-5}$=Dyskinesia level determined by peripheral nerve electrode monitoring
$W_{DP,3-5}$=Weighting factor for Dyskinesia $D_{P,3-5}$
$D_{C,3-5}$=Dyskinesia level determined by cortical electrode monitoring
$W_{DC,3-5}$=Weighting factor for Dyskinesia $D_{C,3-5}$
$D_{N,3-5}$=Dyskinesia level determined by neural monitoring, including subcortical nuclei, white matter tracts, and spinal cord neurons
$W_{DN,3-5}$=Weighting factor for Dyskinesia $D_{N,3-5}$
$D_{S,3-5}$=Dyskinesia level determined by acoustic sensor monitoring
$W_{DS,3-5}$=Weighting factor for Dyskinesia $D_{S,3-5}$ The third intrinsic disease state $DS_{I3}$ represents the level of rigidity.

$$DS_{I3} = R_N$$

Where Normalized Rigidity Magnitude $R_N$ is given by:

$$R_N = R_A*W_{RA} + R_E*W_{RE} + R_P*W_{RE} + R_C + W_{RC} + R_N*W_{RN} + R_S*W_{RS} + R_E*W_{RE}$$

Where
$R_{A,3-5}$=Rigidity level determined by acceleration monitoring
$W_{RA,3-5}$=Weighting factor for Rigidity $R_{A,3-5}$
$R_{E,3-5}$=Rigidity level determined by electromyographic (EMG) monitoring
$W_{RE,3-5}$=Weighting factor for Rigidity $R_{E,3-5}$
$R_{P,3-5}$=Rigidity level determined by peripheral nerve electrode monitoring
$W_{RP,3-5}$=Weighting factor for Rigidity $R_{P,3-5}$
$R_{C,3-5}$=Rigidity level determined by cortical electrode monitoring
$W_{RC,3-5}$=Weighting factor for Rigidity $R_{C,3-5}$
$R_{N,3-5}$=Rigidity level determined by neural monitoring, including subcortical nuclei, white matter tracts, and spinal cord neurons
$W_{RN,3-5}$=Weighting factor for Rigidity $R_{N,3-5}$
$R_{S,3-5}$=Rigidity level determined by acoustic sensor monitoring
$W_{RS,3-5}$=Weighting factor for Rigidity $R_{S,3-5}$ The fourth intrinsic disease state $DS_{I4}$ represents the level of bradykinesia.

$$DS_{I4} = B_N$$

Where Normalized Bradykinesia Magnitude $B_N$ is given by:

$$B_N = B_A*W_{BA} + B_E*W_{BE} + B_P*W_{PE} + B_C + W_{BC} + B_N*W_{BN} + B_S*W_{BS} + B_E*W_{BE}$$

Where
$R_A$=Bradykinesia level determined by acceleration monitoring
$W_{RA}$=Weighting factor for Bradykinesia $R_A$
$R_E$=Bradykinesia level determined by electromyographic (EMG) monitoring
$W_{RE}$=Weighting factor for Bradykinesia $R_E$
$R_P$=Bradykinesia level determined by peripheral nerve electrode monitoring
$W_{RP}$=Weighting factor for Bradykinesia $R_P$
$R_C$=Bradykinesia level determined by cortical electrode monitoring
$W_{RC}$=Weighting factor for Bradykinesia $R_C$
$R_N$=Bradykinesia level determined by neural monitoring, including subcortical nuclei, white matter tracts, and spinal cord neurons
$W_{RN}$=Weighting factor for Bradykinesia $R_N$ $R_S$=Bradykinesia level determined by acoustic sensor monitoring $W_{RS}$=Weighting factor for Bradykinesia $R_S$ The control law drives these disease states toward their reference values, nominally 0, according to a vector of weights, establishing a prioritization.

Side effects and other parameters, such as power consumption and current magnitude, are also quantified and minimized according to a cost function.

One advantage of the present invention is that it provides prediction of future symptomatology, cognitive and neuromotor functionality, and treatment magnitude requirements. Such predictions may be based on preset, learned and real-time sensed parameters as well as input from the patient, physician or other person or system. The prediction of future symptomatology is based upon any of several weighted combination of parameters. Based upon prior characterization of the circadian fluctuation in symptomatology (that is, tremor magnitude for deep brain stimulation or level of depression for stimulation of other sites including locus ceruleus), future fluctuations may be predicted. An estimate, or model, of fluctuation may be based upon a combination of preset, learned, and real-time sensed parameters. Preset parameters are derived from clinical studies designed specifically for the purpose of gathering such data, or from estimates extracted from data gleaned from published literature. Real-time sensed parameters are derived from the current states (and changes, i.e. derivatives and other processed signals, thereof) of sensed and processed signals. Learned parameters are based upon the time histories of previously sensed signals. For example, the circadian fluctuation in tremor amplitude may be sensed; a weighted average of this data collected over numerous prior days provides as estimate of the expected tremor amplitude as well as a standard deviation and other statistical parameters to characterize the anticipated tremor amplitude. Similarly, in the presence of closed-loop feedback, the level of stimulation required to reduce or eliminate tremor may be used as an estimate of the "amplitude" or state of the underlying disease.

Another advantage of the present invention is that it performs automated determination of the optimum magnitude of treatment—by sensing and quantifying the magnitude and frequency of tremor activity in the patient, a quantitative representation of the level or "state" of the disease is determined. The disease state is monitored as treatment parameters are automatically varied, and the local or absolute minimum in disease state is achieved as the optimal set of stimulation parameters is converged upon. The disease state may be represented as a single value or a vector or matrix of values; in the latter two cases, a multivariable optimization algorithm is employed with appropriate weighting factors.

Having now described several embodiments of the invention, it should be apparent to those skilled in the art that the foregoing is merely illustrative and not limiting, having been presented by way of example only. For example, all signal paths may transmit a single or plurality of signals without departing from the present invention. Numerous modifications and other embodiments are within the scope of one of ordinary skill in the art and are contemplated as falling within the scope of the invention as defined by the appended claims.

Current implanted neurostimulators suffer from limited battery life necessitating replacement. The original filing of this invention teaches a closed-loop technique which allows lower average power delivery, providing extended batter life. A further improvement is taught in the present invention. The present invention teaches a novel form of power delivery, in which electromagnetic power is provided externally and radiated transcutaneously through the skin 382 to the implanted circuit.

A multiplicity of electromagnetic coils is used, to provide electromagnetic fields of multiple non-collinear orientations. The purpose of this design is to overcome fluctuations and interruptions in power that otherwise occur when the implanted circuit moves along with the body parts relative to electromagnetic coils.

An additional improvement is taught in the application of time multiplexing of signals delivered by said multiplicity of electromagnetic coils. Multiplexing signals in time from a multiplicity of coils allows electromagnetic energy to be delivered at a multiplicity of spatial orientations without mutual interference between fields. In one embodiment, three coils are positioned such that they are mutually orthogonal. Regardless of the orientation of the implanted circuit, mutual coupling between the implanted circuit and at least one element of the coil array will facilitate power transmission.

The present invention further includes an embodiment in which the coils are embedded in a flexible cloth assembly, including but not limited to a pillow, bandana, hat, or other accessory or piece of apparel.

Additionally, low profile mounting of the neurological control system 999 is taught, including a design in which the device is implanted entirely adjacent to the head, avoiding the subcutaneous cables plaguing current designs with high failure and fracture rates. Additionally, a low-profile design is taught in which the neurological control system is implanted beneath the skin and recessed in the calvarum.

Figure 16:
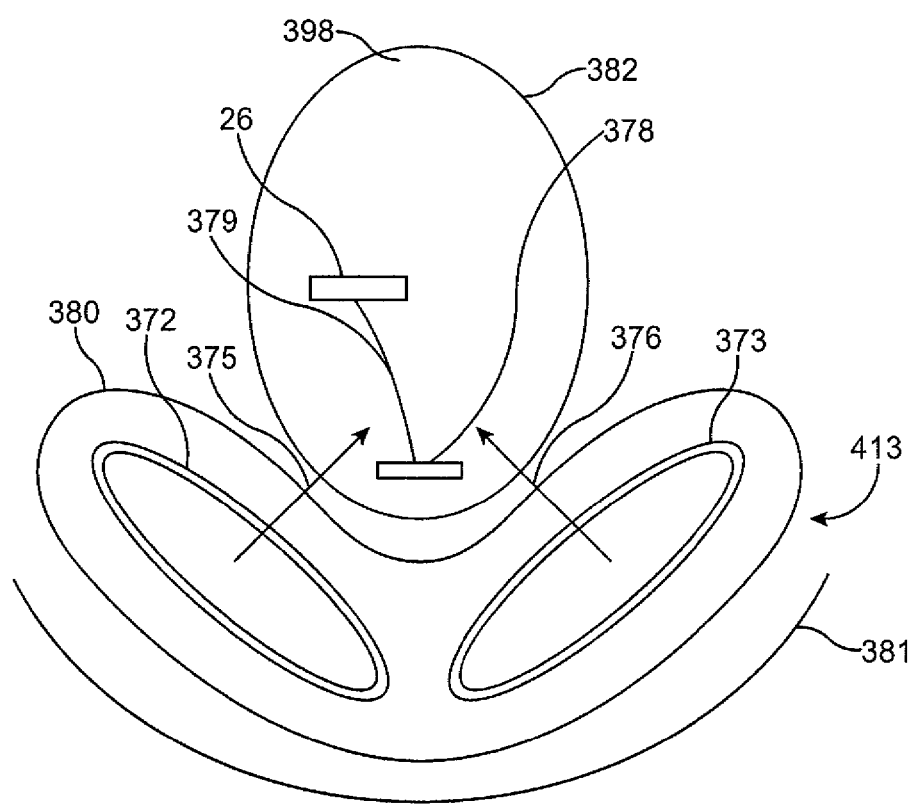
FIG. 16 is a diagram of a two coil embodiment of the power delivery unit.
Figure 18:
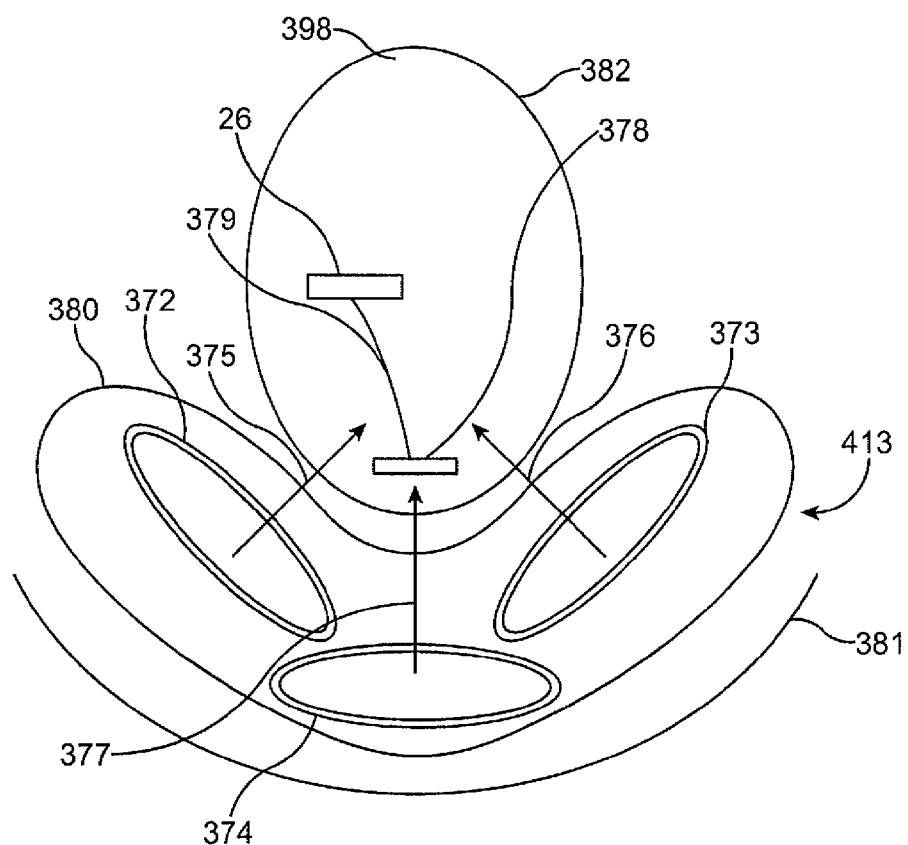
FIG. 18 is a diagram of a three coil embodiment of the power delivery unit.

FIG. 16 and FIG. 18 show two coil and three coil embodiments, respectively, of power delivery unit 413. Different numbers of coils may be used without departing from the present invention. Each of electromagnetic coil 372, 373, 374 radiates electromagnetic power, represented by magnetic flux 375, 376, 377, which radiates through the skin 382 and is then converted to electrical energy by power conversion unit 378. Power is then transmitted from power conversion unit 378 via power cable 379 to stimulating and recording circuit 26, a component of the neurological control system 999.

A single or multiplicity of coil holder 380 holds electromagnetic coil 372, 373, 374 in place. Coil holder 380 may be placed atop bedding 381, which may include a pillow, blanket, or mattress. Alternatively, coil holder 380 may be placed below bedding 381, which may include a pillow, blanket, mattress, or other element.

Figure 17:
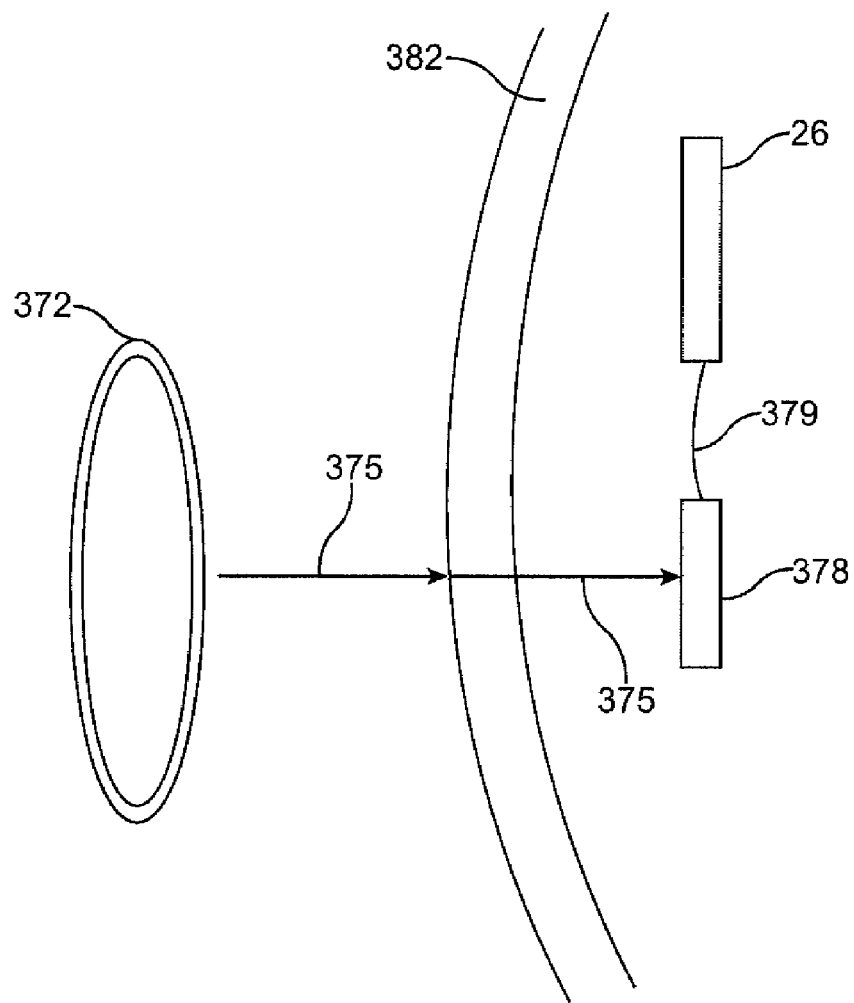
FIG. 17 is a magnification of the configurations of FIGS. 16 and 18 showing the magnetic flux penetrating the skin.

FIG. 17 shows this configuration at greater magnification, in which magnetic flux 375 is seen to penetrate skin 382.

Figure 19:
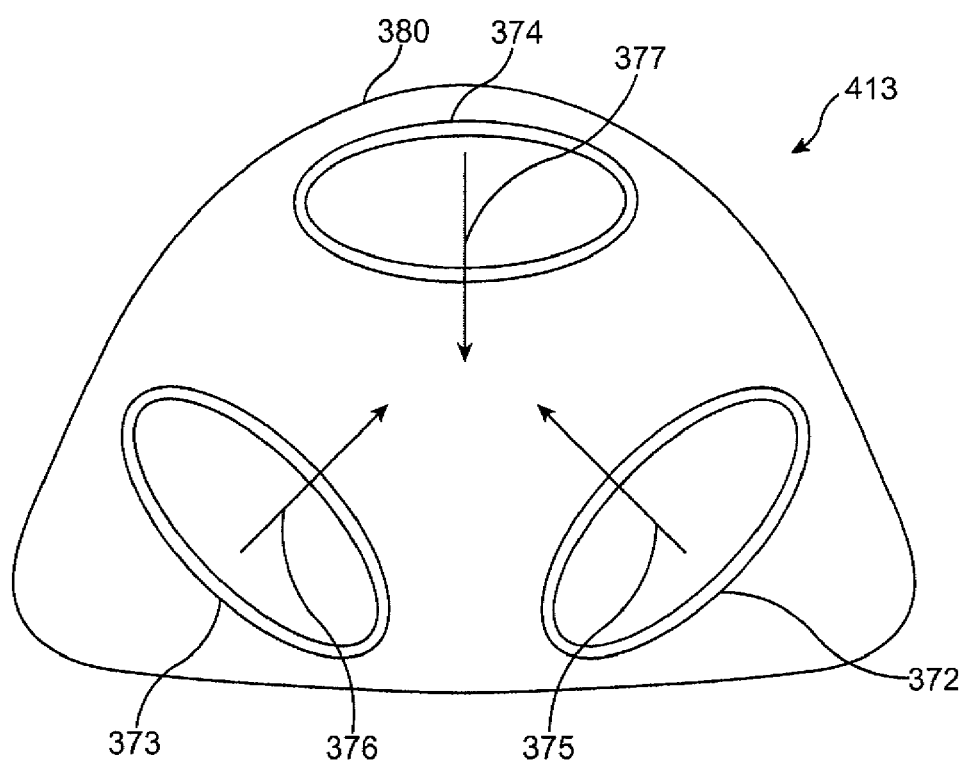
FIG. 19 is a diagram of the power delivery unit with coil holder.

FIG. 19 depicts power delivery unit 413 with coil holder 380 shown holding electromagnetic coil 372, 373, 374 in place, as seen from above. In this design, all electromagnetic coils 372, 373, 374 are contained within coil holder 380. For illustrative purposes, coil holder 380 is shown in this embodiment as a convex shape. Other shapes may be used without departing from the present invention.

Figure 20:
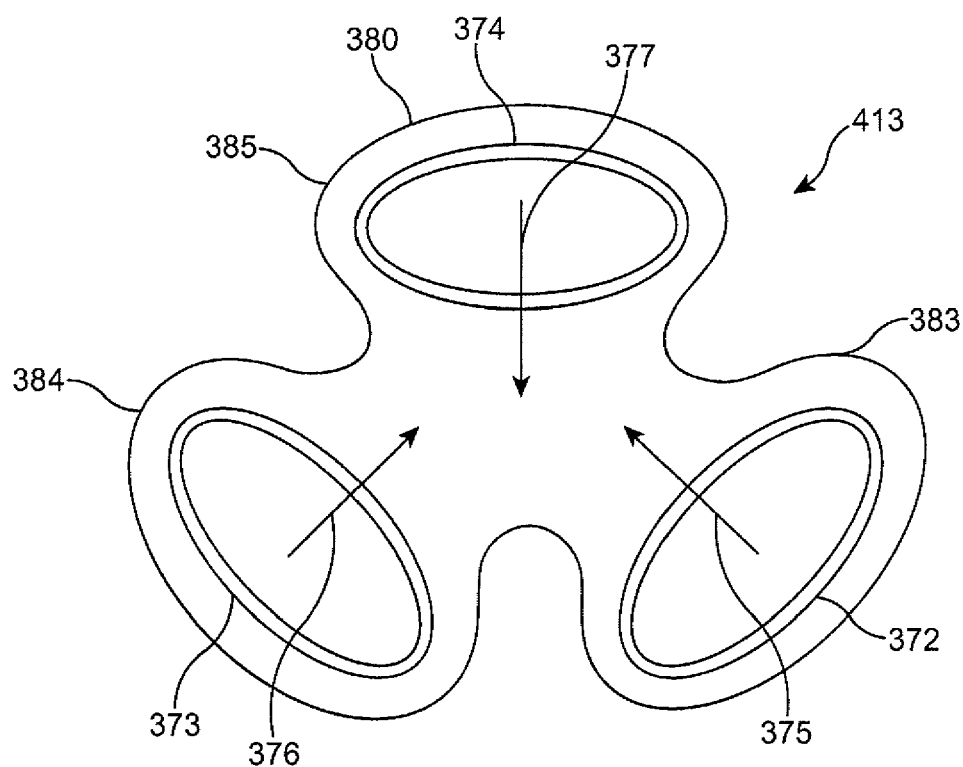
FIG. 20 is a diagram of the coil holder.

FIG. 20 shows coil holder 380 with electromagnetic coil 372, 373, 374 in place, as seen from above. In this design, all electromagnetic coils 372, 373, 374 are contained within coil holder 380, and could holder 380 has For illustrative purposes, coil holder 380 is shown in this embodiment as a multi-lobed shape, with electromagnetic coil 372, 373, 374 contained within coil pockets 383, 384, 385, respectively. Other shapes may be used without departing from the present invention.

Electromagnetic coils 372, 373, 374 may be permanently affixed within coil holder 380. Alternatively, electromagnetic coils 372, 373, 374 may be removable form coil holder 380 to facilitate cleaning or laundering of coil holder 380.

Further, use of electromagnetic fields, as direct modulators of neural activity is taught in the present invention. [This also references provisional application filed Jul. 29, 2002.]

Figure 21:
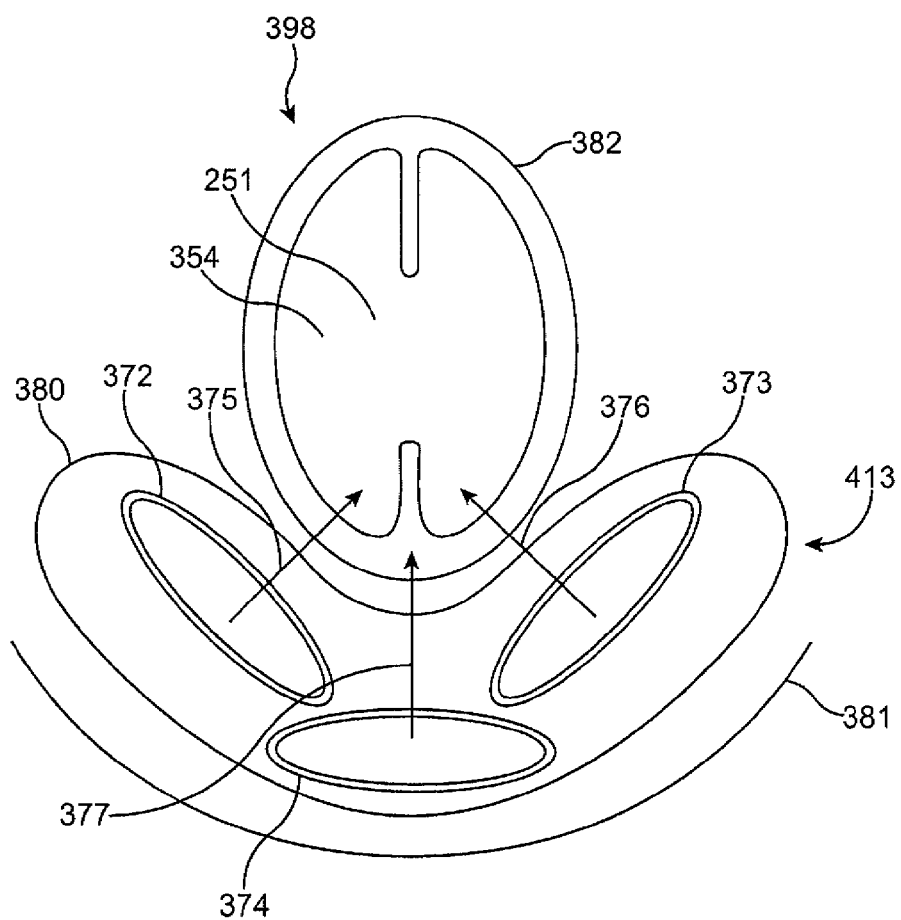
FIG. 21 is a diagram of the electromagnetic copies in proximity to the head of a patient.

As shown in FIG. 21, electromagnetic coils 372, 373, 374 may be positioned by coil holder 380 to lie in close proximity to the head 398 of a patient. Magnetic flux 375, 376, 377, which radiate through the skin 382 penetrate into underlying brain 251, or other neural tissue 354, and generate electrical currents. Said electrical currents serve to stimulate or inhibit neural activity. Other neural tissue includes but is not limited to brain 251, brainstem, spinal cord, peripheral nerves, cranial nerves, neurosensory organs, and other structures.

Figure 22:
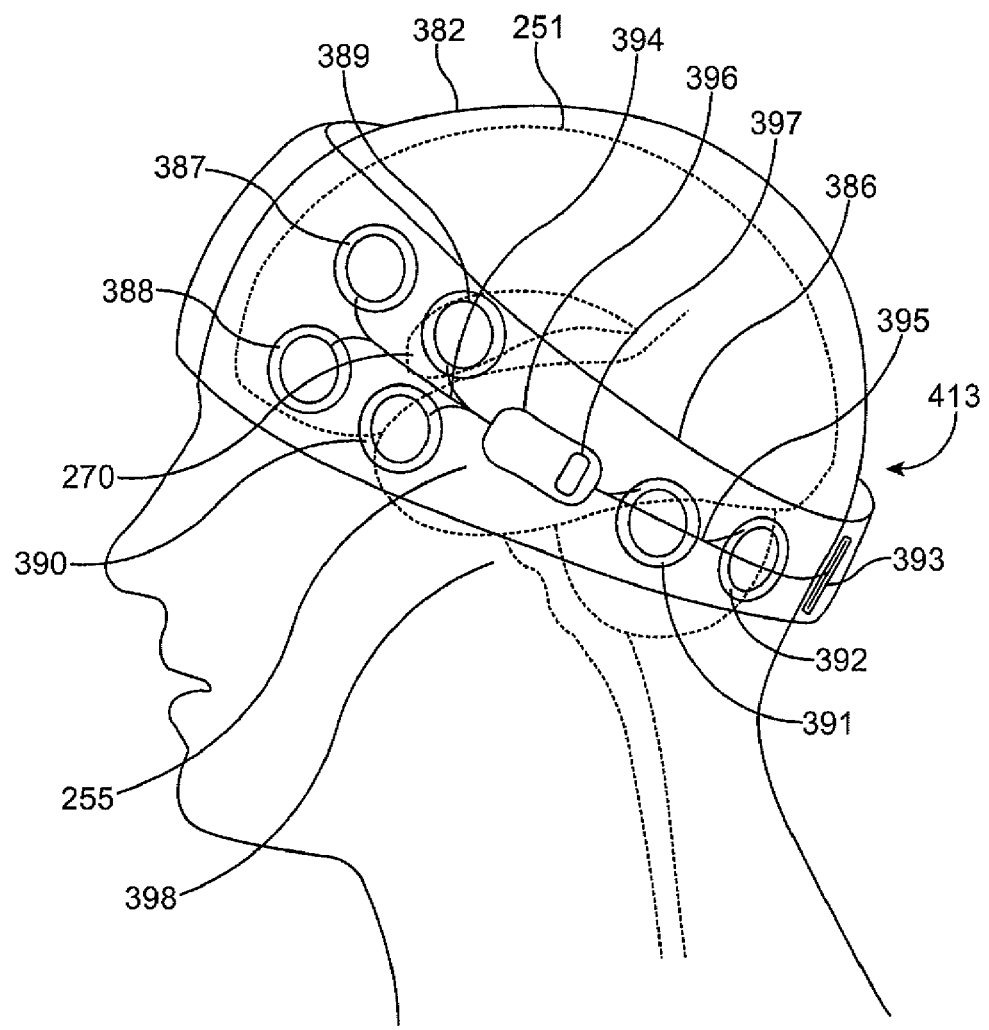
FIG. 22 is a diagram of multiple coil embodiments.

FIG. 22 shows multiple coil embodiments. Different numbers of coils may be used without departing from the present invention. FIG. 22 shows a distributed arrangement of coils, to facilitate strong signal coupling with a minimum of tissue heating or sensory stimulation. Brain 251 is shown underlying skin 382 in head 398. Temporal cortex 255 and thalamus 270 are shown.

Headband coil holder 386 is in mechanical connection with each of electromagnetic coils 387, 388, 389, 390, 391, 392, 393, which radiate electromagnetic power through the skin 382. This is then converted to electrical energy by power conversion unit 378, which is implanted in any of several locations, shown in FIG. 17 and FIG. 18, omitted here for diagram clarity. As shown in FIG. 17, power is then transmitted from power conversion unit 378 via power cable 379 to stimulating and recording circuit 26, a component of the neurological control system 999.

Power source 397 provides power to power modulator 396, which modulates power on a carrier frequency and is electrically connected via electromagnetic coil cable 394 to electromagnetic coils 387, 388, 389, 390 which radiate power through skin 382. Power modulator 396 is also electrically connected via electromagnetic coil cable 395 to electromagnetic coils 391, 392, 393 which radiate power through skin 382. Electromagnetic coils 387, 388, 389, 390, 391, 392, 393 can be arranged in a different geometrical or anatomical configuration, with the same, a higher or a lower number of electromagnetic coils, without departing from the present invention. Electromagnetic coils 387, 388, 389, 390, 391, 392, 393 may alternatively be affixed to a different form of apparel, clothing, or fixture without departing from the present invention. Such embodiments include a hat, cap, bandana, or other device.

Figure 23:
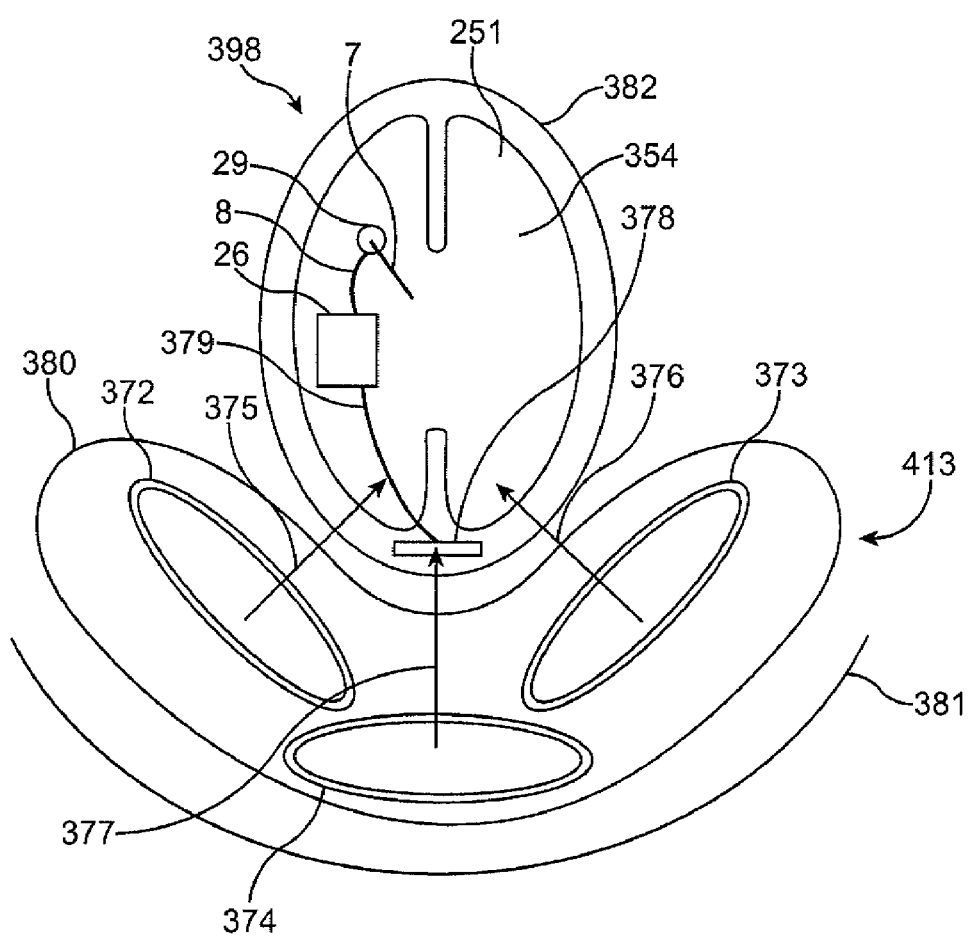
FIG. 23 is a diagram of the paracranial design, with implanted components in close proximity to the patient's head.

FIG. 23 shows the paracranial design, with implanted components in close proximity to the head 398. This design eliminates the pervasive problem of moving parts, inherent in all current technology devices. All cabling is in close approximation to the calvarum, a rigid structure; therefore all implanted parts remain stationary. Since no implanted parts are subjected to movement, they are at: greatly reduced risk for mechanical fatigue, the single highest failure mode for current implanted neuromodulators. This innovation dramatically reduces the frequency and likelihood for re-operation to repair broken implanted components, a major concern in all patients and particularly the elderly, who are often poor operative candidates, and who are at highest risk for many of the neurological and neurodegenerative diseases amenable to treatment by neuromodulation.

FIG. 23 depicts an embodiment in which the head 398 of the patient lies atop coil holder 380, placing the power conversion unit 378 within at least one of magnetic flux 375, 376, 377. Power conversion unit 378 converts power transmitted as magnetic flux 375, 376, 377 into electrical energy, which is transmitted by power cable 379 to stimulating and recording circuit 26, a component of the neurological control system 999. Stimulating and recording circuit 26 generates neuromodulation signal that is transmitted via connecting cable 8 to intracranial stimulating electrode array 37, depicted in more detail in FIG. 1, which deliver neuromodulation signal to brain 251. or other neural tissue 354. Connecting cable 8 furthermore provides bi-directional electrical connection between intracranial electrodes 246 and stimulating and recording circuit 26, a component of neurological control system 999.

Catheter anchor 29 is in mechanical communication with intracranial catheter 7. and secures it to calvarum 9. Intracranial electrodes 246 are mounted on or incorporated into intracranial catheter 7.

Figure 24:
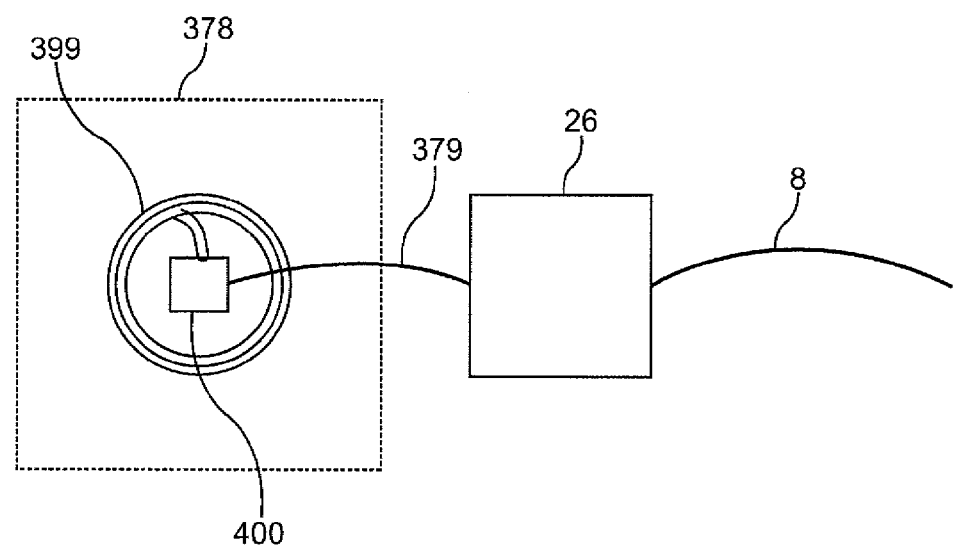
FIG. 24 is a diagram of the power conversion unit that includes the electromagnetic coupling element.

FIG. 24 shows power conversion unit 378 includes electromagnetic coupling element 399, such as a wire coil, circuit board tracing coil, or equivalent implementation. In one embodiment, power conversion unit 378 also includes power conversion circuit 400, which converts electrical signal induced by any of magnetic flux 375, 376, 377, on electromagnetic coupling element 399, into at least one of electrical power and electrical signal, which are transmitted via power cable 379 to stimulating and recording circuit 26, which generates neuromodulation signal 412, which is transmitted on connecting cable 8. to intracranial catheter 7.

Power conversion circuit 400 includes rectifier 401, energy storage element 402, regulator 403, filter 404, demodulator 405, and amplifier 406. Electromagnetic coupling element 399 is electrically connected via electromagnetic coupling element cable 407 to power conversion circuit 400.

Either of magnetic flux 375, 376, 377 passing through electromagnetic coupling element 399 induces induced current 408, which is transmitted via electromagnetic coupling element cable 407 to power conversion circuit 400. Induced current 408 is rectified by rectifier 401 to a direct current form and is stored or lowpass filtered by energy storage element 402 and regulated by regulator 403 and then transmitted as regulated power 409 by power cable 379 to stimulating and recording circuit 26, a component of neurological control system 999.

Figure 25:
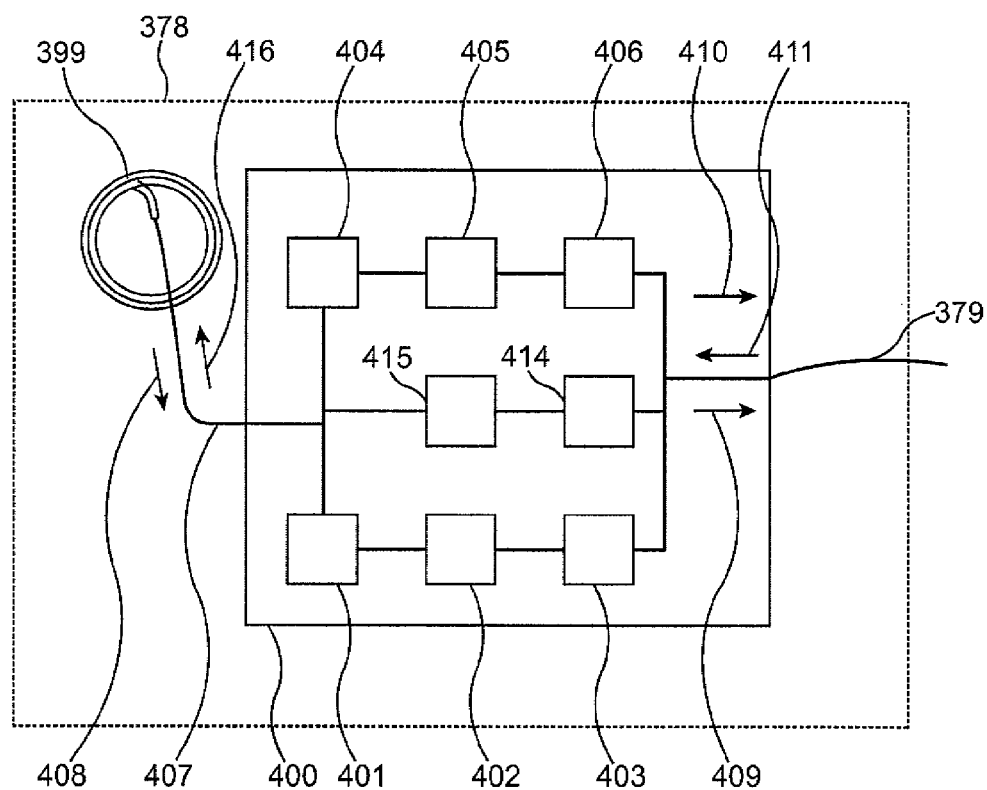
FIG. 25 is a diagram of the power conversion circuit.

FIG. 25 shows the communication circuit. This circuit also provides bi-directional communication with external devices, including power delivery unit 413 as well as with patient interface module 55 and supervisory module 56, shown in FIG. 1.

Either of magnetic flux 375, 376, 377 passing through electromagnetic coupling element 399 induces induced current 408, which is transmitted via electromagnetic coupling element cable 407 to power conversion circuit 400. Induced current 408 is filtered by filter 404, then demodulated by 405, then amplified by amplifier 406, then transmitted as incoming data stream 410 via power cable 379 to stimulating and recording circuit 26. At least one of digital to analog or analog to digital conversion may also be performed without departing from the present invention.

Outgoing data stream 411 is transmitted from stimulating and recording circuit 26 via power cable 379 to power conversion circuit 400 where it is modulated by modulator 414 and then amplified by amplifier 415 and transmitted as inducing current 416 along electromagnetic coupling element cable 407 to electromagnetic coupling element 399 where it generated magnetic flux that is detected and decoded by external devices, including power delivery unit 413 as well as with patient interface module 55 and supervisory module 56, shown in FIG. 1. At least one of digital to analog or analog to digital conversion may also be performed without departing from the present invention.

Figure 26:
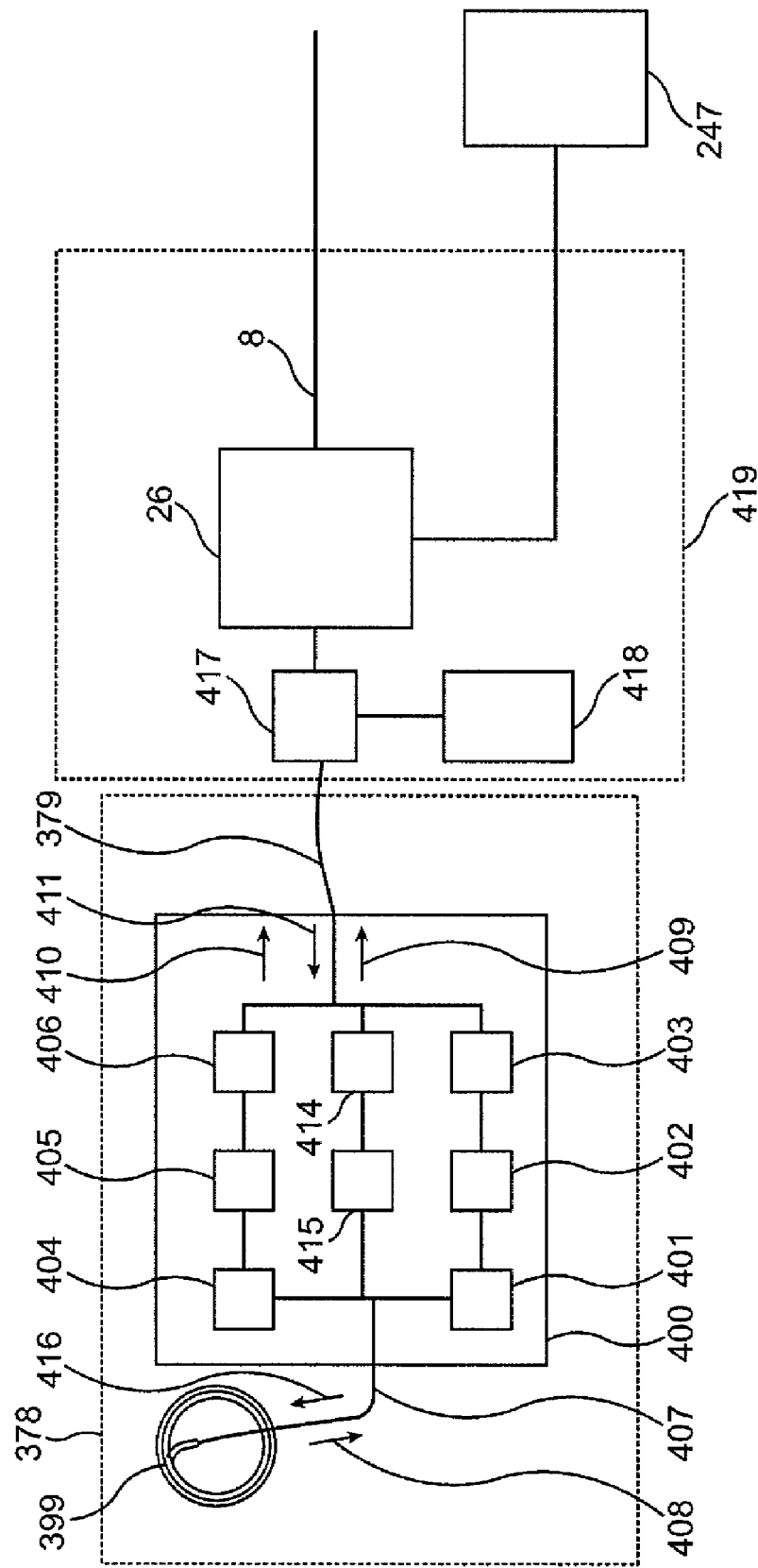
FIG. 26 is a diagram of the overall system.

FIG. 26 depicts the overall system, with power conversion unit 378 connected via power cable 379 to power management unit 417, a component of stimulating recording and power circuit 419. Power management unit 417 is in electrical connection with energy storage unit 418 and in electrical connection with stimulating and recording circuit 26.

In one preferred embodiment, energy storage unit 418 is implemented as a capacitor. Power management unit 417 converts regulated power 409 into charge, which is stored in energy storage unit 418.

In another preferred embodiment, energy storage unit 418 is implemented as a rechargeable battery. Power management unit 417 converts regulated power 409 into current, which recharges energy storage unit 418.

When regulated power 409 is insufficient to power stimulating and recording circuit 26, power management unit 417 withdrawals energy from energy storage unit 418 and delivers energy to stimulating and recording circuit 26.

An embodiment of this invention further includes novel geometrical features to enhance form and function of this neuromodulation system as well as any neural stimulation system. One invention taught is the refinement of the implanted case such that one side is concave. An additional invention taught is the refinement of the implanted case such that one side is convex. A further extension of this invention includes the use of at least one concave side and at least one convex side. Advantages of this design include the close positioning of the casing against the intact outer table of the skull of the patient.

Figure 27:
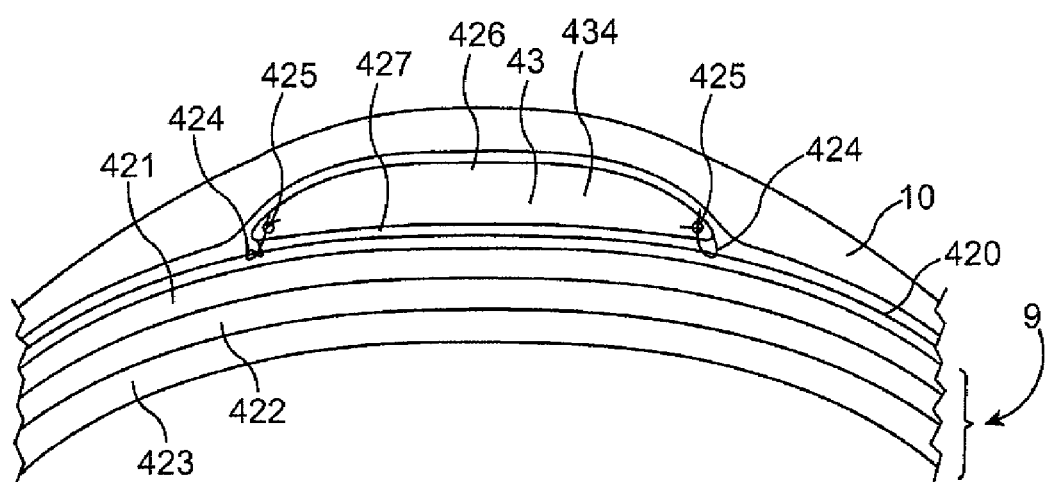
FIG. 27 is a diagram of the stimulating and recording unit.

FIG. 27 shows stimulating and recording unit 43 enclosed within system enclosure 434, implanted beneath the scalp 10, overlying the calvarum 9. System enclosure 434 is designed with an enclosure inner surface 427 and enclosure outer surface 426. In one preferred embodiment, enclosure inner surface 427 and enclosure outer surface 426 are concave and convex, respectively.

By designing enclosure inner surface 427 to be concave, system enclosure 434 may be placed tightly and securely against calvarum 9. This represents a substantial innovation over flat machined enclosures, the designs currently implanted elsewhere and that are based upon established pacemaker technology. This innovation reduces or eliminates movement of the implant that would otherwise occur with existing devices.

By designing enclosure outer surface 426 to be convex, system enclosure 434 may be placed against calvarum 9 with a substantially improved cosmetic result and less displacement of scalp 10 or other skin 382. This represents a substantial innovation over flat machined enclosures, the designs currently implanted elsewhere and that are based upon established pacemaker technology. This innovation reduces or eliminates movement of the implant that would otherwise occur with existing devices.

Furthermore, each of enclosure inner surface 427 and enclosure outer surface 426 serve to reduce the profile of system enclosure 434 and to improve the cosmetic appearance of the overlying skin 382 or scalp 10.

In this embodiment, system enclosure 434 overlies the intact pericranium 420. This facilitates attachment of System enclosure 434 to the pericranium 420 by means of mechanical attachment 424, providing mechanical attachment between mechanical attachment mount 425 and at least one of pericranium 420, skin 382, scalp 10, or other tissue of the patient. Mechanical attachment 424, may be implemented as sutures, wires, clips, or other attachment means. In this embodiment, the calvarum outer table 421, calvarum marrow layer 422, and calvarum inner table 423 remain intact.

Alternatively, System enclosure 434 is implanted beneath the scalp 10 and beneath the pericranium 420, directly overlying the calvarum 9. In this embodiment, the pericranium 420 serves to secure System enclosure 434 in place against the calvarum 9.

Figure 28:
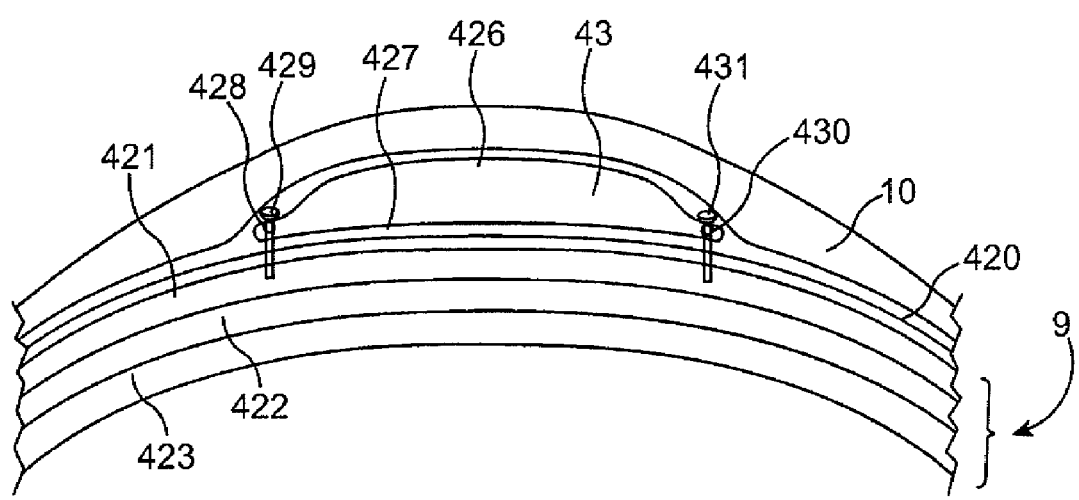
FIG. 28 is a diagram of the system enclosure secured to the calvarium.

FIG. 28 depicts system enclosure 434 secured to the calvarium 9 using screws 429, 431 which are shown inserted through screw mounts 428, 430, respectively, into calvarium 9. Additional or fewer screws and screw mounts may be used without departing form the present invention. Screws 429, 431 may penetrate in depth to the level of the calvarium outer table 421, calvarium marrow layer 422, or calvarium inner table 423.

Figure 29:
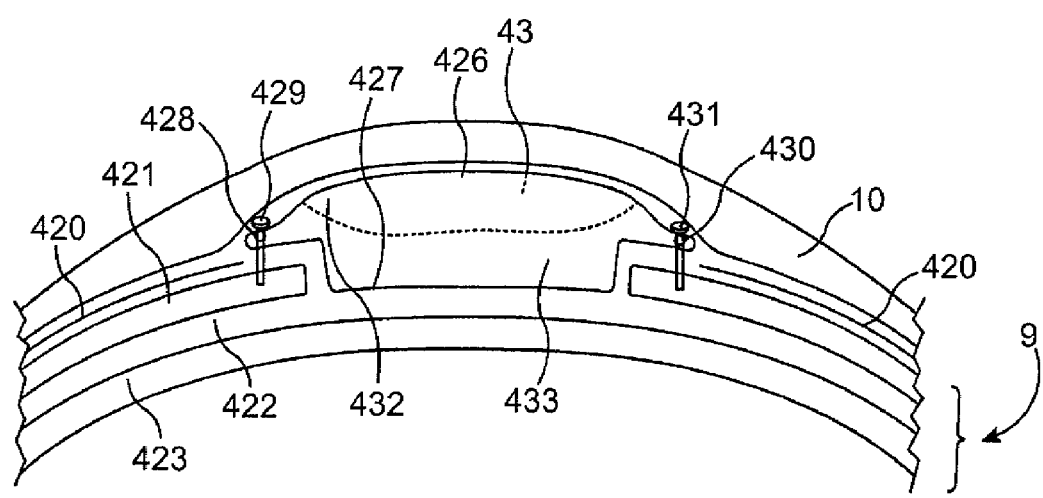
FIG. 29 is a diagram of a lower profile design.

FIG. 29 depicts a lower profile design in which the system enclosure 434 is partially recessed recessed into the calvarium 9. Protruding component 432 lies above the outer surface of calvarium 9, and recessed component 433 lies below the outer surface of calvarium 9. Recessed component 433 is shown occupying volume previously occupied by calvarium outer table 421. Recessed component 433 may also occupying volume previously occupied by calvarium marrow layer without departing from the present invention.

Figure 30:
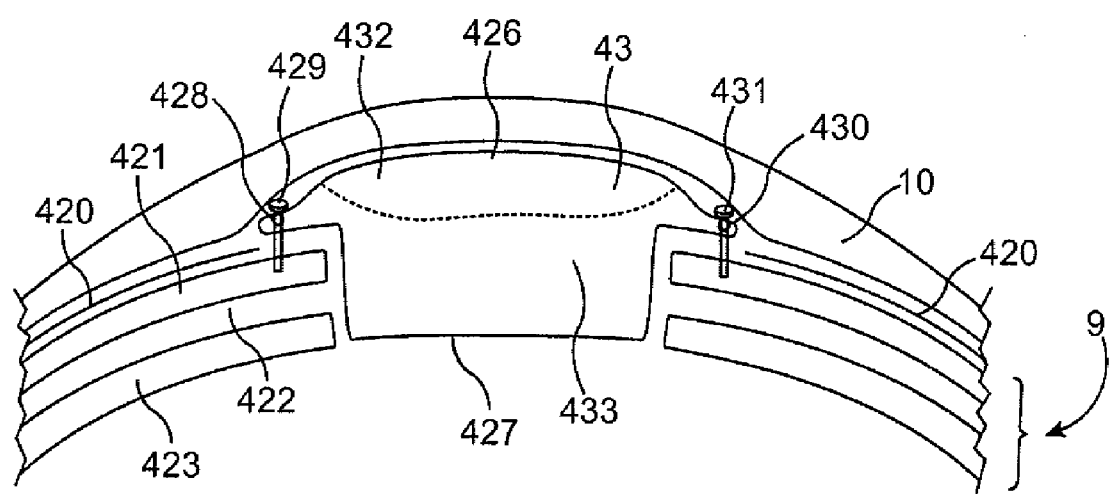
FIG. 30 is a diagram of a lower profile design with the system enclosure partially recessed into the calvarium.

FIG. 30 depicts a lower profile design in which the system enclosure 434 is partially recessed into the calvarium 9. Protruding component 432 lies above the outer surface of calvarium 9, and recessed component 433 lies below the outer surface of calvarium 9. Recessed component 433 is shown occupying volume previously occupied by calvarium outer table 421, calvarium marrow 422, and calvarium inner table 423. System enclosure 434 is shown secured to the calvarium outer table 421 portion of calvarium 9 using screws 429, 431 which are shown inserted through screw mounts 428, 430, respectively. Additional or fewer screws and screw mounts may be used without departing form the present invention. Screws 429, 431 may penetrate in depth to the level of the calvarium outer table 421, calvarium marrow layer 422, or calvarium inner table 423.

Figure 31:
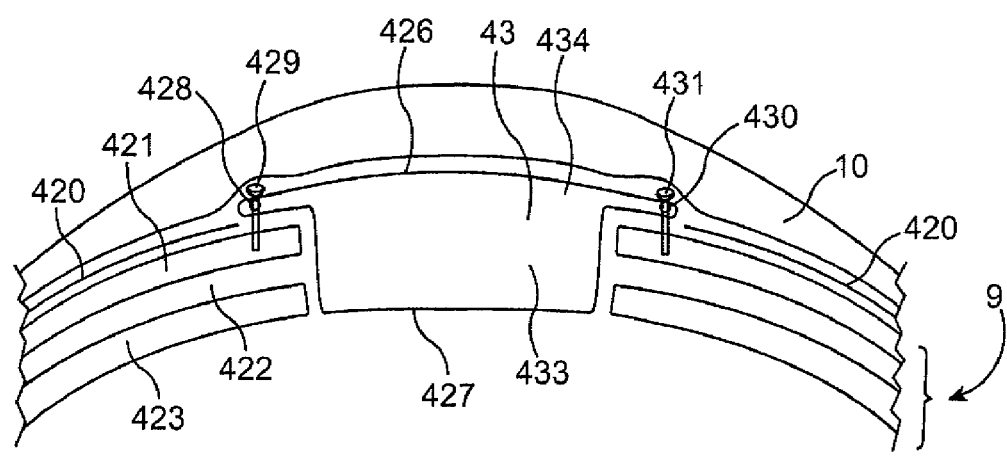
FIG. 31 is a diagram of a lower profile design with the system enclosure fully recessed into the calvarium.

FIG. 31 depicts a lower profile design in which the system enclosure 434 is fully recessed into the calvarium 9. Recessed component 433 lies below the outer surface of calvarium 9. Recessed component 433 is shown occupying volume previously occupied by calvarium outer table 421, calvarium marrow 422, and calvarium inner table 423. System enclosure 434 is shown secured to the calvarium outer table 421 portion of calvarium 9 using screws 429,431 which are shown inserted through screw mounts 428, 430, respectively. Additional or fewer screws and screw mounts may be used without departing form the present invention. Screws 429, 431 may penetrate in depth to the level of the calvarium outer table 421, calvarium marrow layer 422, or calvarium inner table 423.

Figure 32:
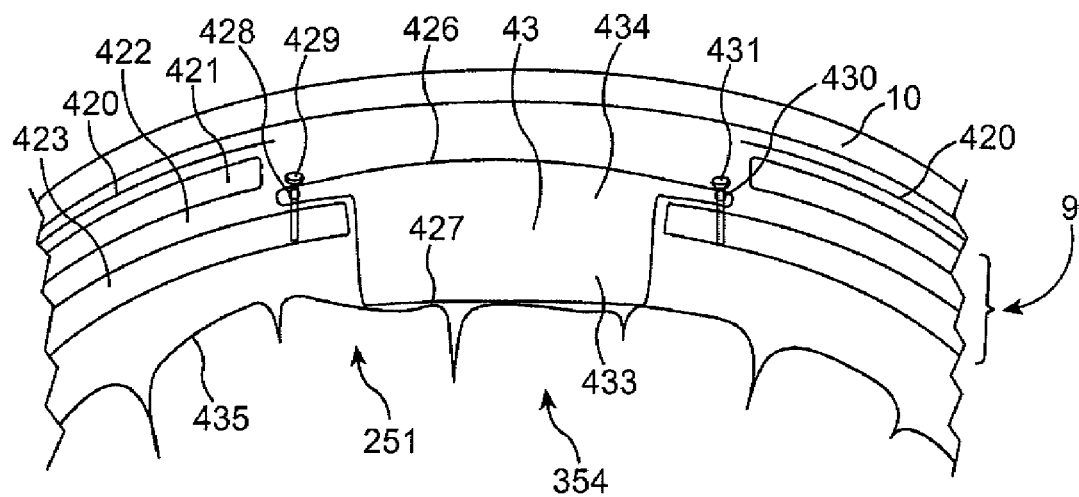
FIG. 32 is a diagram of a second lower profile design with the system enclosure fully recessed into the calvaium.

FIG. 32 depicts a lower profile design in which the system enclosure 434 is fully recessed into the calvarium 9. Recessed component 433 lies below the outer surface of calvarium 9. Recessed component 433 is shown occupying volume previously occupied by calvarium outer table 421, calvarium marrow 422, and calvarium inner table 423. In one embodiment shown, enclosure inner surface 427 is shown extending below the level of calvarium inner table 423. This design facilitates close proximity of stimulating and recording unit 43 to underlying neural tissue 354 and brain 251, valuable in sensing neural activity and in delivering an output neuromodulation signal (NMS) 998 via intracranial stimulating electrode array 37, shown in FIG. 1 and FIG. 2.

System enclosure 434 is shown secured to the calvarium inner table 423 portion of calvarium 9 using screws 429, 431 which are shown inserted through screw mounts 428, 430, respectively. Additional or fewer screws and screw mounts may be used without departing form the present invention. Alternate means of mechanically attaching system enclosure 434 to calvarium 9 may be employed without departing from the present invention.

Figure 33:
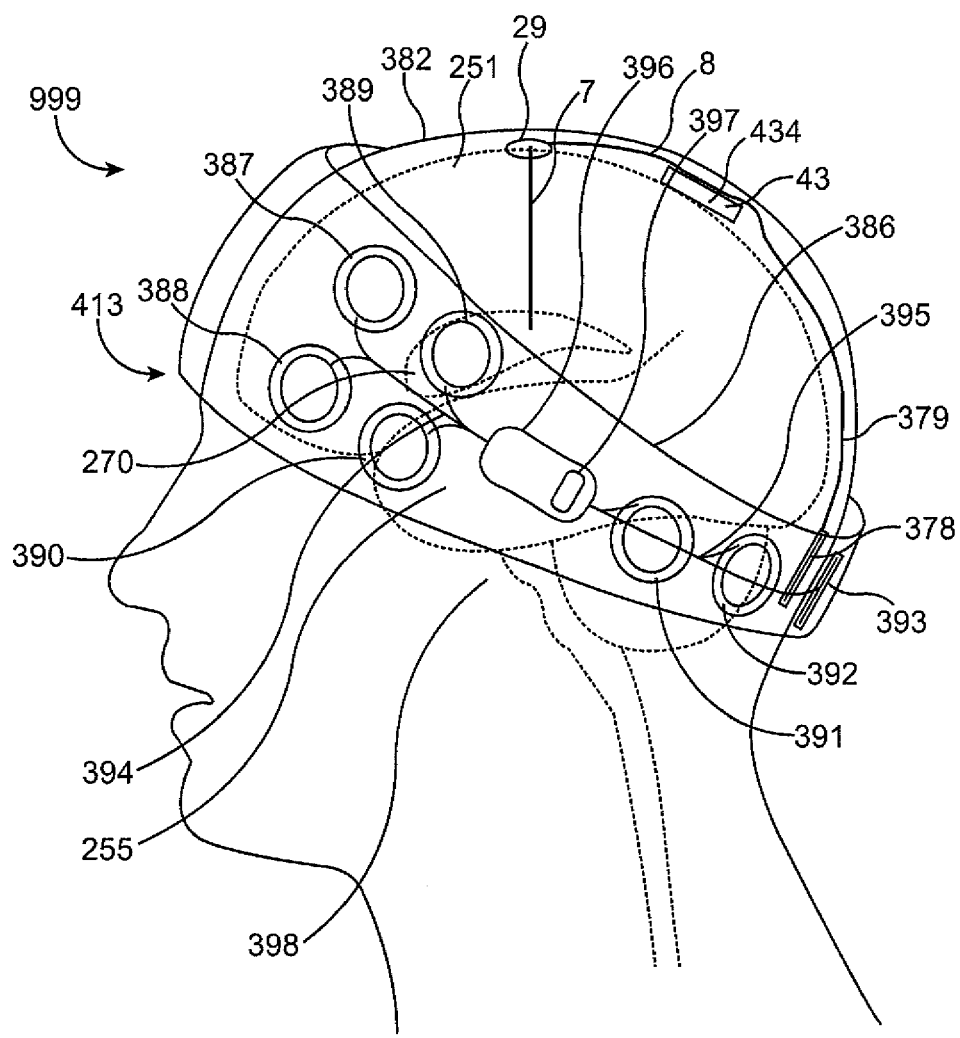
FIG. 33 is a diagram of a neurological control system.

FIG. 33 depicts the neurological control system 999 employing a lower profile design in which the system enclosure 434 is recessed into the calvarium 9. Power delivery unit 413, via generated magnetic flux, transmits power to power conversion unit 378, which transmits power via power cable 379 to stimulating and recording circuit 26, part of stimulating and recording unit 43, contained within system enclosure 434. Stimulating and recording circuit 26 is electrically connected via connecting cable 8 to intracranial catheter 7 which provides electrical connection to intracranial stimulating electrode array 37 and intracranial recording electrode array 38. Intracranial catheter is mechanically secured via catheter anchor 29 to calvarium 9.

Figure 34:
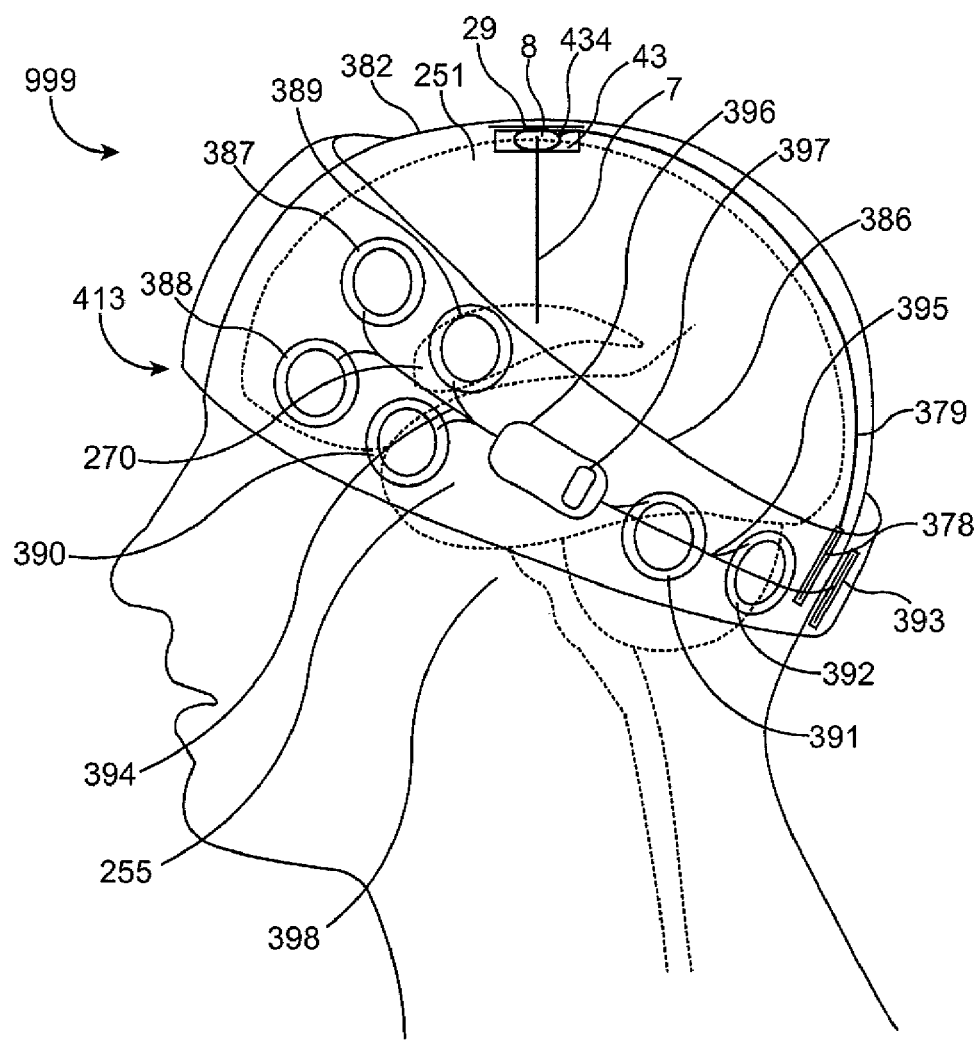
FIG. 34 is a diagram of a second neurological control system.

FIG. 34 depicts the neurological control system 999 employing a lower profile and more compact design in which the system enclosure 434 is recessed into the calvarium 9. Power delivery unit 413, via generated magnetic flux, transmits power to power conversion unit 378, which transmits power via power cable 379 to stimulating and recording circuit 26, part of stimulating and recording unit 43, contained within system enclosure 434.

Stimulating and recording circuit 26 is in close proximity to intracranial catheter 7, this includes but is not limited to a preferred embodiment in which stimulating and recording circuit 26 is recessed into calvarium at the site surrounding the entry point at which intracranial catheter 7 passes from outside the calvarium to inside the calvarium. Stimulating and recording circuit 26 is electrically connected directly or via connecting cable 8 to intracranial catheter 7 which provides electrical connection to intracranial stimulating electrode array 37 and intracranial recording electrode array 38. Intracranial catheter is mechanically secured via catheter anchor 29 to calvarium 9.

An advantage of the closed-loop system includes the natural variability of the output signal. The nervous system exhibits a natural tendency to attenuate responses to continuous stimuli, such as continuous background noises. A natural example includes imperceptibility of stationary visual images on frog retina. A related example is electrical stimulation of peripheral nerves, such as stimulation of the tibial or peroneal nerves for use in eliciting the flexion withdrawal reflex to facilitate gait restoration in paraplegics. With time, these reflexes attenuate or habituate, reducing their effectiveness.

The time-varying nature of a closed-loop signal, responding to environmental and system fluctuations and noise, the natural neural process of habituation to constant signals will be reduced.

Furthermore, by specifically and intentionally altering the output signal, such as intermittently reducing the amplitude of the stimulus, and allowing the closed-loop system to compensate in between these intentional amplitude restrictions, further reduction and prevention of habituation is achieved.

As shown previously, ventricular electrode catheter 1 is shown positioned within the lateral ventricle 2, with ventricular electrode 17 in contact with the CSF fluid 18 in lateral ventricle 2. Cortical electrode 3 is in contact with the CSF fluid overlying the cerebral cortex 19. Cortical electrode 3 may be placed over any portion of the cerebral or cerebellar cortex without departing from the present invention. Hippocampal electrode 4 is shown underlying the hippocampal regions of the cerebrum.

The parenchyma of the nervous system is used as a dielectric to establish a voltage potential gradient between any of the CSF reservoirs, including the lateral ventricles, third ventricle, cerebral aqueduct, fourth ventricle, foramen of lushke, foramen of magende, basal cisterns, CSF overlying the cerebellar hemispheres, CSF overlying the cerebral hemispheres, central spinal canal, CSF overlying the spinal cord, and CSF overlying the spinal nerves and roots.

Patients currently implanted with neuromodulation devices must undergo repeat surgery to replace implanted pulse generators every 3–5 years to replace units when batteries fail. Tradeoffs between acceptable implanted device size and limited energy density with current battery technology are responsible for this pervasive problem. Many of these patients are older, and the risks of general anesthesia and surgery are not insignificant. Subjecting these patents to these large risks is a pervasive problem in the field of neuromodulation. The present invention overcomes these limitations with a clever design employing a novel external radio frequency power delivery system.

The present embodiment of the invention includes an external coil use of Limited energy density because technology is limited.

The present embodiment of this invention teaches a device, method of implantation, and surgical tools for the rapid implantation of a neuromodulation system. Current devices suffer form the need to implant a pulse generator in the subclavicular pocket or other site remote form the site of electrode implantation. Because of this, subcutaneous cables must be implanted to connect the implanted circuit to the implanted stimulating electrode. The present invention teaches a device and method for implanting the circuit in close proximity to the site of stimulation. The design taught herein obviates the need for any subcutaneous cables. Additionally, it teaches a compact design that allows placement of the implanted circuit and the implantation of the intracranial electrode catheter through a single hole. This is a substantial improvement, facilitating much more rapid implantation and eliminating the need for subcutaneous cable implantation. As a result, surgical procedures are much faster and may be performed under local anesthesia, no longer requiring general anesthesia. This substantially increases the market size, allowing implantation in older and frail patients who might otherwise not benefit from neuromodulation technology because of their being poor surgical candidates, due to their inability to safely tolerate general anesthesia and long surgical procedures.

Figure 35:
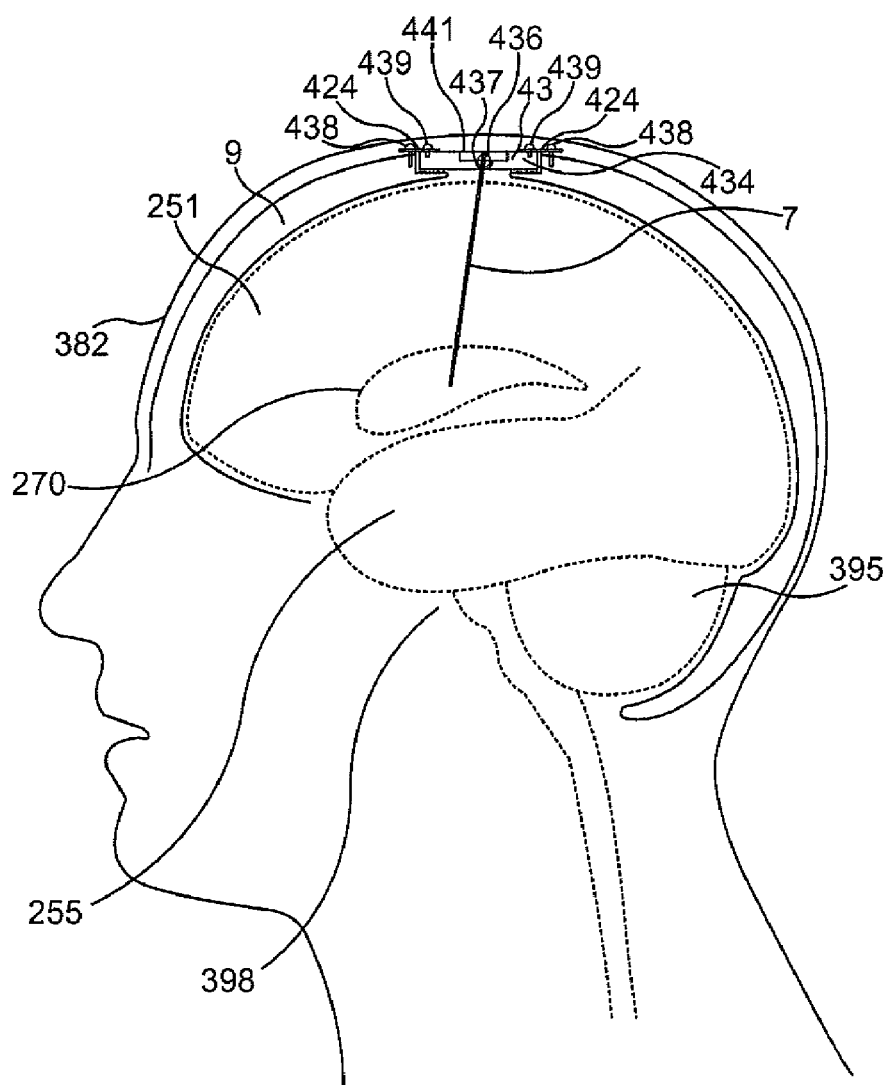
FIG. 35 is a schematic diagram of one embodiment of the present invention implanted unilaterally in a human patient, with the system enclosure recessed in the calvarium, shown as a lateral view.
Figure 36:
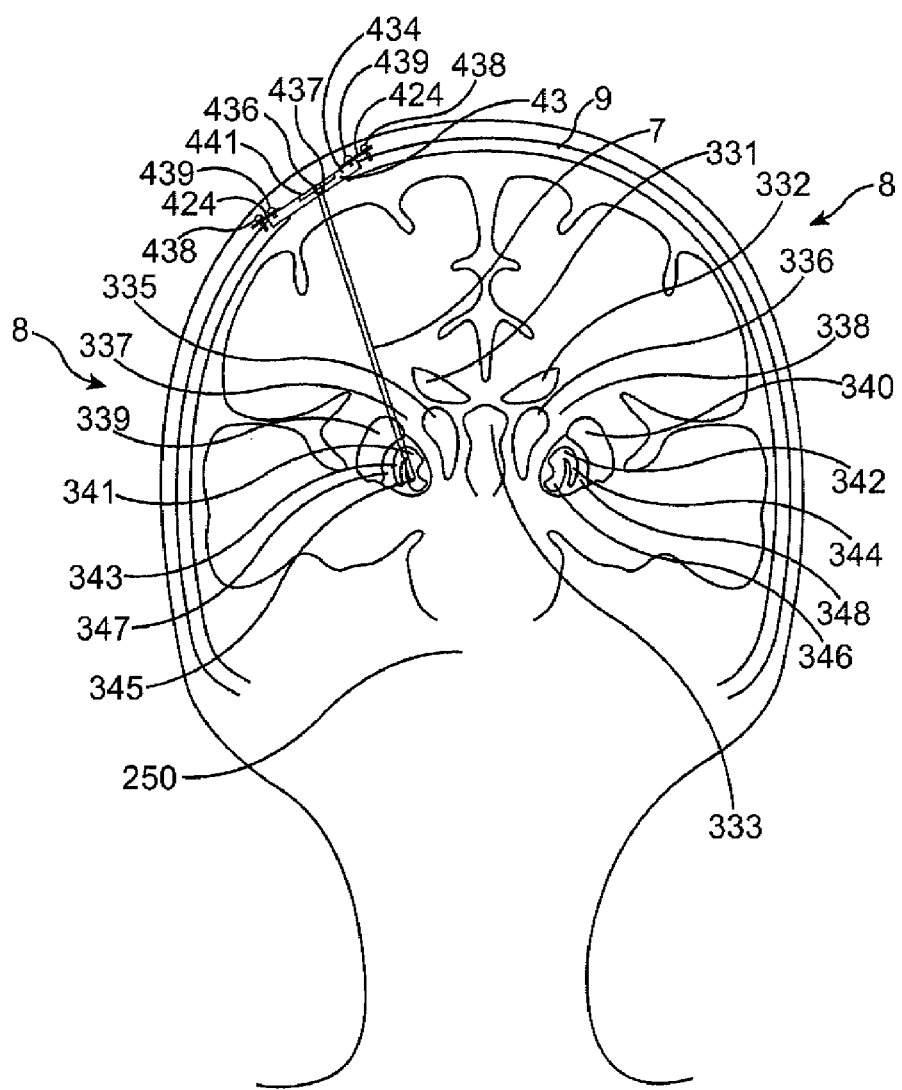
FIG. 36 is a schematic diagram of one embodiment of the present invention implanted unilaterally in a human patient, with the system enclosure recessed in the calvarium, shown as a anteroposterior view.

FIGS. 35 & 36 depict the neurological control system 999 employing a lower profile and more compact design in which the system enclosure 434 is recessed into the calvarium 9, shown in the anteroposterior and lateral projections, respectively. Power delivery unit 413, is included within system enclosure 434; however, power delivery unit 413 may also be external to system enclosure 434 without departing from the present invention.

Stimulating and recording circuit 26 is in close proximity to intracranial catheter 7, this includes but is not limited to a preferred embodiment in which stimulating and recording circuit 26 is recessed into calvarium at the site surrounding the entry point at which intracranial catheter 7 passes from outside the calvarium to inside the calvarium. Stimulating and recording circuit 26 is electrically connected to intracranial catheter 7 which provides electrical connection to intracranial stimulating electrode array 37 and intracranial recording electrode array 38. Intracranial catheter is mechanically secured to system enclosure 434. System enclosure 434 is secured to calvarium 9 via mechanical attachment 424, which is attached to system enclosure 434 via machine screw 439 or equivalent means and to calvarium 9 via bone screw 438 or equivalent means. Catheter recess 441 provides space for establishment of electrical and mechanical connection of stimulating and recording circuit 26 to intracranial catheter 7. Catheter mount socket 437 and catheter mount ball 436.

Figure 37:
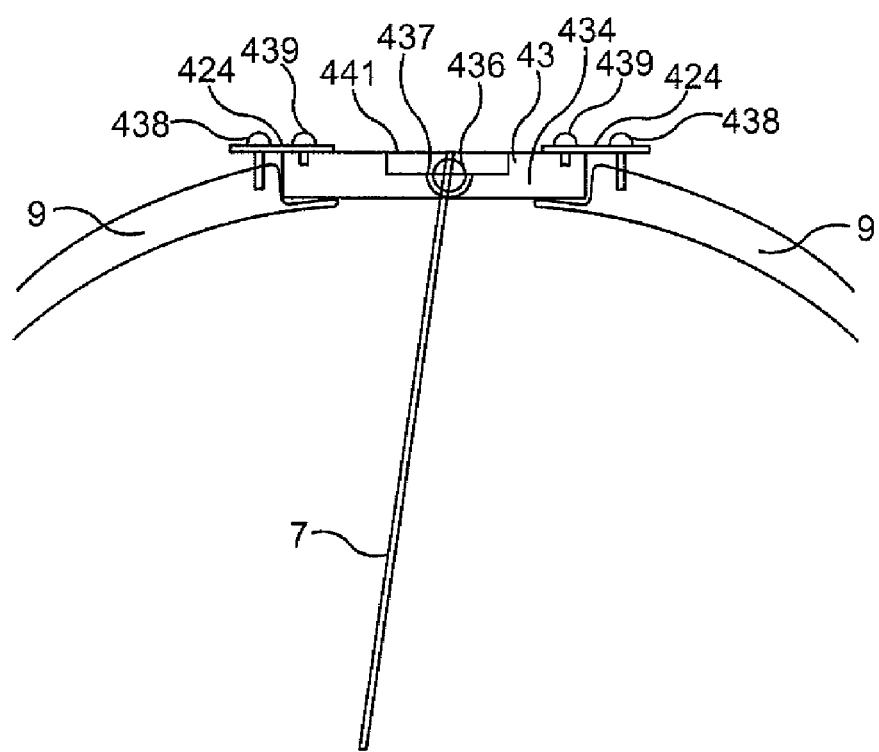
FIG. 37 is a schematic diagram of a cross section of calvarium with system enclosure shown implanted recessed within the calvarium.

FIG. 37 shows an expanded view of the neurological control system 999 also shown in FIGS. 35 & 36.

Figure 38:
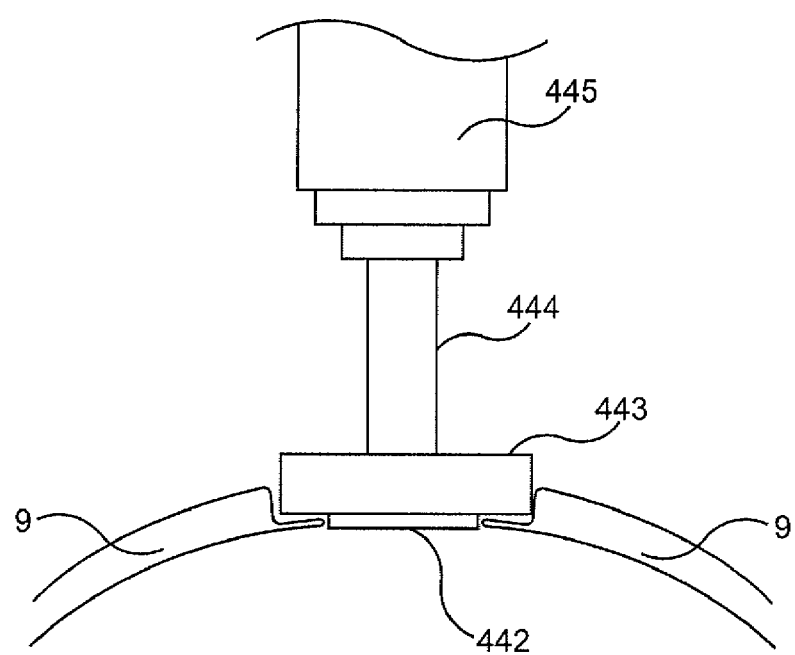
FIG. 38 is a schematic diagram of a cross section of calvarium with drill bit shown in place after completion of process of drilling hole in calvarium.
Figure 39:
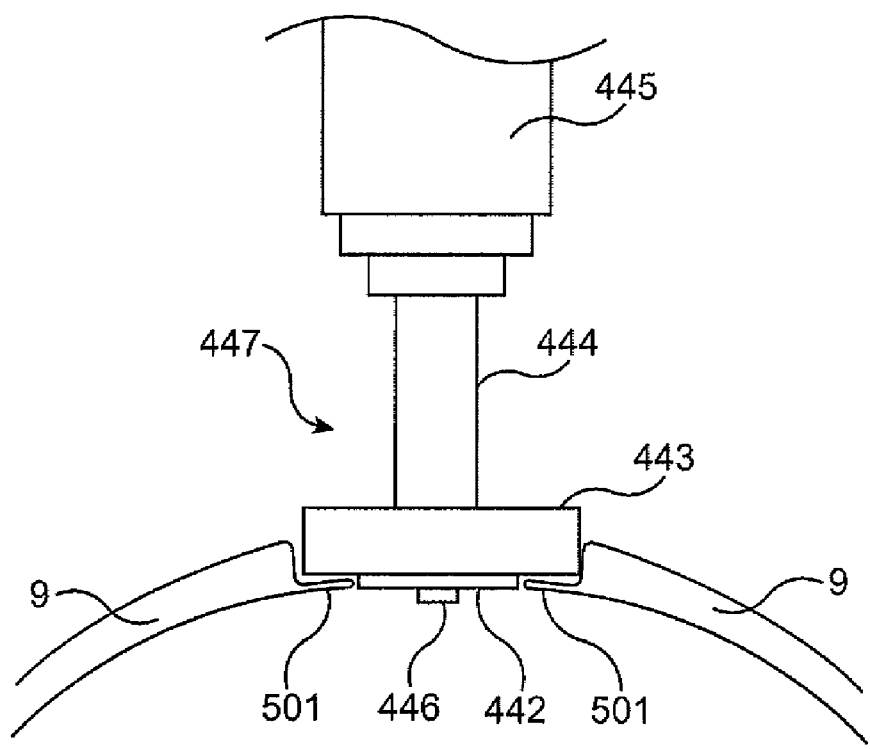
FIG. 39 is a schematic diagram of a cross section of calvarium with drill bit, with a penetration detection release mechanism, shown in place after completion of process of drilling hole in calvarium.

FIGS. 38 & 39 depict a Calvarum drill bit is used to create a circular hole in the calvarium. The present invention teaches a major advance in the expeditiousness of the implantation procedure for creating a craniotomy, with particular relevance to the implantation of a neuromodulation device recessed in the calvarium. In a single pass, a drill bit creates a hole of a diameter similar to that of the implanted device. The outer diameter portion is created by calvarium bit outer diameter segment 443. Attached to and deep to calvarium bit outer diameter segment 443 is the calvarium bit inner diameter segment 442, which creates a hole in the calvarium of a smaller diameter. The resulting geometry, as seen in FIG. 38 and FIG. 39, produces bone ledge 447. Bone ledge 447 serves to provide mechanical support to system enclosure 434, preventing system enclosure 434 from becoming displaced and impinging upon brain 251.

Intracranial catheter 7 is secured to system enclosure 434 by means of catheter mount ball 436. A compressible material is either adjacent to or comprises catheter mount ball 436.

Figure 40:
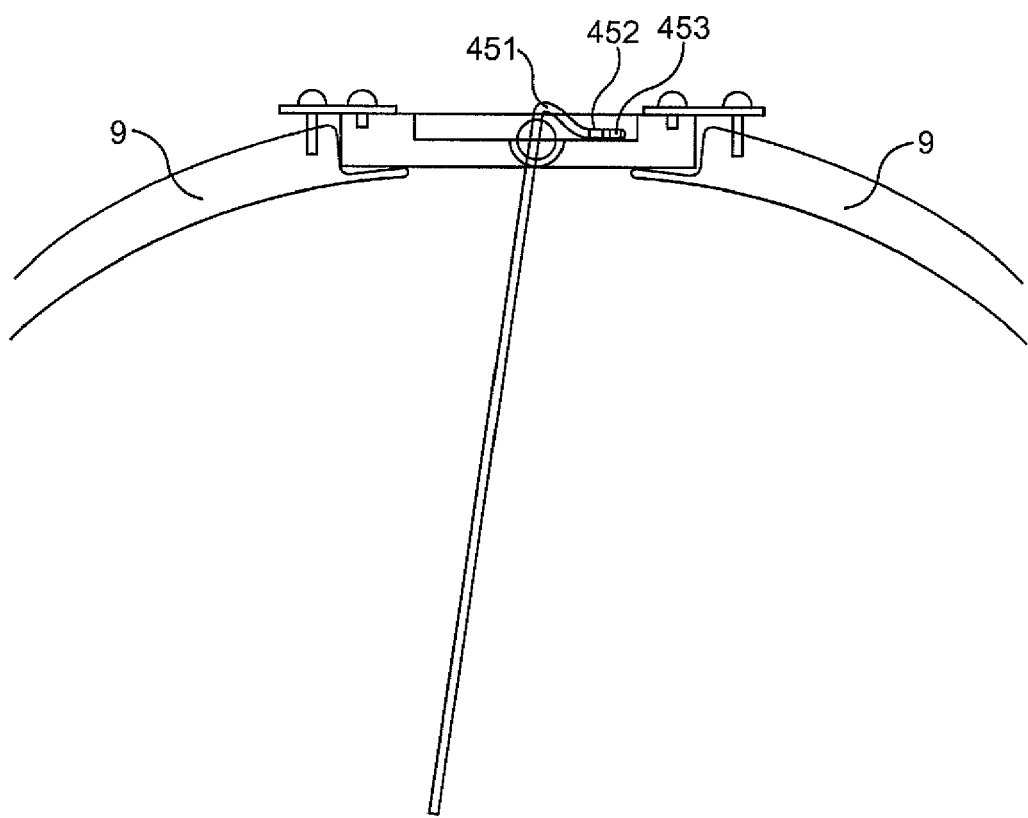
FIG. 40 is a diagram depicting the path of the intracranial catheter and its connection to the electrical elements.

FIG. 40 depicts the path of the intracranial catheter 7 and its connection to the electrical elements of stimulating and recording circuit 26, which is contained within system enclosure 434 and in close proximity to intracranial catheter 7. Intracranial Catheter Proximal End 451 is largely contained within or at least has a component that occupies a portion of the catheter recess 441. Intracranial Catheter Proximal Electrode 452 and Intracranial Catheter Proximal Electrode 453 are shown. Additional electrodes or alternate connection means may be employed without departing from the present invention.

In one embodiment, set screws are used to electrically connect electrodes on intracranial catheter 7 to contacts mounted on system enclosure 434. Electrode contacts and set screw are recessed in catheter recess 441 in system enclosure 434.

System enclosure is constructed from a castable material, such as potted epoxy, methylmethacrylate, or other plastic, silicone, or polymer. RF electrodes are included within the system enclosure. A titanium or stainless steel shield may be included into eh center of the system enclosure 434. The outer surface of system enclosure 434 may have a convex shape, to better approximate the shape of the calvarium removed and replaced by system enclosure 434, and the convex shape of outer surface of system enclosure 434 minimized stress concentrations on the overlying scalp 10.

Disease state is estimated using a measure or estimate of chaos of neural activity. Such measures include Lyupanov functions and other measures of chaos or system synchronicity or correlation.

Bottom surface of system enclosure 434 may include electrodes used for at least one of recording, stimulation, ground, or reference electrode functions.

An array of at least one EEG electrode is used for recording electroencephalographic signals. Said EEG electrode may be placed in at least one of a subgaleal location, subcutaneous location, epidural location, subdural location, intracerebral location, or other location enabling EEG electrode to sense neural activity.

An advancement in intracranial catheter design is taught in the present invention. Intracranial catheter 7 includes a microelectrode channel 448. Microelectrode 449 is inserted through microelectrode channel 448, with microelectrode tip 450 protruding beyond tip of intracranial catheter 7. Microelectrode tip 450 is used to record single cell activity to identify neural structures during advancement of intracranial catheter 7 through brain 251. At the completion of the insertion of intracranial catheter 7 through brain 251, microelectrode 449 may be removed from intracranial catheter 7.

This allows microelectrode recording and implantation of intracranial catheter 7 during a single pass, saving substantial time during the implantation procedure.

During and Following implantation, closed-loop optimization of electrical field shaping is performed by control circuit 72.

Disease state is characterized by a measure of correlation between neural signals measured from neural tissue. Disease State DS is a vector of individual disease states, including intrinsic disease states DSI and extrinsic disease states DSE:

$$DS=[DS_I DS_E]$$

Intrinsic disease states and extrinsic disease states are, themselves vectors of individual disease states:

$$DS_I=[DS_{I1} DS_{I2} DS_{I3} \ldots DS_{IN}]$$

$$DS_E=[DS_{E1} DS_{E2} DS_{E3} \ldots DS_{EM}]$$

Intrinsic Disease States include those disease states which characterize the state of disease at a given point in time. Extrinsic Disease States include variations of intrinsic disease states, including but not limited to cyclical variations in Intrinsic Disease States, variations in Intrinsic The fifth intrinsic disease state $DS_{I5}$ represents the level of correlation between neural activity in multiple areas of the nervous system.

$$DS_{I5}=C_N$$

Where Normalized Correlation Magnitude matrix $C_N$ is given by:

$$C_N = \begin{bmatrix} C_{1,1} & C_{1,2} & C_{1,3} & \ldots & C_{1,M} \\ C_{2,1} & C_{2,2} & C_{2,3} & \ldots & C_{2,M} \\ C_{3,1} & C_{3,2} & C_{3,3} & \ldots & C_{3,M} \\ \ldots & \ldots & \ldots & \ldots & \ldots \\ C_{M,1} & C_{M,2} & C_{M,3} & \ldots & C_{M,M} \end{bmatrix}$$

Which becomes:

$$C_N = \begin{bmatrix} 1 & C_{1,2} & C_{1,3} & \ldots & C_{1,M} & ; \\ C_{2,1} & 1 & C_{2,3} & \ldots & C_{2,M} & ; \\ C_{3,1} & C_{3,2} & 1 & \ldots & C_{3,M} & ; \\ \ldots & \ldots & \ldots & \ldots & \ldots & ; \\ C_{M,1} & C_{M,2} & C_{M,3} & \ldots & 1 & \end{bmatrix}$$

This matrix or a weighted sum of its components represents an additional measure of disease state. This has broad applications in neurological disease quantification and also has particular relevance to measurement of tremor and assessment of seizure activity as well as prediction of likelihood and onset of seizure activity.

$$C_N = C_{1,2} * W_{1,2} + C_{1,3} * W_{1,3} + \ldots + C_{1,M} * W_{1,M} +$$
$$C_{2,1} * W_{2,1} + C_{2,3} * W_{2,3} + \ldots + C_{2,M} * W_{2,M} +$$
$$C_{3,1} * W_{3,1} + C_{3,2} * W_{3,2} + \ldots + C_{3,M} * W_{3,M} + \ldots$$
$$C_{M,1} * W_{M,1} + C_{M,2} * W_{M,2} + C_{M,3} * W_{M,3} + \ldots$$

Where
$C_{I,J}$=Correlation between signal I and signal J
$W_{I,J}$=Weighting factor for Correlation between signal I and signal J The sixth intrinsic disease state $DS_{I6}$ represents the level of chaos in neural activity in a single or multiplicity of areas of the nervous system. This may be implemented as any measure of entropy or chaos, including variance, standard deviation, Lyupanov exponent values, maximum Lyupanov exponent value, or other measure of entropy or chaos without departing from the present invention.

$DS_{I6}=S_N$ $DS_{I6}=S_1*W_{S1}+S_2*W_{S2}+S_3*W_{S3}+\ldots+S_N*W_{SN}$

Where
$S_I$=Entropy measure for signal I, which may be implemented in any of several ways outlined above, some of which are detailed below.
$W_{SI}$=Weighting factor for Entropy measure for signal I Chaos measurement implemented and quantified as Entropy:

$$S_1 = \text{Entropy measure for signal } I$$
$$= -k \int [dX] P[X_I] \log P[X_I]$$

Where
k=a constant, i.e. Boltzmann's constant as in thermodynamics, or by convention a dimensionless constant in information theory
$X_I$=Signal I, such as EEG voltage signal I or implanted electrode signal I or microelectrode voltage signal I
$P[X_I]$=Probability distribution of Signal I
dX=integration variable In a typical implementation in digital hardware, based upon a base 2 digitization scheme, chaos measurement implemented and quantified as Entropy becomes:
$S_I=-\Sigma p_i \log_2 p_i$ bits Where
$S_I$=Entropy measure for signal I
$p_i$=probability of outcome i, for example of sensed voltage being within a particular discretization bin window or value range.
$\log_2 p_i$=Log base 2 of $p_i$, alternative bases could be used, but 2 is typically chosen to be consistent with digital hardware, which is implemented using the binary (base 2) system Chaos measurement implemented and quantified as Lyupanov exponent, which is defined as:

$$S_I = L = \left(\frac{1}{\sum_{k=1}^{M} Dt_k}\right) \times \sum_{k=1}^{M} L_k$$

bits per second
Where
L=Lyupanov Exponent
$L_k$ Satisfies the condition: $L(t_k)=L(t_{k-1})*2^{L_k*Dt_k}$
$Dt_k=t_k-t_{k-1}$ is the evolution time of $L(t_k)$
$L(t_k)$ Is the distance between two close points in phase space at time $t_k$
$S_I$=Entropy measure for signal I, calculated with Lypoanov Exponent Other measures of chaos, including variations of these and other measures or estimates for chaos, may be used without departing from the present invention.

FIGS. 37 and 40 show system enclosure in cross section, in which intracranial catheter 7 traverses catheter mount ball 436, which rotates within catheter mount socket 437, providing a swivel mechanism to facilitate the selection of a continuum of potential intracranial target sites for intracranial electrode array and intracranial catheter using a single mounted position for system enclosure 434 on calvarum 9.

The reader is requested to note the following labels on FIG. 37:
Catheter mount ball 436
Catheter mount socket 437
stimulating and recording unit 43

Figure 41:
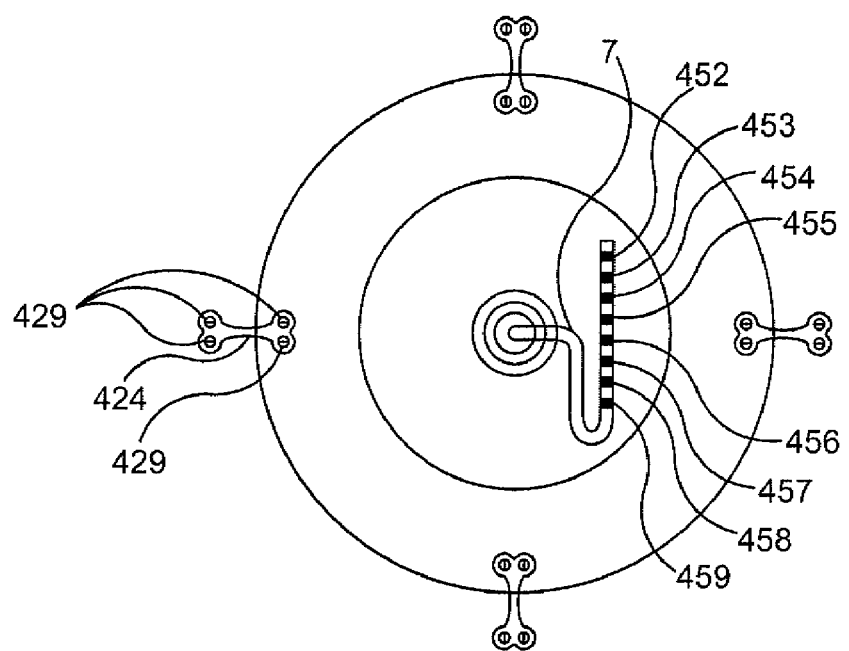
FIG. 41 depicts one design for the system enclosure for implantation in the calvarium.

FIG. 41 depicts one design for the system enclosure for implantation in the calvarium. Mechanical attachment 424 is shown in plurality, facilitating mechanical attachment of system enclosure 434 to calvarium 9, including calvarium outer table 421 or calvarium inner table 423, calvarium stabilization lip 501, or other portion of calvarium without departing from the present invention. Alternatively, other attachment means may be fashioned to perform the equivalent function of attaching system enclosure 434 to calvarium 9 without departing from the present invention. A single or plurality of screw 429 is used to perform the attachment of mechanical attachment 424 to calvarium 9 and to system enclosure 434. Mechanical attachment may be implemented as a cranial plate, craniofacial plate, or other form well known to neurosurgeons, or it may be implemented in another equivalent fashion without departing form the present invention.

Electrode 452, 453, 454, 455, 456, 457, 458, 459, are shown on the end of intracranial catheter 7, said electrode facilitate contact between intracranial electrodes xxx, xxx, xxx, and circuitry enclosed within system enclosure 434, including but not limited to output stage, signal conditioning circuit, signal processing circuit, control circuit, and other circuit components.

Figure 42:
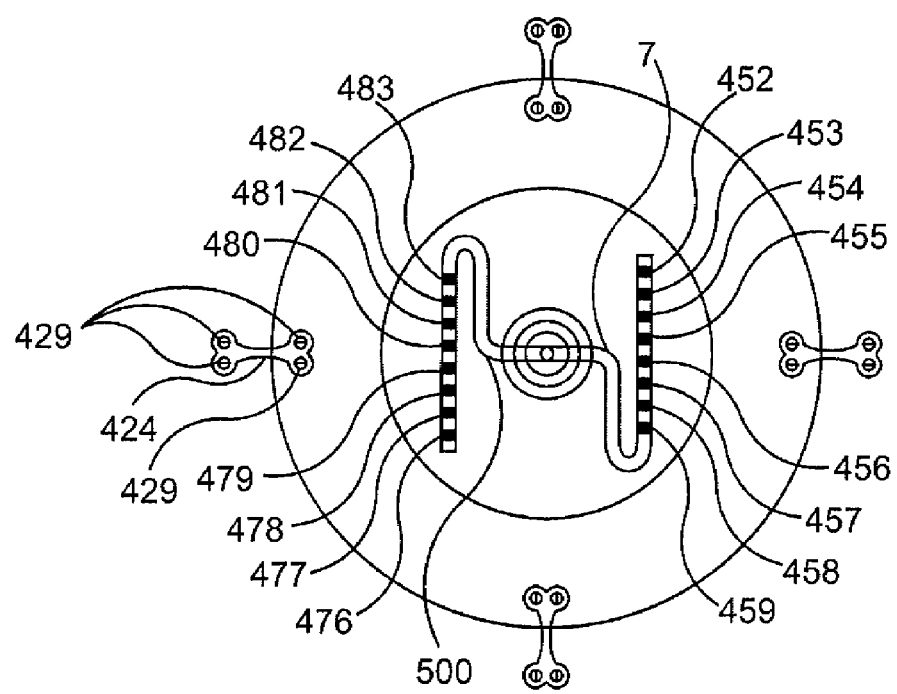
FIGS. 42 and 43 depict a dual intracranial catheter design.
Figure 43:
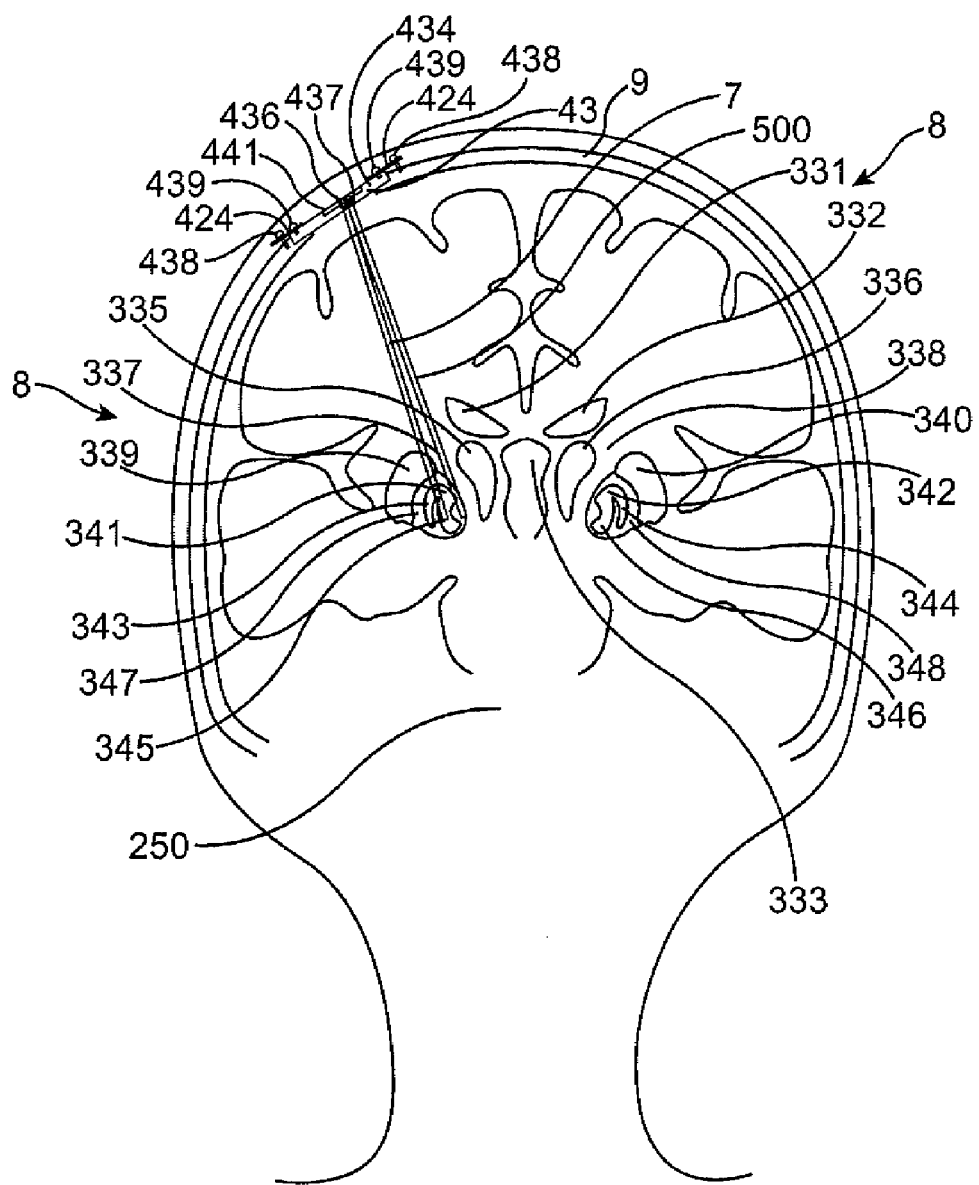

FIGS. 42 and 43 depict a dual intracranial catheter design, shown from above and shown in cross section profile implanted in a patient, respectively. Mechanical attachment 424 are as described in FIG. 41. Intracranial catheter 7 and Electrode 452, 453, 454, 455, 456, 457, 458, 459 are as described in FIG. 41. Electrode 476, 477, 478, 479, 480, 481, 482, 483 are shown on the end of intracranial catheter 500. A multiplicity of intracranial catheter y or intracranial catheter 500 may be employed without departing from the spirit of the present invention. In FIG. 423, a plurality of bone screw 438 is shown facilitating mechanical attachment of mechanical attachment 424 to calvarum 9. In FIG. 43, a plurality of machine screw 439 is shown facilitating mechanical attachment of mechanical attachment 424 to system enclosure 434. In FIG. 43, catheter recess 441 is seen in cross section, providing space for intracranial catheter 7 and intracranial catheter 500 to minimize the profile or height of system enclosure and avoid surface protuberances that could cause ulceration of overlying portions of scalp 10.

Figure 44:
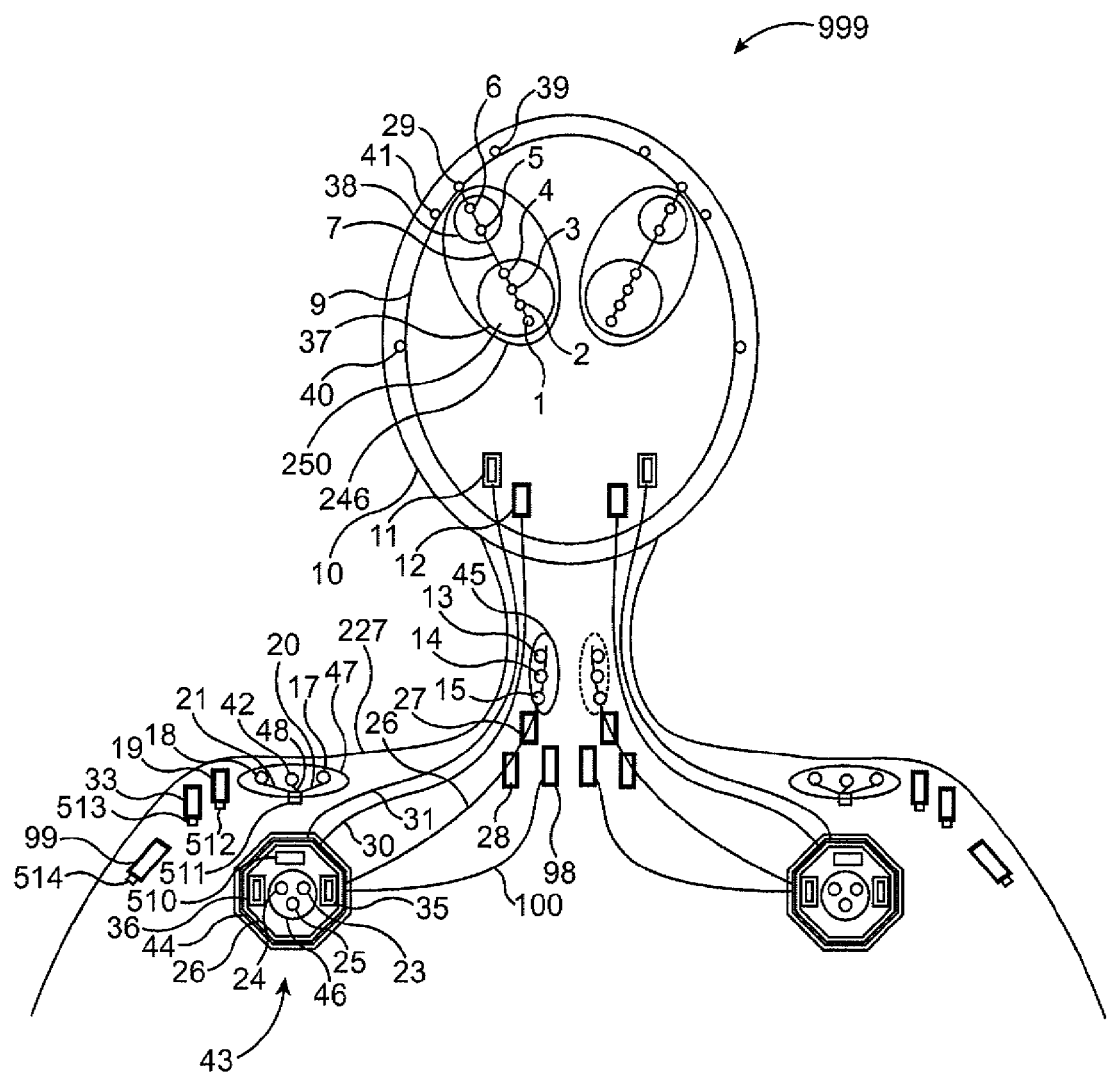
FIG. 44 is a schematic diagram of one embodiment of the present invention implanted bilaterally in a human patient.

FIG. 44 is a schematic diagram of one embodiment of the intracranial stimulator of the present invention implanted bilaterally in a human patient. In the embodiment illustrated in FIG. 44, two neurological control systems 999 are shown implanted bilaterally. Each system 999 includes a stimulating and recording unit 26 and one or more intracranial components described below. As described in this illustrative embodiment, the intracranial components preferably include a stimulating electrode array 37. However, it should become apparent to those of ordinary skill in the relevant art after reading the present disclosure that the stimulating electrodes may also be extracranial; that is, attached to a peripheral nerve in addition to or in place of being located within the cranium.

The invention claimed is:

1. A system for neural modulation in the treatment of disease, comprising:
   a system enclosure, in mechanical communication with a calvarium;
   a control circuit enclosed within said system enclosure and in electronic communication with an output stage circuit, wherein said control circuit employs a calculation of seizure prediction; and
   a stimulating electrode array, in electronic communication with said output stage circuit,
   wherein said control circuit is configured to monitor an impedance of the stimulating electrode array.

2. The system of claim 1 comprising one or more sensors in communication with the control circuit, wherein the one or more sensors are configured to measure one or more signals from a nervous system component of a patient.

3. The system of claim 2 wherein at least one of the one or more sensors is disposed intracranially.

4. The system of claim 1 wherein said stimulating electrode array is configured to deliver stimulation to a vagus nerve of a patient.

5. The system as recited in claim 1, wherein said control circuit employs a calculation of a measure of chaos.

6. The system as recited in claim 1, wherein said control circuit employs a calculation of entropy.

7. The system as recited in claim 1, wherein said control circuit employs a calculation of a Lyupanov exponent.

8. The system as recited in claim 1, wherein said control circuit employs a calculation of a maximal state control.

9. A system for neural modulation in the treatment of disease, comprising:
   a system enclosure, in mechanical communication with a calvarium;
   a control circuit enclosed within said system enclosure and in electronic communication with an output stage circuit, wherein said control circuit employs a calculation of seizure prediction, and wherein said control circuit comprises a non-linear control law to generate a control law output signal that specifies parameters of a neuromodulation signal that is delivered by the output stage circuit, and
   a stimulating electrode array, in electronic communication with said output stage circuit.

10. A system for neural modulation of a patient for the treatment of epilepsy, the system comprising:
    a signal processor configured to process one or more signals received from a patient;
    an output assembly in communication with the signal processor, the output assembly being configured to analyze the processed one or more signals for seizure prediction, wherein the output assembly calculates and generates a neural modulation signal when a seizure is predicted; and
    one or more electrodes that are in communication with the output assembly, the one or more electrodes configured to deliver the neural modulation signal to the patient,
    wherein the one or more signals comprise EEG signals, and wherein the seizure prediction employs analyzing spike parameters of the EEG signals.

11. The system of claim 10 further comprising a system enclosure that is configured to be coupled with a calvarium.

12. The system of claim 10 wherein the output assembly comprises:
    a control circuit that is configured to analyze the processed one or more signals to calculate parameters of the neural modulation signal and generate an output signal; and
    an output stage circuit that receives the output signal from the control circuit and generates the neural modulation signal with parameters that are specified by the output signal.

13. The system of claim 10 wherein seizure prediction employs, a calculation of entropy.

14. The system of claim 10 wherein seizure prediction employs a calculation of chaos.

15. The system of claim 10 wherein the spike parameters comprise at least one of peak-to-valley times, valley-to-peak times, positive phase amplitudes, and negative phase amplitudes.

16. The system of claim 10 wherein the one or more electrodes deliver the neural modulation signal directly to a vagus nerve.

\* \* \* \* \*